US011001898B2

(12) United States Patent
Bitene et al.

(10) Patent No.: US 11,001,898 B2
(45) Date of Patent: May 11, 2021

(54) DETECTION OF COLORECTAL CANCER

(71) Applicant: Universal Diagnostics, S.L., Seville (ES)

(72) Inventors: Marko Bitene, Seville (ES); Kristi Kruusmaa, Seville (ES); Juan Martinez-Barea, Seville (ES); Christian Hense, Seville (ES); Pol Sola de los Santos, Seville (ES); Pol Canal Noguer, Seville (ES); Marko Chersicola, Ljubljana (SI); Primož Knap, Ljubljana (SI)

(73) Assignee: Universal Diagnostics, S.L., Seville (ES)

( * ) Notice: Subject to any disclaimer, the term of this patent is extended or adjusted under 35 U.S.C. 154(b) by 0 days.

(21) Appl. No.: 16/831,756

(22) Filed: Mar. 26, 2020

(65) Prior Publication Data

US 2020/0377959 A1 Dec. 3, 2020

Related U.S. Application Data

(63) Continuation-in-part of application No. 16/428,865, filed on May 31, 2019.

(60) Provisional application No. 62/956,059, filed on Dec. 31, 2019.

(51) Int. Cl.
*C12Q 1/68* (2018.01)
*C12Q 1/6886* (2018.01)
*C12Q 1/686* (2018.01)

(52) U.S. Cl.
CPC ........... *C12Q 1/6886* (2013.01); *C12Q 1/686* (2013.01); *C12Q 2600/154* (2013.01)

(58) Field of Classification Search
None
See application file for complete search history.

(56) References Cited

U.S. PATENT DOCUMENTS

| 6,265,171 | B1 | 7/2001 | Herman et al. |
| 6,605,432 | B1 | 8/2003 | Huang |
| 6,812,339 | B1* | 11/2004 | Venter ................. C12Q 1/6883 435/6.11 |
| 7,144,701 | B2 | 12/2006 | Huang |
| 7,745,391 | B2* | 6/2010 | Mintz ..................... A61P 31/00 514/19.3 |
| 7,807,358 | B1 | 10/2010 | Huang |
| 8,048,634 | B2 | 11/2011 | Lai |
| 9,745,622 | B2 | 8/2017 | An et al. |
| 10,006,925 | B2 | 6/2018 | Bitenc et al. |
| 10,428,388 | B2 | 10/2019 | An et al. |
| 2010/0167940 | A1 | 7/2010 | Feinberg |
| 2010/0240549 | A1 | 9/2010 | Brown |
| 2010/0298158 | A1 | 11/2010 | DePinho et al. |
| 2015/0011403 | A1 | 1/2015 | Lo et al. |
| 2016/0355885 | A1 | 12/2016 | Weinhausel et al. |
| 2017/0335401 | A1 | 11/2017 | Allawi et al. |
| 2017/0369948 | A1 | 12/2017 | Markowitz et al. |
| 2018/0119137 | A1* | 5/2018 | Matsuguchi ......... C12Q 1/6827 |
| 2018/0148777 | A1* | 5/2018 | Kirkizlar .............. C12Q 1/6869 |
| 2018/0245157 | A1 | 8/2018 | Allawi et al. |
| 2018/0251859 | A1 | 9/2018 | Ahlquist et al. |
| 2018/0258498 | A1 | 9/2018 | Ahlquist et al. |
| 2020/0377954 | A1 | 12/2020 | Bitenc et al. |

FOREIGN PATENT DOCUMENTS

| EP | 2497834 A2 | 9/2012 |
| EP | 2886659 A1 | 6/2015 |
| EP | 2977467 A2 | 1/2016 |
| WO | WO-02/081749 A2 | 10/2002 |
| WO | WO-2005/001142 A2 | 1/2005 |
| WO | WO-2010/118559 A1 | 10/2010 |
| WO | WO-2012/034170 A1 | 3/2012 |
| WO | WO-2012/047899 A2 | 4/2012 |
| WO | WO-2012/154979 A2 | 11/2012 |
| WO | WO-2012/167145 A2 | 12/2012 |
| WO | WO-2012/170715 A1 | 12/2012 |
| WO | WO-2013/057581 A2 | 4/2013 |
| WO | WO-2014/032227 A1 | 3/2014 |
| WO | WO-2015/153283 A1 | 10/2015 |
| WO | WO-2015/153284 A1 | 10/2015 |
| WO | WO-2015/159292 A2 | 10/2015 |
| WO | WO-2016/109782 A2 | 7/2016 |
| WO | WO-2017/012592 A1 | 1/2017 |
| WO | WO-2017/192221 A1 | 11/2017 |
| WO | WO-2017/212428 A1 | 12/2017 |
| WO | WO-2018/140781 A1 | 8/2018 |
| WO | WO-2018/195211 A1 | 10/2018 |
| WO | WO-2020/239895 A2 | 12/2020 |
| WO | WO-2020/239896 A1 | 12/2020 |

OTHER PUBLICATIONS

Kok Sin et al. (Oncology Reports, 2015, 34:22-32) (Year: 2015).*
Yang et al. (Medicine, 2017, 96:47, e8487, p. 1-7) (Year: 2017).*
DOE Joint Genome Institute (AC012313; Mar. 2003) (Year: 2003).*
Kutsenko et al. (Nucleic Acids Research, 2002, 30(14):3163-3170) (Year: 2002).*
DOE Joint Genome Institute (AC024563; Jul. 2002) (Year: 2002).*
Lowe et al. (Nucleic Acids Research, 1990, 18(7):1757-1761) (Year: 1990).*

(Continued)

*Primary Examiner* — Stephanie K Mummert
(74) *Attorney, Agent, or Firm* — William R. Haulbrook; Samuel R. Polio; Choate, Hall & Stewart LLP

(57) ABSTRACT

The present disclosure provides, among other things, methods for colorectal cancer detection (e.g., screening) and compositions related thereto. In various embodiments, the present disclosure provides methods for colorectal cancer screening that include analysis of methylation status of one or more methylation biomarkers, and compositions related thereto. In various embodiments, the present disclosure provides methods for colorectal cancer detection (e.g., screening) that include detecting (e.g., screening) methylation status of one or more methylation biomarkers in cfDNA, e.g., in ctDNA. In various embodiments, the present disclosure provides methods for colorectal cancer screening that include detecting (e.g., screening) methylation status of one or more methylation biomarkers in cfDNA, e.g., in ctDNA, using MSRE-qPCR.

12 Claims, 31 Drawing Sheets

Specification includes a Sequence Listing.

(56) References Cited

OTHER PUBLICATIONS

Fan, C.H.. et al., Noninvasive diagnosis of fetal aneuploidy by shotgun sequencing DNA from maternal blood, Proceedings of the National Academy of Sciences, 105(42):16266-16271 (2008).
Hemmasi, G., et al., Prevalence of colorectal adenoma in an average-risk population aged 40-50 versus 50-60 years, European Journal of Cancer Prevention (ECP), pp. 1-5, (2014).
Karsenti, D. et al., Adenoma and advanced neoplasia detection rates increase from 45 years of age, World Journal of Gastroenterology, 25(4): 447-456 (2019).
O'Connell B., and Crockett S., The clinical impact of serrated colorectal polyps, Dove Press Journal, Clinical Epidemiology, 9: 113-125 (2017).
Snyder, M.W. et al., Cell-free DNA Comprises an In vivo Nucleosome footprint that informs its Tissues-of-Origin, Cell, 164: pp. 57-68, (2016).
Aberle, D.R., et al., Reduced lung-cancer mortality with low-dose computed tomographic screening, National Lung Screening Trial Research Team, 365(5):395-409, (2011).
Andersson, I., et al., Mammographic screening and mortality from breast cancer: the Malmö mammographic screening trial, 297(6654): 943-8, (1988).
Breast Cancer Screening (PDQ®)—Health Professional Version, <https://www.cancer.gov/types/breast/hp/breast-screening-pdq#section/all>. Retrieved on Jul. 17, 2020.
Demissie, K., et al., Empirical comparison of the results of randomized controlled trials and case-control studies in evaluating the effectiveness of screening mammography, 51(2):81-91, (1998).
Krueger, F. and Andrews, S.R., Bismark: a flexible aligner and methylation caller for Bisulfite-Seq applications, Bioinformatics, 27(11):1571-2, (2011).
QIAamp® Circulating Nucleic Acid Handbook, For concentration and purification of free-circulating DNA, RNA, miRNA, and viral nucleic acids from human plasma, serum, urine, or other cell-free body fluids, Oct. 2019.
QIAamp® MinElute® ccfDNA Handbook, For concentration and purification of circulation cell-free DNA from plasma or serum, Jan. 2020.
Rahib, L., et. al., Projecting cancer incidence and deaths to 2030: the unexpected burden of thyroid, liver, and pancreas cancers in the United States, 74(11):2913-21, (2014).
The Cancer Genome Atlas Program, <https://www.cancer.gov/about-nci/organization/ccg/research/structural-genomics/tcga>.
Vainio, H., et al., IARC Handbooks of Cancer Prevention Programme Head: Harri Vainio. vol. 7: Breast Cancer Screening, pp. 1-236, (2002).
Adler, A. et al., Improving compliance to colorectal cancer screening using blood and stool based tests in patients refusing screening colonoscopy in Germany, BMC Gastroenterology, 14:183, (2014).
Beikircher, G. et al., Multiplexed and Sensitive DNA Methylation Testing Using Methylation-Sensitive Restriction Enzymes "MSRE-qPCR", DNA Methylation Protocols, Methods in Molecular Biology 1708:Ch21:407-424, (2018).
Bray, F. et al., Global Cancer Statistics 2018: GLOBOCAN Estimates of Incidence and Mortality Worldwide for 36 Cancers in 185 Countries, CA Cancer J Clin., 68:394-424, (2018).
Calderwood, A. H. et al., Colon adenoma features and their impact on risk of future advanced adenomas and colorectal cancer, World Journal of Gastrointestinal Oncology, 8(12):826-834, (2016).
Capman, M. et al., MethyLight and Digital MethyLight, DNA Methylation Protocols, Methods in Molecular Biology, 1708:CH25:497-513, (2018).
Chang, C. P.-Y. et al., Elevated cell-free serum DNA detected in patients with myocardial infarction, Clinica Chimica Acta 327:95-101, (2003).
Chen, Y. et al., Tissue-independent and tissue-specific patterns of DNA methylation alteration in cancer, Epigenetics & Chromatin, 9:10, (2016).

Chiu, R. W. K. et al., Noninvasive prenatal diagnosis of fetal chromosomal aneuploidy by massively parallel genomic sequencing of DNA in maternal plasma, PNAS, 105(51):20458-20463, (2008).
Esteller, M., CpG island hypermethylation and tumor suppressor genes: a booming present, a brighter future, Oncogene, 21:5427-5440, (2002).
Fackler, M. J. and Sukumar, S., Quantitation of DNA Methylation by Quantitative Multiplex Methylation-Specific PCR (QM-MSP) Assay, DNA Methylation Protocols, Methods in Molecular Biology, 1708:CH24:473-496, (2018).
Frommer, M. et al., A genomic sequencing protocol that yields a positive display of 5-methylcytosine residues in individual DNA strands, Proc. Natl. Acad. Sci. USA, 89:1827-1831, (1992).
Galeazzi, M. et al., Dosage and characterization of circulating DNA: present usage and possible applications in systemic autoimmune disorders, Autoimmunity Reviews, 2:50-55, (2003).
Gasc, C. et al., Survey and Summary: Sequence capture by hybridization to explore modern and ancient genomic diversity in model and nonmodel organisms, Nucleic Acids Research, 44(10):4504-4518, (2016).
Gonzalgo, M. L. and Liang, G., Methylation-sensitive single-nucleotide primer extension (Ms-SNuPE) for quantitative measurement of DNA methylation, Nature Protocols, 2(8):1931-1936, (2007).
Herman, J. G. et al., Methylation-specific PCR: A novel PCR assay for methylation status of CpG islands, Proc. Natl. Acad. Sci. USA, 93:9821-9826, (1996).
Hussmann, D. and Hansen, L. L., Methylation-Sensitive High Resolution Melting (MS-HRM), DNA Methylation Protocols, Methods in Molecular Biology, 1708:CH28:551-571, (2018).
Imperiale, T. F. et al., Multitarget Stool DNA Testing for Colorectal-Cancer Screening, Correspondence to the Editor, The New England Journal of Medicine, doi:10.1056/NEJMc1405215, 371(2):184-188, (2014).
Imperiale, T. F. et al., Multitarget Stool DNA Testing for Colorectal-Cancer Screening, The New England Journal of Medicine, 370(14):1287-1297, (2014).
Ivanov, M. et al., In-solution hybrid capture of bisulfite-converted DNA for targeted bisulfite sequencing of 174 ADME genes, Nucleic Acids Research, 46(6):e72, 9 pages, (2013).
Laird, P. W., Applications of Next-Generation Sequencing: Principles and challenges of genomewide DNA methylation analysis, Nature Review, Genetics, 11:191-203, (2010).
Leon, S. A. et al., Free DNA in the Serum of Cancer Patients and the Effect of Therapy, Cancer Research, 37:646-650, (1977).
Liles, E. G. et al., Uptake of a colorectal cancer screening blood test is higher than of a fecal test offered in clinic: A randomized trial, Cancer Treatment and Research Communications, 10:27-31, (2017).
Liu, Y. et al., Methylation-sensitive enrichment of minor DNA alleles using a double-strand DNA-specific nuclease, Nucleic Acids Research, 45(6):e39, 11 pages, (2017).
Masser, D. R. et al., Targeted DNA Methylation Analysis by Next-generation Sequencing, Journal of Visualized Experiments, www.jove.com, ©Creative Commons Attribution—NonCommercial License, 96:e52488, 11 pages, (2015).
Meyer, D. et al., Package 'e1071', Misc Functions of the Department of Statistics, Probability Theory Group (Formerly: E1071), Tu Wien, https://cran.r-project.org/web/packages/e1071/index.html, 63 pages, (2019).
Nakamura, A. et al., Relationship between sodium excretion and pioglitazone-induced edema, Journal of Diabetes Investigation, 1(5):208-211, (2010).
Navarro, M. et al., Colorectal cancer population screening programs worldwide in 2016: An Update, World J Gastroenterol, 23(20):3632-3642, (2017).
Oh, T. et al., Genome-Wide Identification and Validation of a Novel Methylation Biomarker, SDC2, for Blood-Based Detection of Colorectal Cancer, The Journal of Molecular Diagnostics, 15(4):498-507, (2013).
Potter, N. T. et al., Validation of a Real-Time PCR-Based Qualitative Assay for the Detection of Methylated SEPT9 DNA in Human Plasma, Clinical Chemistry, 60(9):1183-1191, (2014).

(56) References Cited

OTHER PUBLICATIONS

Schwarzenbach, H. et al., Cell-free nucleic acids as biomarkers in cancer patients, Nature Reviews / Cancer, 11:426-437, (2011).
Shaukat, A. et al., Long-Term Mortality after Screening for Colorectal Cancer, The New England Journal of Medicine, 369(12):1106-1114, (2013).
Singh, K. E. et al., Colorectal Cancer Incidence Among Young Adults in California, Journal of Adolescent and Young Adult Oncology, 3(4):176-184, (2014).
Swarup, V. and Rajeswari, M.R., Circulating (cell-free) nucleic acids—A promising, non-invasive tool for early detection of several human diseases, FEBS Letters 581:795-799, (2007).
Van Der Vlugt, M. et al., Adherence to colorectal cancer screening: four rounds of faecal immunochemical test-based screening, British Journal of Cancer, 116(1):44-49, (2017).
Wittenberger, T. et al., DNA methylation markers for early detection of women's cancer: promise and challenges, Epigenomics, 6(3):311-327, (2014).
Galanopoulos, M., et. al., Abnormal DNA methylation as a cell-free circulating DNA biomarker for colorectal cancer detection: A review of literature, World Journal of Gastrointestinal Oncology, 9(4):142-152, (2017).
International Search Report for PCT/EP2020/064815 filed May 28, 2020, 6 pages, (Apr. 9, 2020).
Kordowski., F., et al., Aberrant DNA methylation of ADAMTS16 in colorectal and other epithlial cancers, BMC Cancer, 18(1):4, (2018).
Kruusmaa, K. et. al., MSRE-qPCR for analysis of gene specific methylation can be accurately used for detection and validation of colorectal cancer-specific patterns, 4Bio Summit (Jan. 1, 2018). <www.universaldx.com/wp-content/uploads/2017/05/4Bio-poster-November-2018.pdf>. Retrieved on Aug. 19, 2020.
Melnikov, A. A., et. al., MSRE-PCR for analysis of gene-specific DNA methylation, Nucleic Acids Research, 33(10): e93-e93, (2015).
Written Opinion for PCT/EP2020/064815 filed May 28, 2020, 6 pages, (dated Apr. 9, 2020).
Yan, H., et. al., Identifying CpG sites with different differential methylation frequencies in colorectal cancer tissues based on individualized differential methylation analysis, Open Access Impact Journal, 29(8): 47356-47364, (2017).
Chen, J. et. al., DNA methylation biomarkers in stool for early screening of colorectal cancer, Journal of Cancer,10(21):5264-5271, (2019).
Chen, J.J., et. al., DNA methylation assay for colorectal carcinoma, Cancer Biology & Medicine, 14(1):42-49, (2017).
International Search Report for PCT/EP2020/064813 filed May 28, 2020, 8 pages, (dated Dec. 22, 2020).
Mitchell, S.M. et. al., A panel of genes methylated with high frequency in colorectal cancer, BMC cancer biomed central, 14(1): 54, (2014).
Written Opinion for PCT/EP2020/064813 filed May 28, 2020, 13 pages, (dated Dec. 22, 2020).

\* cited by examiner

| | CRC | Training (n = 70) | | |
|---|---|---|---|---|
| | | Healthy + Non-Advanced Adenoma | Healthy | Non-advanced Adenoma |
| Female (%) | 15 (21.4) | 20 (28.6) | 15 (21.4) | 5 (7.1) |
| Male (%) | 15 (21.4) | 20 (28.6) | 15 (21.4) | 5 (7.1) |
| Age (Range) | 64 (41-80) | 60 (46-84) | 60 (46-77) | 60 (48-84) |
| BMI (sd) | 25.0 (±4.4) | 26.7 (±4.3) | 26.7 (±4.7) | 27.2 (±3.0) |
| | CRC All | Proximal | Distal | |
| Localized | 17 | 6 | 11 | |
| Advanced | 13 | 9 | 4 | |

Fig. 2

| | CRC | Validation (n = 63) | | Non-advanced Adenoma |
| --- | --- | --- | --- | --- |
| | | Healthy + Non-Advanced Adenoma | Healthy | |
| Female (%) | 11 (17.5) | 25 (39.7) | 20 (31.7) | 5 (7.9) |
| Male (%) | 9 (14.3) | 18 (28.6) | 11 (17.5) | 7 (11.1) |
| Age (Range) | 61 (45-84) | 57 (47-80) | 55 (47-80) | 63 (55-70) |
| BMI (sd) | 25.4 (± 3.8) | 26.3 (± 4.0) | 26.3 (± 4.0) | 26.7 (± 4.0) |
| | CRC All | Proximal | Distal | |
| Localized | 13 | 5 | 8 | |
| Advanced | 7 | 4 | 3 | |

Fig. 3

| | CRC | Control + NAA | Control | NAA |
|---|---|---|---|---|
| Validation= 82 Samples | | | | |
| Female | 20 | 14 | 11 | 3 |
| Male | 23 | 25 | 19 | 6 |
| Age (Range) | 63 (36-84) | 65 (45-83) | 64 (45-79) | 66 (55-83) |
| BMI (sd) | 27.2 (± 5) | 26.04 (± 3.3) | 26 (± 3.4) | 27.5 (± 2.5) |
| | CRC All | Proximal | Distal | |
| Localized | 24 | 12 | 12 | |
| Advanced | 19 | 9 | 10 | |

Fig. 10

Training Set

| | CRC | Healthy + NAA | Healthy | NAA |
|---|---|---|---|---|
| Female | 46 | 59 | 46 | 13 |
| Male | 47 | 63 | 45 | 18 |
| Age (Range) | 63(36-84) | 61(45-84) | 61(45-80) | 63(48-84) |
| Total | 93 | 122 | 91 | 31 |

Total sample 215

| | CRC All | Proximal | Distal |
|---|---|---|---|
| Localized | 54 | 23 | 31 |
| Advanced | 39 | 22 | 17 |
| Total | 93 | 45 | 48 |

Fig. 21

Validation Set

| | CRC | Healthy | NAA | Breast Cancer | Lung Cancer | Control (NAA+Healthy +Lung Cancer +Breast Cancer) |
|---|---|---|---|---|---|---|
| Female | 71 | 223 | 73 | 26 | 6 | 328 |
| Male | 81 | 199 | 75 | 0 | 20 | 294 |
| Age (range) | 65 (41-84) | 61 (41-82) | 66 (50-82) | 55 (41-77) | 61 (48-75) | 61 (41-82) |
| Total | 152 | 422 | 148 | 26 | 26 | 622 |
| Total samples | 774 | | | | | |

| | CRC All | Breast Cancer | Lung Cancer |
|---|---|---|---|
| Localized | 86 | 24 | 19 |
| Advanced | 62 | 2 | 6 |
| Unknown | 4 | 0 | 1 |
| Total | 152 | 26 | 26 |

Fig. 22

DETECTION OF COLORECTAL CANCER

CROSS REFERENCE TO RELATED APPLICATIONS

This application claims the benefit of U.S. application Ser. No. 16/428,865 filed on May 31, 2019, and U.S. Provisional Application No. 62/956,059, filed Dec. 31, 2019, the disclosure of each of which is hereby incorporated by reference in its entirety.

SEQUENCE LISTING

The instant application contains a Sequence Listing which has been filed electronically in ASCII format and is hereby incorporated by reference in its entirety. Said ASCII copy is named 2011722_0045_SL.txt and is 2,771,268 bytes in size.

BACKGROUND

Cancer screening is a critical component of cancer prevention, diagnosis, and treatment. Colorectal cancer (CRC) has been identified, according to some reports, as the third most common type of cancer and the second most frequent cause of cancer mortality in the world. According to some reports, there are over 1.8 million new cases of colorectal cancer per year and about 881,000 deaths from colorectal cancer, accounting for about 1 in 10 cancer deaths. Regular colorectal cancer screening is recommended, particular for individuals over age 50. Moreover, incidence of colorectal cancer in individuals below 50 has increased over time. Statistics suggest that current colorectal cancer screening techniques are insufficient.

SUMMARY

Despite improvements over time, only about 40-44% of colorectal cancers are currently detected by screening in an early, localized stage. This is at least in part due to insufficient sensitivity and/or specificity of current screening techniques. Currently recommended techniques include colonoscopy and/or fecal blood testing for those over age 50.

The present disclosure provides, among other things, methods for colorectal cancer screening and compositions related thereto. In various embodiments, the present disclosure provides methods for colorectal cancer screening that include determination of methylation status (e.g., the number, frequency, or pattern of methylation) at one or more methylation sites found within a methylation locus, e.g., a differentially methylated region (DMR), of deoxyribonucleic acid (DNA) of a human subject, and compositions related thereto. In various embodiments, the present disclosure provides methods for colorectal cancer screening that include screening methylation status for each of one or more methylation loci in cfDNA (cell free DNA), e.g., in ctDNA (circulating tumor DNA). In various embodiments, the present disclosure provides methods for colorectal cancer screening that include determining a methylation status for each of one or more methylation loci in cfDNA, e.g., in ctDNA, using quantitative polymerase chain reaction (qPCR) (e.g., methylation sensitive restriction enzyme quantitative polymerase chain reaction, MSRE-qPCR). Various compositions and methods provided herein provide sensitivity and specificity sufficient for clinical application in colorectal cancer screening. Various compositions and methods provided herein are useful in colorectal cancer screening by analysis of an accessible tissue sample of a subject, e.g., a tissue sample that is blood or a blood component (e.g., cfDNA, e.g., ctDNA), or stool.

In one aspect, the invention is directed to a method of detecting (e.g., screening for) colorectal cancer, the method comprising: determining a methylation status [e.g., a number, frequency, or pattern of methylation at one or more methylation sites within a methylation locus] for each of the following, in deoxyribonucleic acid (DNA) of a human subject: (a) a methylation locus [e.g., a differentially methylated region] within gene ZNF132; (b) a first methylation locus within gene ADAMTS2; and (c) a second methylation locus within gene ADAMTS2; and diagnosing colorectal cancer in the human subject based on said determined methylation statuses.

In certain embodiments, the method further comprises determining a methylation status for each of the following, in the DNA of the human subject: (d) a methylation locus within gene ZNF542; and (e) a methylation locus within gene LONRF2.

In certain embodiments, the method further comprises determining a methylation status for a methylation locus within gene ZNF492 in the DNA of the human subject.

In certain embodiments, the methylation locus within gene ZNF132 comprises ZNF132 '415 (SEQ ID NO: 40).

In certain embodiments, the first methylation locus within gene ADAMTS2 comprises ADAMTS2 '254 (SEQ ID NO: 21).

In certain embodiments, the second methylation locus within gene ADAMTS2 comprises ADAMTS2 '284 (SEQ ID NO: 22).

In certain embodiments, the methylation locus within gene ZNF542 comprises ZNF542 '502 (SEQ ID NO: 35).

In certain embodiments, the methylation locus within gene LONRF2 comprises LONRF2 '281 (SEQ ID NO: 19).

In certain embodiments, the methylation locus within gene ZNF492 comprises ZNF492 '069 (SEQ ID NO: 42).

In certain embodiments, the DNA is isolated from blood or plasma of the human subject.

In certain embodiments, the DNA is cell-free DNA of the human subject.

In certain embodiments, methylation status is determined using quantitative polymerase chain reaction (qPCR) (e.g., methylation sensitive restriction enzyme quantitative polymerase chain reaction, MSRE-qPCR).

In another aspect, the invention is directed to a kit for use in colorectal cancer detection (e.g., screening), the kit comprising: (a) an oligonucleotide primer pair for amplification of a methylation locus within gene ZNF132; (b) an oligonucleotide primer pair for amplification of a first methylation locus within gene ADAMTS2; and (c) an oligonucleotide primer pair for amplification of a second methylation locus within gene ADAMTS2 (e.g., and, optionally, the kit further comprising at least one methylation sensitive restriction enzyme).

In certain embodiments, the kit further comprises: (d) an oligonucleotide primer pair for amplification of a methylation locus within gene ZNF542; and (e) an oligonucleotide primer pair for amplification of a methylation locus within gene LONRF2.

In certain embodiments, the kit further comprises: (f) an oligonucleotide primer pair for amplification of a methylation locus within gene ZNF492.

In certain embodiments, (a) is an oligonucleotide primer pair for amplification of ZNF132 '415 (primer pair SEQ ID NO: 91 and SEQ ID NO: 92).

In certain embodiments, (b) is an oligonucleotide primer pair for amplification of ADAMTS2 '254 (primer pair SEQ ID NO: 53 and SEQ ID NO: 54).

In certain embodiments, (c) is an oligonucleotide primer pair for amplification of ADAMTS2 '284 (primer pair SEQ ID NO: 55 and SEQ ID NO: 56).

In certain embodiments, (d) is an oligonucleotide primer pair for amplification of ZNF542 '502 (primer pair SEQ ID NO: 81 and SEQ ID NO: 82).

In certain embodiments, (e) is an oligonucleotide primer pair for amplification of LONRF2 '281 (primer pair SEQ ID NO: 49 and SEQ ID NO: 50).

In certain embodiments, (f) is an oligonucleotide primer pair for amplification of ZNF492 '069 (primer pair SEQ ID NO: 95 and SEQ ID NO: 96).

In another aspect, the invention is directed to a diagnostic qPCR reaction for detection (e.g., screening) of colorectal cancer, the diagnostic qPCR reaction including: (a) human DNA; (b) a polymerase; (c) an oligonucleotide primer pair for amplification of a methylation locus within gene ZNF132; (d) an oligonucleotide primer pair for amplification of a first methylation locus within gene ADAMTS2; (e) an oligonucleotide primer pair for amplification of a second methylation locus within gene ADAMTS2; and (f) optionally, at least one methylation sensitive restriction enzyme.

In certain embodiments, the reaction further comprises: (g) an oligonucleotide primer pair for amplification of a methylation locus within gene ZNF542; and (h) an oligonucleotide primer pair for amplification of a methylation locus within gene LONRF2.

In certain embodiments, the reaction further comprises: (i) an oligonucleotide primer pair for amplification of a methylation locus within gene ZNF492.

In certain embodiments, (c) is an oligonucleotide primer pair for amplification of ZNF132 '415 (primer pair SEQ ID NO: 91 and SEQ ID NO: 92).

In certain embodiments, (d) is an oligonucleotide primer pair for amplification of ADAMTS2 '254 (primer pair SEQ ID NO: 53 and SEQ ID NO: 54).

In certain embodiments, (e) is an oligonucleotide primer pair for amplification of ADAMTS2 '284 (primer pair SEQ ID NO: 55 and SEQ ID NO: 56).

In certain embodiments, (g) is an oligonucleotide primer pair for amplification of ZNF542 '502 (primer pair SEQ ID NO: 81 and SEQ ID NO: 82).

In certain embodiments, (h) is an oligonucleotide primer pair for amplification of LONRF2 '281 (primer pair SEQ ID NO: 49 and SEQ ID NO: 50).

In certain embodiments, (i) is an oligonucleotide primer pair for amplification of ZNF492 '069 (primer pair SEQ ID NO: 95 and SEQ ID NO: 96).

In various aspects, methods and compositions of the present invention can be used in combination with biomarkers known in the art, e.g., as disclosed in U.S. Pat. No. 10,006,925, which is herein incorporated by reference in its entirety.

Definitions

A or An: The articles "a" and "an" are used herein to refer to one or to more than one (i.e., to at least one) of the grammatical object of the article. By way of example, "an element" refers to one element or more than one element.

About: The term "about", when used herein in reference to a value, refers to a value that is similar, in context, to the referenced value. In general, those skilled in the art, familiar with the context, will appreciate the relevant degree of variance encompassed by "about" in that context. For example, in some embodiments, e.g., as set forth herein, the term "about" can encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or with a fraction of a percent, of the referred value.

Administration: As used herein, the term "administration" typically refers to the administration of a composition to a subject or system, for example to achieve delivery of an agent that is, is included in, or is otherwise delivered by, the composition.

Agent: As used herein, the term "agent" refers to an entity (e.g., for example, a small molecule, peptide, polypeptide, nucleic acid, lipid, polysaccharide, complex, combination, mixture, system, or phenomenon such as heat, electric current, electric field, magnetic force, magnetic field, etc.).

Amelioration: As used herein, the term "amelioration" refers to the prevention, reduction, palliation, or improvement of a state of a subject. Amelioration includes, but does not require, complete recovery or complete prevention of a disease, disorder or condition.

Amplicon or amplicon molecule: As used herein, the term "amplicon" or "amplicon molecule" refers to a nucleic acid molecule generated by transcription from a template nucleic acid molecule, or a nucleic acid molecule having a sequence complementary thereto, or a double-stranded nucleic acid including any such nucleic acid molecule. Transcription can be initiated from a primer.

Amplification: As used herein, the term "amplification" refers to the use of a template nucleic acid molecule in combination with various reagents to generate further nucleic acid molecules from the template nucleic acid molecule, which further nucleic acid molecules may be identical to or similar to (e.g., at least 70% identical, e.g., at least 75%, 80%, 85%, 90%, 91%, 92%, 93%, 94%, 95%, 96%, 97%, 98%, 99%, or 100% identical to) a segment of the template nucleic acid molecule and/or a sequence complementary thereto.

Amplification reaction mixture: As used herein, the terms "amplification reaction mixture" or "amplification reaction" refer to a template nucleic acid molecule together with reagents sufficient for amplification of the template nucleic acid molecule.

Biological Sample: As used herein, the term "biological sample" typically refers to a sample obtained or derived from a biological source (e.g., a tissue or organism or cell culture) of interest, as described herein. In some embodiments, e.g., as set forth herein, a biological source is or includes an organism, such as an animal or human. In some embodiments, e.g., as set forth herein, a biological sample is or include biological tissue or fluid. In some embodiments, e.g., as set forth herein, a biological sample can be or include cells, tissue, or bodily fluid. In some embodiments, e.g., as set forth herein, a biological sample can be or include blood, blood cells, cell-free DNA, free floating nucleic acids, ascites, biopsy samples, surgical specimens, cell-containing body fluids, sputum, saliva, feces, urine, cerebrospinal fluid, peritoneal fluid, pleural fluid, lymph, gynecological fluids, secretions, excretions, skin swabs, vaginal swabs, oral swabs, nasal swabs, washings or lavages such as a ductal lavages or broncheoalveolar lavages, aspirates, scrapings, bone marrow. In some embodiments, e.g., as set forth herein, a biological sample is or includes cells obtained from a single subject or from a plurality of subjects. A sample can be a "primary sample" obtained directly from a biological source, or can be a "processed sample." A biological sample can also be referred to as a "sample."

Biomarker: As used herein, the term "biomarker," consistent with its use in the art, refers to a to an entity whose presence, level, or form, correlates with a particular biological event or state of interest, so that it is considered to be a "marker" of that event or state. Those of skill in the art will appreciate, for instance, in the context of a DNA biomarker, that a biomarker can be or include a locus (such as one or more methylation loci) and/or the status of a locus (e.g., the status of one or more methylation loci). To give but a few examples of biomarkers, in some embodiments, e.g., as set forth herein, a biomarker can be or include a marker for a particular disease, disorder or condition, or can be a marker for qualitative of quantitative probability that a particular disease, disorder or condition can develop, occur, or reoccur, e.g., in a subject. In some embodiments, e.g., as set forth herein, a biomarker can be or include a marker for a particular therapeutic outcome, or qualitative of quantitative probability thereof. Thus, in various embodiments, e.g., as set forth herein, a biomarker can be predictive, prognostic, and/or diagnostic, of the relevant biological event or state of interest. A biomarker can be an entity of any chemical class. For example, in some embodiments, e.g., as set forth herein, a biomarker can be or include a nucleic acid, a polypeptide, a lipid, a carbohydrate, a small molecule, an inorganic agent (e.g., a metal or ion), or a combination thereof. In some embodiments, e.g., as set forth herein, a biomarker is a cell surface marker. In some embodiments, e.g., as set forth herein, a biomarker is intracellular. In some embodiments, e.g., as set forth herein, a biomarker is found outside of cells (e.g., is secreted or is otherwise generated or present outside of cells, e.g., in a body fluid such as blood, urine, tears, saliva, cerebrospinal fluid, and the like). In some embodiments, e.g., as set forth herein, a biomarker is methylation status of a methylation locus. In some instances, e.g., as set forth herein, a biomarker may be referred to as a "marker."

To give but one example of a biomarker, in some embodiments e.g., as set forth herein, the term refers to expression of a product encoded by a gene, expression of which is characteristic of a particular tumor, tumor subclass, stage of tumor, etc. Alternatively or additionally, in some embodiments, e.g., as set forth herein, presence or level of a particular marker can correlate with activity (or activity level) of a particular signaling pathway, for example, of a signaling pathway the activity of which is characteristic of a particular class of tumors.

Those of skill in the art will appreciate that a biomarker may be individually determinative of a particular biological event or state of interest, or may represent or contribute to a determination of the statistical probability of a particular biological event or state of interest. Those of skill in the art will appreciate that markers may differ in their specificity and/or sensitivity as related to a particular biological event or state of interest.

Blood component: As used herein, the term "blood component" refers to any component of whole blood, including red blood cells, white blood cells, plasma, platelets, endothelial cells, mesothelial cells, epithelial cells, and cell-free DNA. Blood components also include the components of plasma, including proteins, metabolites, lipids, nucleic acids, and carbohydrates, and any other cells that can be present in blood, e.g., due to pregnancy, organ transplant, infection, injury, or disease.

Cancer: As used herein, the terms "cancer," "malignancy," "neoplasm," "tumor," and "carcinoma," are used interchangeably to refer to a disease, disorder or condition in which cells exhibit or exhibited relatively abnormal, uncontrolled, and/or autonomous growth, so that they display or displayed an abnormally elevated proliferation rate and/or aberrant growth phenotype. In some embodiments, e.g., as set forth herein, a cancer can include one or more tumors. In some embodiments e.g., as set forth herein, a cancer can be or include cells that are precancerous (e.g., benign), malignant, pre-metastatic, metastatic, and/or non-metastatic. In some embodiments e.g., as set forth herein, a cancer can be or include a solid tumor. In some embodiments e.g., as set forth herein, a cancer can be or include a hematologic tumor. In general, examples of different types of cancers known in the art include, for example, colorectal cancer, hematopoietic cancers including leukemias, lymphomas (Hodgkin's and non-Hodgkin's), myelomas and myeloproliferative disorders; sarcomas, melanomas, adenomas, carcinomas of solid tissue, squamous cell carcinomas of the mouth, throat, larynx, and lung, liver cancer, genitourinary cancers such as prostate, cervical, bladder, uterine, and endometrial cancer and renal cell carcinomas, bone cancer, pancreatic cancer, skin cancer, cutaneous or intraocular melanoma, cancer of the endocrine system, cancer of the thyroid gland, cancer of the parathyroid gland, head and neck cancers, breast cancer, gastro-intestinal cancers and nervous system cancers, benign lesions such as papillomas, and the like.

Chemotherapeutic agent: As used herein, the term "chemotherapeutic agent," consistent with its use in the art, refers to one or more agents known, or having characteristics known to, treat or contribute to the treatment of cancer. In particular, chemotherapeutic agents include pro-apoptotic, cytostatic, and/or cytotoxic agents. In some embodiments e.g., as set forth herein, a chemotherapeutic agent can be or include alkylating agents, anthracyclines, cytoskeletal disruptors (e.g., microtubule targeting moieties such as taxanes, maytansine, and analogs thereof, of), epothilones, histone deacetylase inhibitors HDACs), topoisomerase inhibitors (e.g., inhibitors of topoisomerase I and/or topoisomerase II), kinase inhibitors, nucleotide analogs or nucleotide precursor analogs, peptide antibiotics, platinum-based agents, retinoids, *vinca* alkaloids, and/or analogs that share a relevant anti-proliferative activity. In some particular embodiments e.g., as set forth herein, a chemotherapeutic agent can be or include of Actinomycin, All-trans retinoic acid, an Auiristatin, Azacitidine, Azathioprine, Bleomycin, Bortezomib, Carboplatin, Capecitabine, Cisplatin, Chlorambucil, Cyclophosphamide, Curcumin, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Maytansine and/or analogs thereof (e.g., DM1) Mechlorethamine, Mercaptopurine, Methotrexate, Mitoxantrone, a Maytansinoid, Oxaliplatin, Paclitaxel, Pemetrexed, Teniposide, Tioguanine, Topotecan, Valrubicin, Vinblastine, Vincristine, Vindesine, Vinorelbine, or a combination thereof. In some embodiments e.g., as set forth herein, a chemotherapeutic agent can be utilized in the context of an antibody-drug conjugate. In some embodiments e.g., as set forth herein, a chemotherapeutic agent is one found in an antibody-drug conjugate selected from the group consisting of: hLL1-doxorubicin, hRS7-SN-38, hMN-14-SN-38, hLL2-SN-38, hA20-SN-38, hPAM4-SN-38, hLL1-SN-38, hRS7-Pro-2-P-Dox, hMN-14-Pro-2-P-Dox, hLL2-Pro-2-P-Dox, hA20-Pro-2-P-Dox, hPAM4-Pro-2-P-Dox, hLL1-Pro-2-P-Dox, P4/D10-doxorubicin, gemtuzumab ozogamicin, brentuximab vedotin, trastuzumab emtansine, inotuzumab ozogamicin, glembatumomab vedotin, SAR3419, SAR566658, BIIB015, BT062, SGN-75, SGN-CD19A, AMG-172, AMG-595, BAY-94-9343, ASG-5ME, ASG-22ME, ASG-16M8F, MDX-1203, MLN-0264, anti-PSMA ADC, RG-7450, RG-7458, RG-7593, RG-7596, RG-7598, RG-7599, RG-7600, RG-7636, ABT-414, IMGN-853, IMGN-529, vorsetuzumab mafodotin, and lorvotuzumab mertansine. In some embodiments e.g., as set forth herein, a chemotherapeutic agent can be or comprise of farnesyl-thiosalicylic acid (FTS), 4-(4-Chloro-2-methylphenoxy)-N-hydroxybutanamide (CMH), estradiol (E2), tetramethoxystilbene (TMS), δ-tocatrienol, salinomycin, or curcumin.

Combination therapy: As used herein, the term "combination therapy" refers to administration to a subject of to two or more agents or regimens such that the two or more agents or regimens together treat a disease, condition, or disorder of the subject. In some embodiments, e.g., as set forth herein, the two or more therapeutic agents or regimens can be administered simultaneously, sequentially, or in overlapping dosing regimens. Those of skill in the art will appreciate that combination therapy includes but does not require that the two agents or regimens be administered together in a single composition, nor at the same time.

Comparable: As used herein, the term "comparable" refers to members within sets of two or more conditions, circumstances, agents, entities, populations, etc., that may not be identical to one another but that are sufficiently similar to permit comparison there between, such that one of skill in the art will appreciate that conclusions can reasonably be drawn based on differences or similarities observed. In some embodiments, e.g., as sort forth herein, comparable sets of conditions, circumstances, agents, entities, populations, etc. are typically characterized by a plurality of substantially identical features and zero, one, or a plurality of differing features. Those of ordinary skill in the art will understand, in context, what degree of identity is required to render members of a set comparable. For example, those of ordinary skill in the art will appreciate that members of sets of conditions, circumstances, agents, entities, populations, etc., are comparable to one another when characterized by a sufficient number and type of substantially identical features to warrant a reasonable conclusion that differences observed can be attributed in whole or part to non-identical features thereof.

Detectable moiety: The term "detectable moiety" as used herein refers to any element, molecule, functional group, compound, fragment, or other moiety that is detectable. In some embodiments, e.g., as sort forth herein, a detectable moiety is provided or utilized alone. In some embodiments, e.g., as sort forth herein, a detectable moiety is provided and/or utilized in association with (e.g., joined to) another agent. Examples of detectable moieties include, but are not limited to, various ligands, radionuclides (e.g., $^{3}H$, $^{14}C$, $^{18}F$, $^{19}F$, $^{32}P$, $^{35}S$, $^{135}I$, $^{125}I$, $^{123}I$, $^{64}Cu$, $^{187}Re$, $^{111}In$, $^{90}Y$, $^{99m}Tc$, $^{177}Lu$, $^{89}Zr$ etc.), fluorescent dyes, chemiluminescent agents, bioluminescent agents, spectrally resolvable inorganic fluorescent semiconductors nanocrystals (i.e., quantum dots), metal nanoparticles, nanoclusters, paramagnetic metal ions, enzymes, colorimetric labels, biotin, dioxigenin, haptens, and proteins for which antisera or monoclonal antibodies are available.

Diagnosis: As used herein, the term "Diagnosis" refers to determining whether, and/or the qualitative of quantitative probability that, a subject has or will develop a disease, disorder, condition, or state. For example, in diagnosis of cancer, diagnosis can include a determination regarding the risk, type, stage, malignancy, or other classification of a cancer. In some instances, e.g., as sort forth herein, a diagnosis can be or include a determination relating to prognosis and/or likely response to one or more general or particular therapeutic agents or regimens.

Diagnostic information: As used herein, the term "diagnostic information" refers to information useful in providing a diagnosis. Diagnostic information can include, without limitation, biomarker status information.

Differentially methylated: As used herein, the term "differentially methylated" describes a methylation site for which the methylation status differs between a first condition and a second condition. A methylation site that is differentially methylated can be referred to as a differentially methylated site. In some instances, e.g., as sort forth herein, a DMR is defined by the amplicon produced by amplification using oligonucleotide primers, e.g., a pair of oligonucleotide primers selected for amplification of the DMR or for amplification of a DNA region of interest present in the amplicon. In some instances, e.g., as sort forth herein, a DMR is defined as a DNA region amplified by a pair of oligonucleotide primers, including the region having the sequence of, or a sequence complementary to, the oligonucleotide primers. In some instances, e.g., as sort forth herein, a DMR is defined as a DNA region amplified by a pair of oligonucleotide primers, excluding the region having the sequence of, or a sequence complementary to, the oligonucleotide primers. As used herein, a specifically provided DMR can be unambiguously identified by the name of an associated gene followed by three digits of a starting position, such that, for example, a DMR starting at position 29921434 of ALK can be identified as ALK '434.

Differentially methylated region: As used herein, the term "differentially methylated region" (DMR) refers to a DNA region that includes one or more differentially methylated sites. A DMR that includes a greater number or frequency of methylated sites under a selected condition of interest, such as a cancerous state, can be referred to as a hypermethylation DMR. A DMR that includes a smaller number or frequency of methylated sites under a selected condition of interest, such as a cancerous state, can be referred to as a hypomethylation DMR. A DMR that is a methylation biomarker for colorectal cancer can be referred to as a colorectal cancer DMR. In some instances, e.g., as set forth herein, a DMR can be a single nucleotide, which single nucleotide is a methylation site. In some instances, e.g., as set forth herein, a DMR has a length of at least 10, at least 15, at least 20, at least 24, at least 50, or at least 75 base pairs. In some instances, e.g., as set forth herein, a DMR has a length of less than 1000, less than 750, less than 500, less than 350, less than 300, or less than 250 base pairs (e.g., where methylation status is determined using quantitative polymerase chain reaction (qPCR), e.g., methylation sensitive restriction enzyme quantitative polymerase chain reaction (MSRE-qPCR)). In some instances, e.g., as set forth herein, a DMR that is a methylation biomarker for advanced adenoma may also be useful in identification of colorectal cancer.

DNA region: As used herein, "DNA region" refers to any contiguous portion of a larger DNA molecule. Those of skill in the art will be familiar with techniques for determining whether a first DNA region and a second DNA region correspond, based, e.g., on sequence similarity (e.g, sequence identity or homology) of the first and second DNA regions and/or context (e.g., the sequence identity or homology of nucleic acids upstream and/or downstream of the first and second DNA regions).

Except as otherwise specified herein, sequences found in or relating to humans (e.g., that hybridize to human DNA) are found in, based on, and/or derived from the example representative human genome sequence commonly referred to, and known to those of skill in the art, as *Homo sapiens* (human) genome assembly GRCh38, hg38, and/or Genome Reference Consortium Human Build 38. Those of skill in the art will further appreciate that DNA regions of hg38 can be referred to by a known system including identification of particular nucleotide positions or ranges thereof in accordance with assigned numbering.

Dosing regimen: As used herein, the term "dosing regimen" can refer to a set of one or more same or different unit doses administered to a subject, typically including a plurality of unit doses administration of each of which is separated from administration of the others by a period of time. In various embodiments, e.g., as set forth herein, one or more or all unit doses of a dosing regimen may be the same or can vary (e.g., increase over time, decrease over time, or be adjusted in accordance with the subject and/or with a medical practitioner's determination). In various embodiments, e.g., as set forth herein, one or more or all of the periods of time between each dose may be the same or can vary (e.g., increase over time, decrease over time, or be adjusted in accordance with the subject and/or with a medical practitioner's determination). In some embodiments, e.g., as set forth herein, a given therapeutic agent has a recommended dosing regimen, which can involve one or more doses. Typically, at least one recommended dosing regimen of a marketed drug is known to those of skill in the art. In some embodiments, e.g., as set forth herein, a dosing regimen is correlated with a desired or beneficial outcome when administered across a relevant population (i.e., is a therapeutic dosing regimen).

Downstream: As used herein, the term "downstream" means that a first DNA region is closer, relative to a second DNA region, to the C-terminus of a nucleic acid that includes the first DNA region and the second DNA region.

Gene: As used herein, the term "gene" refers to a single DNA region, e.g., in a chromosome, that includes a coding sequence that encodes a product (e.g., an RNA product and/or a polypeptide product), together with all, some, or none of the DNA sequences that contribute to regulation of the expression of coding sequence. In some embodiments, e.g., as set forth herein, a gene includes one or more non-coding sequences. In some particular embodiments, e.g., as set forth herein, a gene includes exonic and intronic sequences. In some embodiments, e.g., as set forth herein, a gene includes one or more regulatory elements that, for example, can control or impact one or more aspects of gene expression (e.g., cell-type-specific expression, inducible expression, etc.). In some embodiments, e.g., as set forth herein, a gene includes a promoter. In some embodiments, e.g., as set forth herein, a gene includes one or both of a (i) DNA nucleotides extending a predetermined number of nucleotides upstream of the coding sequence and (ii) DNA nucleotides extending a predetermined number of nucleotides downstream of the coding sequence. In various embodiments, e.g., as set forth herein, the predetermined number of nucleotides can be 500 bp, 1 kb, 2 kb, 3 kb, 4 kb, 5 kb, 10 kb, 20 kb, 30 kb, 40 kb, 50 kb, 75 kb, or 100 kb.

Homology: As used herein, the term "homology" refers to the overall relatedness between polymeric molecules, e.g., between nucleic acid molecules (e.g., DNA molecules and/or RNA molecules) and/or between polypeptide molecules. Those of skill in the art will appreciate that homology can be defined, e.g., by a percent identity or by a percent homology (sequence similarity). In some embodiments, e.g., as set forth herein, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, e.g., as set forth herein, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar.

Hybridize: As used herein, "hybridize" refers to the association of a first nucleic acid with a second nucleic acid to form a double-stranded structure, which association occurs through complementary pairing of nucleotides. Those of skill in the art will recognize that complementary sequences, among others, can hybridize. In various embodiments, e.g., as set forth herein, hybridization can occur, for example, between nucleotide sequences having at least 70% complementarity, e.g., at least 75%, 80%, 85%, 90%, 91%, 92%, 93%, 94%, 95%, 96%, 97%, 98%, 99%, or 100% complementarity. Those of skill in the art will further appreciate that whether hybridization of a first nucleic acid and a second nucleic acid does or does not occur can dependence upon various reaction conditions. Conditions under which hybridization can occur are known in the art.

Hypomethylation: As used herein, the term "hypomethylation" refers to the state of a methylation locus having at least one fewer methylated nucleotides in a state of interest as compared to a reference state (e.g., at least one fewer methylated nucleotides in colorectal cancer than in healthy control).

Hypermethylation: As used herein, the term "hypermethylation" refers to the state of a methylation locus having at least one more methylated nucleotide in a state of interest as compared to a reference state (e.g., at least one more methylated nucleotide in colorectal cancer than in healthy control).

Identity, identical: As used herein, the terms "identity" and "identical" refers to the overall relatedness between polymeric molecules, e.g., between nucleic acid molecules (e.g., DNA molecules and/or RNA molecules) and/or between polypeptide molecules. Methods for the calculation of a percent identity as between two provided sequences are known in the art. Calculation of the percent identity of two nucleic acid or polypeptide sequences, for example, can be performed by aligning the two sequences (or the complement of one or both sequences) for optimal comparison purposes (e.g., gaps can be introduced in one or both of a first and a second sequences for optimal alignment and non-identical sequences can be disregarded for comparison purposes). The nucleotides or amino acids at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences and, optionally, taking into account the number of gaps and the length of each gap, which may need to be introduced for optimal alignment of the two sequences. The comparison of sequences and determination of percent identity between two sequences can be accomplished using a computational algorithm, such as BLAST (basic local alignment search tool).

"Improved," "increased," or "reduced": As used herein, these terms, or grammatically comparable comparative terms, indicate values that are relative to a comparable reference measurement. For example, in some embodiments, e.g., as set forth herein, an assessed value achieved with an agent of interest may be "improved" relative to that obtained with a comparable reference agent or with no agent. Alternatively or additionally, in some embodiments, e.g., as set forth herein, an assessed value in a subject or system of interest may be "improved" relative to that obtained in the same subject or system under different conditions or at a different point in time (e.g., prior to or after an event such as administration of an agent of interest), or in a different, comparable subject (e.g., in a comparable subject or system that differs from the subject or system of interest in presence of one or more indicators of a particular disease, disorder or condition of interest, or in prior exposure to a condition or agent, etc.). In some embodiments, e.g., as set forth herein, comparative terms refer to statistically relevant differences (e.g., differences of a prevalence and/or magnitude sufficient to achieve statistical relevance). Those of skill in the art will be aware, or will readily be able to determine, in a given context, a degree and/or prevalence of difference that is required or sufficient to achieve such statistical significance.

Methylation: As used herein, the term "methylation" includes methylation at any of (i) C5 position of cytosine; (ii) N4 position of cytosine; and (iii) the N6 position of adenine. Methylation also includes (iv) other types of nucleotide methylation. A nucleotide that is methylated can be referred to as a "methylated nucleotide" or "methylated nucleotide base." In certain embodiments, e.g., as set forth herein, methylation specifically refers to methylation of cytosine residues. In some instances, methylation specifically refers to methylation of cytosine residues present in CpG sites.

Methylation assay: As used herein, the term "methylation assay" refers to any technique that can be used to determine the methylation status of a methylation locus.

Methylation biomarker: As used herein, the term "methylation biomarker" refers to a biomarker that is or includes at least one methylation locus and/or the methylation status of at least one methylation locus, e.g., a hypermethylated locus. In particular, a methylation biomarker is a biomarker characterized by a change between a first state and a second state (e.g., between a cancerous state and a non-cancerous state) in methylation status of one or more nucleic acid loci.

Methylation locus: As used herein, the term "methylation locus" refers to a DNA region that includes at least one differentially methylated region. A methylation locus that includes a greater number or frequency of methylated sites under a selected condition of interest, such as a cancerous state, can be referred to as a hypermethylated locus. A methylation locus that includes a smaller number or frequency of methylated sites under a selected condition of interest, such as a cancerous state, can be referred to as a hypomethylated locus. In some instances, e.g., as set forth herein, a methylation locus has a length of at least 10, at least 15, at least 20, at least 24, at least 50, or at least 75 base pairs. In some instances, e.g., as set forth herein, a methylation locus has a length of less than 1000, less than 750, less than 500, less than 350, less than 300, or less than 250 base pairs (e.g., where methylation status is determined using quantitative polymerase chain reaction (qPCR), e.g., methylation sensitive restriction enzyme quantitative polymerase chain reaction (MSRE-qPCR)).

Methylation site: As used herein, a methylation site refers to a nucleotide or nucleotide position that is methylated in at least one condition. In its methylated state, a methylation site can be referred to as a methylated site.

Methylation status: As used herein, "methylation status," "methylation state," or "methylation profile" refer to the number, frequency, or pattern of methylation at methylation sites within a methylation locus. Accordingly, a change in methylation status between a first state and a second state can be or include an increase in the number, frequency, or pattern of methylated sites, or can be or include a decrease in the number, frequency, or pattern of methylated sites. In various instances, a change in methylation status in a change in methylation value.

Methylation value: As used herein, the term "methylation value" refers to a numerical representation of a methylation status, e.g., in the form of number that represents the frequency or ratio of methylation of a methylation locus. In some instances, e.g., as set forth herein, a methylation value can be generated by a method that includes quantifying the amount of intact nucleic acid present in a sample following restriction digestion of the sample with a methylation dependent restriction enzyme. In some instances, e.g., as set forth herein, a methylation value can be generated by a method that includes comparing amplification profiles after bisulfite reaction of a sample. In some instances, e.g., as set forth herein, a methylation value can be generated by comparing sequences of bisulfite-treated and untreated nucleic acids. In some instances, e.g., as set forth herein, a methylation value is, includes, or is based on a quantitative PCR result.

Nucleic acid: As used herein, in its broadest sense, the term "nucleic acid" refers to any compound and/or substance that is or can be incorporated into an oligonucleotide chain. In some embodiments e.g., as set forth herein, a nucleic acid is a compound and/or substance that is or can be incorporated into an oligonucleotide chain via a phosphodiester linkage. As will be clear from context, in some embodiments e.g., as set forth herein, the term nucleic acid refers to an individual nucleic acid residue (e.g., a nucleotide and/or nucleoside), and in some embodiments e.g., as set forth herein refers to an polynucleotide chain comprising a plurality of individual nucleic acid residues. A nucleic acid can be or include DNA, RNA, or a combinations thereof. A nucleic acid can include natural nucleic acid residues, nucleic acid analogs, and/or synthetic residues. In some embodiments e.g., as set forth herein, a nucleic acid includes natural nucleotides (e.g., adenosine, thymidine, guanosine, cytidine, uridine, deoxyadenosine, deoxythymidine, deoxyguanosine, and deoxycytidine). In some embodiments e.g., as set forth herein, a nucleic acid is or includes of one or more nucleotide analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguano sine, 8-oxoadenosine, 8-oxoguanosine, 0(6)-methylguanine, 2-thiocytidine, methylated bases, intercalated bases, and combinations thereof).

In some embodiments e.g., as set forth herein, a nucleic acid has a nucleotide sequence that encodes a functional gene product such as an RNA or protein. In some embodiments e.g., as set forth herein, a nucleic acid includes one or more introns. In some embodiments e.g., as set forth herein, a nucleic acid includes one or more genes. In some embodiments e.g., as set forth herein, nucleic acids are prepared by one or more of isolation from a natural source, enzymatic synthesis by polymerization based on a complementary template (in vivo or in vitro), reproduction in a recombinant cell or system, and chemical synthesis.

In some embodiments e.g., as set forth herein, a nucleic acid analog differs from a nucleic acid in that it does not utilize a phosphodiester backbone. For example, in some embodiments e.g., as set forth herein, a nucleic acid can include one or more peptide nucleic acids, which are known in the art and have peptide bonds instead of phosphodiester bonds in the backbone. Alternatively or additionally, in some embodiments e.g., as set forth herein, a nucleic acid has one or more phosphorothioate and/or 5'-N-phosphoramidite linkages rather than phosphodiester bonds. In some embodiments e.g., as set forth herein, a nucleic acid comprises one or more modified sugars (e.g., 2'-fluororibose, ribose, 2'-deoxyribose, arabinose, and hexose) as compared with those in natural nucleic acids.

In some embodiments, e.g., as set forth herein, a nucleic acid is or includes at least 3, 4, 5, 6, 7, 8, 9, 10, 15, 20, 25, 30, 35, 40, 45, 50, 55, 60, 65, 70, 75, 80, 85, 90, 95, 100, 1 10, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues. In some embodiments, e.g., as set forth herein, a nucleic acid is partly or wholly single stranded, or partly or wholly double stranded.

Nucleic acid detection assay: As used herein, the term "nucleic acid detection assay" refers to any method of determining the nucleotide composition of a nucleic acid of interest. Nucleic acid detection assays include but are not limited to, DNA sequencing methods, polymerase chain reaction-based methods, probe hybridization methods, ligase chain reaction, etc.

Nucleotide: As used herein, the term "nucleotide" refers to a structural component, or building block, of polynucleotides, e.g., of DNA and/or RNA polymers. A nucleotide includes of a base (e.g., adenine, thymine, uracil, guanine, or cytosine) and a molecule of sugar and at least one phosphate group. As used herein, a nucleotide can be a methylated nucleotide or an un-methylated nucleotide. Those of skill in the art will appreciate that nucleic acid terminology, such as, as examples, "locus" or "nucleotide" can refer to both a locus or nucleotide of a single nucleic acid molecule and/or to the cumulative population of loci or nucleotides within a plurality of nucleic acids (e.g., a plurality of nucleic acids in a sample and/or representative of a subject) that are representative of the locus or nucleotide (e.g., having the same identical nucleic acid sequence and/or nucleic acid sequence context, or having a substantially identical nucleic acid sequence and/or nucleic acid context).

Oligonucleotide primer: As used herein, the term oligonucleotide primer, or primer, refers to a nucleic acid molecule used, capable of being used, or for use in, generating amplicons from a template nucleic acid molecule. Under transcription-permissive conditions (e.g., in the presence of nucleotides and a DNA polymerase, and at a suitable temperature and pH), an oligonucleotide primer can provide a point of initiation of transcription from a template to which the oligonucleotide primer hybridizes. Typically, an oligonucleotide primer is a single-stranded nucleic acid between 5 and 200 nucleotides in length. Those of skill in the art will appreciate that optimal primer length for generating amplicons from a template nucleic acid molecule can vary with conditions including temperature parameters, primer composition, and transcription or amplification method. A pair of oligonucleotide primers, as used herein, refers to a set of two oligonucleotide primers that are respectively complementary to a first strand and a second strand of a template double-stranded nucleic acid molecule. First and second members of a pair of oligonucleotide primers may be referred to as a "forward" oligonucleotide primer and a "reverse" oligonucleotide primer, respectively, with respect to a template nucleic acid strand, in that the forward oligonucleotide primer is capable of hybridizing with a nucleic acid strand complementary to the template nucleic acid strand, the reverse oligonucleotide primer is capable of hybridizing with the template nucleic acid strand, and the position of the forward oligonucleotide primer with respect to the template nucleic acid strand is 5' of the position of the reverse oligonucleotide primer sequence with respect to the template nucleic acid strand. It will be understood by those of skill in the art that the identification of a first and second oligonucleotide primer as forward and reverse oligonucleotide primers, respectively, is arbitrary inasmuch as these identifiers depend upon whether a given nucleic acid strand or its complement is utilized as a template nucleic acid molecule.

Overlapping: The term "overlapping" is used herein in reference to two regions of DNA, each of which contains a sub-sequence that is substantially identical to a sub-sequence of the same length in the other region (e.g., the two regions of DNA have a common sub-sequence). "Substantially identical" means that the two identically-long sub-sequences differ by fewer than a given number of base pairs. In certain instances, e.g., as set forth herein, each sub-sequence has a length of at least 20 base pairs that differ by fewer than 4, 3, 2, or 1 base pairs from each other (e.g., the two sub-sequences having at least 80%, at least 85%, at least 90%, at least 95% similarity, at least 97% similarity, at least 98% similarity, at least 99% similarity, or at least 99.5% similarity). In certain instances, e.g., as set forth herein, each sub-sequence has a length of at least 24 base pairs that differ by fewer than 5, 4, 3, 2, or 1 base pairs (e.g., the two sub-sequences having at least 80%, at least 85%, at least 90%, at least 95% similarity, at least 97% similarity, at least 98% similarity, at least 99% similarity, or at least 99.5% similarity). In certain instances, e.g., as set forth herein, each sub-sequence has a length of at least 50 base pairs that differ by fewer than 10, 9, 8, 7, 6, 5, 4, 3, 2, or 1 base pairs (e.g., the two sub-sequences having at least 80%, at least 85%, at least 90%, at least 95% similarity, at least 97% similarity, at least 98% similarity, at least 99% similarity, or at least 99.5% similarity). In certain instances, e.g., as set forth herein, each sub-sequence has a length of at least 100 base pairs that differ by fewer than 20, 15, 10, 9, 8, 7, 6, 5, 4, 3, 2, or 1 base pairs (e.g., the two sub-sequences having at least 80%, at least 85%, at least 90%, at least 95% similarity, at least 97% similarity, at least 98% similarity, at least 99% similarity, or at least 99.5% similarity). In certain instances, e.g., as set forth herein, each sub-sequence has a length of at least 200 base pairs that differ by fewer than 40, 30, 20, 15, 10, 9, 8, 7, 6, 5, 4, 3, 2, or 1 base pairs (e.g., the two sub-sequences having at least 80%, at least 85%, at least 90%, at least 95% similarity, at least 97% similarity, at least 98% similarity, at least 99% similarity, or at least 99.5% similarity). In certain instances, e.g., as set forth herein, each sub-sequence has a length of at least 250 base pairs that differ by fewer than 50, 40, 30, 20, 15, 10, 9, 8, 7, 6, 5, 4, 3, 2, or 1 base pairs (e.g., the two sub-sequences having at least 80%, at least 85%, at least 90%, at least 95% similarity, at least 97% similarity, at least 98% similarity, at least 99% similarity, or at least 99.5% similarity). In certain instances, e.g., as set forth herein, each sub-sequence has a length of at least 300 base pairs that differ by fewer than 60, 50, 40, 30, 20, 15, 10, 9, 8, 7, 6, 5, 4, 3, 2, or 1 base pairs (e.g., the two sub-sequences having at least 80%, at least 85%, at least 90%, at least 95% similarity, at least 97% similarity, at least 98% similarity, at least 99% similarity, or at least 99.5% similarity). In certain instances, e.g., as set forth herein, each sub-sequence has a length of at least 500 base pairs that differ by fewer than 100, 60, 50, 40, 30, 20, 15, 10, 9, 8, 7, 6, 5, 4, 3, 2, or 1 base pairs (e.g., the two sub-sequences having at least 80%, at least 85%, at least 90%, at least 95% similarity, at least 97% similarity, at least 98% similarity, at least 99% similarity, or at least 99.5% similarity). In certain instances, e.g., as set forth herein, each sub-sequence has a length of at least 1000 base pairs that differ by fewer than 200, 100, 60, 50, 40, 30, 20, 15, 10, 9, 8, 7, 6, 5, 4, 3, 2, or 1 base pairs (e.g., the two sub-sequences having at least 80%, at least 85%, at least 90%, at least 95% similarity, at least 97% similarity, at least 98% similarity, at least 99% similarity, or at least 99.5% similarity). In certain instances, e.g., as set forth herein, the subsequence of a first region of the two regions of DNA may comprise the entirety of the second region of the two regions of DNA (or vice versa) (e.g., the common sub-sequence may contain the whole of either or both regions).

Pharmaceutical composition: As used herein, the term "pharmaceutical composition" refers to a composition in which an active agent is formulated together with one or more pharmaceutically acceptable carriers. In some embodiments, e.g., as set forth herein, the active agent is present in a unit dose amount appropriate for administration to a subject, e.g., in a therapeutic regimen that shows a statistically significant probability of achieving a predetermined therapeutic effect when administered to a relevant population. In some embodiments, e.g., as set forth herein, a pharmaceutical composition can be formulated for administration in a particular form (e.g., in a solid form or a liquid form), and/or can be specifically adapted for, for example: oral administration (for example, as a drenche (aqueous or non-aqueous solutions or suspensions), tablet, capsule, bolus, powder, granule, paste, etc., which can be formulated specifically for example for buccal, sublingual, or systemic absorption); parenteral administration (for example, by subcutaneous, intramuscular, intravenous or epidural injection as, for example, a sterile solution or suspension, or sustained-release formulation, etc.); topical application (for example, as a cream, ointment, patch or spray applied for example to skin, lungs, or oral cavity); intravaginal or intrarectal administration (for example, as a pessary, suppository, cream, or foam); ocular administration; nasal or pulmonary administration, etc.

Pharmaceutically acceptable: As used herein, the term "pharmaceutically acceptable," as applied to one or more, or all, component(s) for formulation of a composition as disclosed herein, means that each component must be compatible with the other ingredients of the composition and not deleterious to the recipient thereof.

Pharmaceutically acceptable carrier: As used herein, the term "pharmaceutically acceptable carrier" refers to a pharmaceutically-acceptable material, composition, or vehicle, such as a liquid or solid filler, diluent, excipient, or solvent encapsulating material, that facilitates formulation and/or modifies bioavailability of an agent, e.g., a pharmaceutical agent. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Prevent or prevention: The terms "prevent" and "prevention," as used herein in connection with the occurrence of a disease, disorder, or condition, refers to reducing the risk of developing the disease, disorder, or condition; delaying onset of the disease, disorder, or condition; delaying onset of one or more characteristics or symptoms of the disease, disorder, or condition; and/or to reducing the frequency and/or severity of one or more characteristics or symptoms of the disease, disorder, or condition. Prevention can refer to prevention in a particular subject or to a statistical impact on a population of subjects. Prevention can be considered complete when onset of a disease, disorder, or condition has been delayed for a predefined period of time.

Probe: As used herein, the term "probe" refers to a single- or double-stranded nucleic acid molecule that is capable of hybridizing with a complementary target and includes a detectable moiety. In certain embodiments, e.g., as set forth herein, a probe is a restriction digest product or is a synthetically produced nucleic acid, e.g., a nucleic acid produced by recombination or amplification. In some instances, e.g., as set forth herein, a probe is a capture probe useful in detection, identification, and/or isolation of a target sequence, such as a gene sequence. In various instances, e.g., as set forth herein, a detectable moiety of probe can be, e.g., an enzyme (e.g., ELISA, as well as enzyme-based histochemical assays), fluorescent moiety, radioactive moiety, or moiety associated with a luminescence signal.

Prognosis: As used herein, the term "prognosis" refers to determining the qualitative of quantitative probability of at least one possible future outcome or event. As used herein, a prognosis can be a determination of the likely course of a disease, disorder, or condition such as cancer in a subject, a determination regarding the life expectancy of a subject, or a determination regarding response to therapy, e.g., to a particular therapy.

Prognostic information: As used herein, the term "prognostic information" refers to information useful in providing a prognosis. Prognostic information can include, without limitation, biomarker status information.

Promoter: As used herein, a "promoter" can refer to a DNA regulatory region that directly or indirectly (e.g., through promoter-bound proteins or substances) associates with an RNA polymerase and participates in initiation of transcription of a coding sequence.

Reference: As used herein describes a standard or control relative to which a comparison is performed. For example, in some embodiments, e.g., as set forth herein, an agent, subject, animal, individual, population, sample, sequence, or value of interest is compared with a reference or control agent, subject, animal, individual, population, sample, sequence, or value. In some embodiments, e.g., as set forth herein, a reference or characteristic thereof is tested and/or determined substantially simultaneously with the testing or determination of the characteristic in a sample of interest. In some embodiments, e.g., as set forth herein, a reference is a historical reference, optionally embodied in a tangible medium. Typically, as would be understood by those of skill in the art, a reference is determined or characterized under comparable conditions or circumstances to those under assessment, e.g., with regard to a sample. Those skilled in the art will appreciate when sufficient similarities are present to justify reliance on and/or comparison to a particular possible reference or control.

Risk: As used herein with respect to a disease, disorder, or condition, the term "risk" refers to the qualitative of quantitative probability (whether expressed as a percentage or otherwise) that a particular individual will develop the disease, disorder, or condition. In some embodiments, e.g., as set forth herein, risk is expressed as a percentage. In some embodiments, e.g., as set forth herein, a risk is a qualitative of quantitative probability that is equal to or greater than 0, 1, 2, 3, 4, 5, 6, 7, 8, 9, 10, 20, 30, 40, 50, 60, 70, 80, 90, or 100%. In some embodiments, e.g., as set forth herein, risk is expressed as a qualitative of quantitative level of risk relative to a reference risk or level or the risk of the same outcome attributed to a reference. In some embodiments, e.g., as set forth herein, relative risk is increased or decreased in comparison to the reference sample by a factor of 1.1, 1.2, 1.3, 1.4, 1.5, 1.6, 1.7, 1.8, 1.9, 2, 3, 4, 5, 6, 7, 8, 9, 10, or more.

Sample: As used herein, the term "sample" typically refers to an aliquot of material obtained or derived from a source of interest. In some embodiments, e.g., as set forth herein, a source of interest is a biological or environmental source. In some embodiments, e.g., as set forth herein, a sample is a "primary sample" obtained directly from a source of interest. In some embodiments, e.g., as set forth herein, as will be clear from context, the term "sample" refers to a preparation that is obtained by processing of a primary sample (e.g., by removing one or more components of and/or by adding one or more agents to a primary sample). Such a "processed sample" can include, for example cells, nucleic acids, or proteins extracted from a sample or obtained by subjecting a primary sample to techniques such as amplification or reverse transcription of nucleic acids, isolation and/or purification of certain components, etc.

In certain instances, e.g., as set forth herein, a processed sample can be a DNA sample that has been amplified (e.g., pre-amplified). Thus, in various instances, e.g., as set forth herein, an identified sample can refer to a primary form of the sample or to a processed form of the sample. In some instances, e.g., as set forth herein, a sample that is enzyme-digested DNA can refer to primary enzyme-digested DNA (the immediate product of enzyme digestion) or a further processed sample such as enzyme-digested DNA that has been subject to an amplification step (e.g., an intermediate amplification step, e.g., pre-amplification) and/or to a filtering step, purification step, or step that modifies the sample to facilitate a further step, e.g., in a process of determining methylation status (e.g., methylation status of a primary sample of DNA and/or of DNA as it existed in its original source context).

Screening: As used herein, the term "screening" refers to any method, technique, process, or undertaking intended to generate diagnostic information and/or prognostic information. Accordingly, those of skill in the art will appreciate that the term screening encompasses method, technique, process, or undertaking that determines whether an individual has, is likely to have or develop, or is at risk of having or developing a disease, disorder, or condition, e.g., colorectal cancer.

Specificity: As used herein, the "specificity" of a biomarker refers to the percentage of samples that are characterized by absence of the event or state of interest for which measurement of the biomarker accurately indicates absence of the event or state of interest (true negative rate). In various embodiments, e.g., as set forth herein, characterization of the negative samples is independent of the biomarker, and can be achieved by any relevant measure, e.g., any relevant measure known to those of skill in the art. Thus, specificity reflects the probability that the biomarker would detect the absence of the event or state of interest when measured in a sample not characterized that event or state of interest. In particular embodiments in which the event or state of interest is colorectal cancer, e.g., as set forth herein, specificity refers to the probability that a biomarker would detect the absence of colorectal cancer in a subject lacking colorectal cancer. Lack of colorectal cancer can be determined, e.g., by histology.

Sensitivity: As used herein, the "sensitivity" of a biomarker refers to the percentage of samples that are characterized by the presence of the event or state of interest for which measurement of the biomarker accurately indicates presence of the event or state of interest (true positive rate). In various embodiments, e.g., as set forth herein, characterization of the positive samples is independent of the biomarker, and can be achieved by any relevant measure, e.g., any relevant measure known to those of skill in the art. Thus, sensitivity reflects the probability that a biomarker would detect the presence of the event or state of interest when measured in a sample characterized by presence of that event or state of interest. In particular embodiments in which the event or state of interest is colorectal cancer, e.g., as set forth herein, sensitivity refers to the probability that a biomarker would detect the presence of colorectal cancer in a subject that has colorectal cancer. Presence of colorectal cancer can be determined, e.g., by histology.

Solid Tumor: As used herein, the term "solid tumor" refers to an abnormal mass of tissue including cancer cells. In various embodiments, e.g., as set forth herein, a solid tumor is or includes an abnormal mass of tissue that does not contain cysts or liquid areas. In some embodiments, e.g., as set forth herein, a solid tumor can be benign; in some embodiments, a solid tumor can be malignant. Examples of solid tumors include carcinomas, lymphomas, and sarcomas. In some embodiments, e.g., as set forth herein, solid tumors can be or include adrenal, bile duct, bladder, bone, brain, breast, cervix, colon, endometrium, esophagum, eye, gall bladder, gastrointestinal tract, kidney, larynx, liver, lung, nasal cavity, nasopharynx, oral cavity, ovary, penis, pituitary, prostate, retina, salivary gland, skin, small intestine, stomach, testis, thymus, thyroid, uterine, vaginal, and/or vulval tumors.

Stage of cancer: As used herein, the term "stage of cancer" refers to a qualitative or quantitative assessment of the level of advancement of a cancer. In some embodiments, e.g., as set forth herein, criteria used to determine the stage of a cancer can include, but are not limited to, one or more of where the cancer is located in a body, tumor size, whether the cancer has spread to lymph nodes, whether the cancer has spread to one or more different parts of the body, etc. In some embodiments, e.g., as set forth herein, cancer can be staged using the so-called TNM System, according to which T refers to the size and extent of the main tumor, usually called the primary tumor; N refers to the number of nearby lymph nodes that have cancer; and M refers to whether the cancer has metastasized. In some embodiments, e.g., as set forth herein, a cancer can be referred to as Stage 0 (abnormal cells are present but have not spread to nearby tissue, also called carcinoma in situ, or CIS; CIS is not cancer, but it can become cancer), Stage I-III (cancer is present; the higher the number, the larger the tumor and the more it has spread into nearby tissues), or Stage IV (the cancer has spread to distant parts of the body). In some embodiments, e.g., as set forth herein, a cancer can be assigned to a stage selected from the group consisting of: in situ (abnormal cells are present but have not spread to nearby tissue); localized (cancer is limited to the place where it started, with no sign that it has spread); regional (cancer has spread to nearby lymph nodes, tissues, or organs): distant (cancer has spread to distant parts of the body); and unknown (there is not enough information to identify cancer stage).

Susceptible to: An individual who is "susceptible to" a disease, disorder, or condition is at risk for developing the disease, disorder, or condition. In some embodiments, e.g., as set forth herein, an individual who is susceptible to a disease, disorder, or condition does not display any symptoms of the disease, disorder, or condition. In some embodiments, e.g., as set forth herein, an individual who is susceptible to a disease, disorder, or condition has not been diagnosed with the disease, disorder, and/or condition. In some embodiments, e.g., as set forth herein, an individual who is susceptible to a disease, disorder, or condition is an individual who has been exposed to conditions associated with, or presents a biomarker status (e.g., a methylation status) associated with, development of the disease, disorder, or condition. In some embodiments, e.g., as set forth herein, a risk of developing a disease, disorder, and/or condition is a population-based risk (e.g., family members of individuals suffering from the disease, disorder, or condition).

Subject: As used herein, the term "subject" refers to an organism, typically a mammal (e.g., a human). In some embodiments, e.g., as set forth herein, a subject is suffering from a disease, disorder or condition. In some embodiments, e.g., as set forth herein, a subject is susceptible to a disease, disorder, or condition. In some embodiments, e.g., as set forth herein, a subject displays one or more symptoms or characteristics of a disease, disorder or condition. In some embodiments, e.g., as set forth herein, a subject is not suffering from a disease, disorder or condition. In some embodiments, e.g., as set forth herein, a subject does not display any symptom or characteristic of a disease, disorder, or condition. In some embodiments, e.g., as set forth herein, a subject is someone with one or more features characteristic of susceptibility to or risk of a disease, disorder, or condition. In some embodiments, e.g., as set forth herein, a subject is a patient. In some embodiments, e.g., as set forth herein, a subject is an individual to whom diagnosis has been performed and/or to whom therapy has been administered. In some instances, e.g., as set forth herein, a human subject can be interchangeably referred to as an "individual."

Therapeutic agent: As used herein, the term "therapeutic agent" refers to any agent that elicits a desired pharmacological effect when administered to a subject. In some embodiments, e.g., as set forth herein, an agent is considered to be a therapeutic agent if it demonstrates a statistically significant effect across an appropriate population. In some embodiments, e.g., as set forth herein, the appropriate population can be a population of model organisms or a human population. In some embodiments, e.g., as set forth herein, an appropriate population can be defined by various criteria, such as a certain age group, gender, genetic background, preexisting clinical conditions, etc. In some embodiments, e.g., as set forth herein, a therapeutic agent is a substance that can be used for treatment of a disease, disorder, or condition. In some embodiments, e.g., as set forth herein, a therapeutic agent is an agent that has been or is required to be approved by a government agency before it can be marketed for administration to humans. In some embodiments, e.g., as set forth herein, a therapeutic agent is an agent for which a medical prescription is required for administration to humans.

Therapeutically effective amount: As used herein, the term "therapeutically effective amount" refers to an amount that produces a desired effect for which it is administered. In some embodiments, e.g., as set forth herein, the term refers to an amount that is sufficient, when administered to a population suffering from or susceptible to a disease, disorder, or condition, in accordance with a therapeutic dosing regimen, to treat the disease, disorder, or condition. Those of ordinary skill in the art will appreciate that the term therapeutically effective amount does not in fact require successful treatment be achieved in a particular individual. Rather, a therapeutically effective amount can be an amount that provides a particular desired pharmacological response in a significant number of subjects when administered to individuals in need of such treatment. In some embodiments, e.g., as set forth herein, reference to a therapeutically effective amount can be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular agent can be formulated and/or administered in a single dose. In some embodiments, e.g., as set forth herein, a therapeutically effective agent can be formulated and/or administered in a plurality of doses, for example, as part of a multi-dose dosing regimen.

Treatment: As used herein, the term "treatment" (also "treat" or "treating") refers to administration of a therapy that partially or completely alleviates, ameliorates, relieves, inhibits, delays onset of, reduces severity of, and/or reduces incidence of one or more symptoms, features, and/or causes of a particular disease, disorder, or condition, or is administered for the purpose of achieving any such result. In some embodiments, e.g., as set forth herein, such treatment can be of a subject who does not exhibit signs of the relevant disease, disorder, or condition and/or of a subject who exhibits only early signs of the disease, disorder, or condition. Alternatively or additionally, such treatment can be of a subject who exhibits one or more established signs of the relevant disease, disorder and/or condition. In some embodiments, e.g., as set forth herein, treatment can be of a subject who has been diagnosed as suffering from the relevant disease, disorder, and/or condition. In some embodiments, e.g., as set forth herein, treatment can be of a subject known to have one or more susceptibility factors that are statistically correlated with increased risk of development of the relevant disease, disorder, or condition. In various examples, treatment is of a cancer.

Upstream: As used herein, the term "upstream" means a first DNA region is closer, relative to a second DNA region, to the N-terminus of a nucleic acid that includes the first DNA region and the second DNA region.

Unit dose: As used herein, the term "unit dose" refers to an amount administered as a single dose and/or in a physically discrete unit of a pharmaceutical composition. In many embodiments, e.g., as set forth herein, a unit dose contains a predetermined quantity of an active agent. In some embodiments, e.g., as set forth herein, a unit dose contains an entire single dose of the agent. In some embodiments, e.g., as set forth herein, more than one unit dose is administered to achieve a total single dose. In some embodiments, e.g., as set forth herein, administration of multiple unit doses is required, or expected to be required, in order to achieve an intended effect. A unit dose can be, for example, a volume of liquid (e.g., an acceptable carrier) containing a predetermined quantity of one or more therapeutic moieties, a predetermined amount of one or more therapeutic moieties in solid form, a sustained release formulation or drug delivery device containing a predetermined amount of one or more therapeutic moieties, etc. It will be appreciated that a unit dose can be present in a formulation that includes any of a variety of components in addition to the therapeutic agent(s). For example, acceptable carriers (e.g., pharmaceutically acceptable carriers), diluents, stabilizers, buffers, preservatives, etc., can be included. It will be appreciated by those skilled in the art, in many embodiments, e.g., as set forth herein, a total appropriate daily dosage of a particular therapeutic agent can comprise a portion, or a plurality, of unit doses, and can be decided, for example, by a medical practitioner within the scope of sound medical judgment. In some embodiments, e.g., as set forth herein, the specific effective dose level for any particular subject or organism can depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts Unmethylated: As used herein, the terms "unmethylated" and "non-methylated" are used interchangeable and mean that an identified DNA region includes no methylated nucleotides.

Variant: As used herein, the term "variant" refers to an entity that shows significant structural identity with a reference entity but differs structurally from the reference entity in the presence, absence, or level of one or more chemical moieties as compared with the reference entity. In some embodiments, e.g., as set forth herein, a variant also differs functionally from its reference entity. In general, whether a particular entity is properly considered to be a "variant" of a reference entity is based on its degree of structural identity with the reference entity. A variant can be a molecule comparable, but not identical to, a reference. For example, a variant nucleic acid can differ from a reference nucleic acid at one or more differences in nucleotide sequence. In some embodiments, e.g., as set forth herein, a variant nucleic acid shows an overall sequence identity with a reference nucleic acid that is at least 85%, 86%, 87%, 88%, 89%, 90%, 91%, 92%, 93%, 94%, 95%, 96%, 97%, or 99%. In many embodiments, e.g., as set forth herein, a nucleic acid of interest is considered to be a "variant" of a reference nucleic acid if the nucleic acid of interest has a sequence that is identical to that of the reference but for a small number of sequence alterations at particular positions. In some embodiments, e.g., as set forth herein, a variant has 10, 9, 8, 7, 6, 5, 4, 3, 2, or 1 substituted residues as compared with a reference. In some embodiments, e.g., as set forth herein, a variant has not more than 5, 4, 3, 2, or 1 residue additions, substitutions, or deletions as compared with the reference. In various embodiments, e.g., as set forth herein, the number of additions, substitutions, or deletions is fewer than about 25, about 20, about 19, about 18, about 17, about 16, about 15, about 14, about 13, about 10, about 9, about 8, about 7, about 6, and commonly are fewer than about 5, about 4, about 3, or about 2 residues.

BRIEF DESCRIPTION OF THE DRAWINGS

The foregoing and other objects, aspects, features, and advantages of the present disclosure will become more apparent and better understood by referring to the following description taken in conjunction with the accompanying drawings, in which:

FIG. 2 is a table showing characteristics of a first subject group of 70 human subjects. FIG. 2 provides the percent female, percent male, age range, and BMI of subjects. FIG. 2 further distinguishes the types of colorectal cancer identified in the first subject group as localized or advanced based on histological evaluation, and as a proximal or distal based on colonoscopy evaluation of colon.

FIG. 3 is a table showing characteristics of a second subject group of 63 human subjects. FIG. 3 provides the percent female, percent male, age range, and BMI of subjects. FIG. 3 further distinguishes the types of colorectal cancer identified in the second subject group as localized or advanced based on histological evaluation, and as a proximal or distal based on colonoscopy evaluation of colon.

FIG. 10 is a table showing characteristics of a third subject group of 82 human subjects. FIG. 10 provides the percent female, percent male, age range, and BMI of subjects diagnosed by screening using 28 colorectal cancer DMRs of the present disclosure. FIG. 10 further distinguishes the types of colorectal cancer identified in the third subject group as localized or advanced based on histological evaluation, and as a proximal or distal based on colonoscopy evaluation of colon.

FIG. 21 is a table showing the characteristics of a subject group of 215 subjects used as a training set. FIG. 21 provides the number of females, number of males, age range, and colorectal cancer status of subjects. FIG. 21 further distinguishes the types of colorectal cancer identified in those having colorectal cancer in the subject group as localized or advanced based on histological evaluation, and as a proximal or distal based on colonoscopy evaluation of colon.

FIG. 22 is a table showing the characteristics of a fourth subject group of 774 subjects used as a validation set. FIG. 22 provides the number of females, number of males, age range, and cancer status of subjects. FIG. 22 further distinguishes the types of cancer identified in those having cancer in the subject group as localized or advanced based on histological evaluation.

DETAILED DESCRIPTION

Screening for Colorectal Cancer

There is a need for improved methods of detecting (e.g., screening for) colorectal cancer, including screening for diagnosis of early-stage colorectal cancer. Despite recommendations for screening of individuals, e.g., over age 50, colorectal cancer screening programs are often ineffective or unsatisfactory. Improved colorectal cancer screening improves diagnosis and reduces colorectal cancer mortality.

Figure 20:
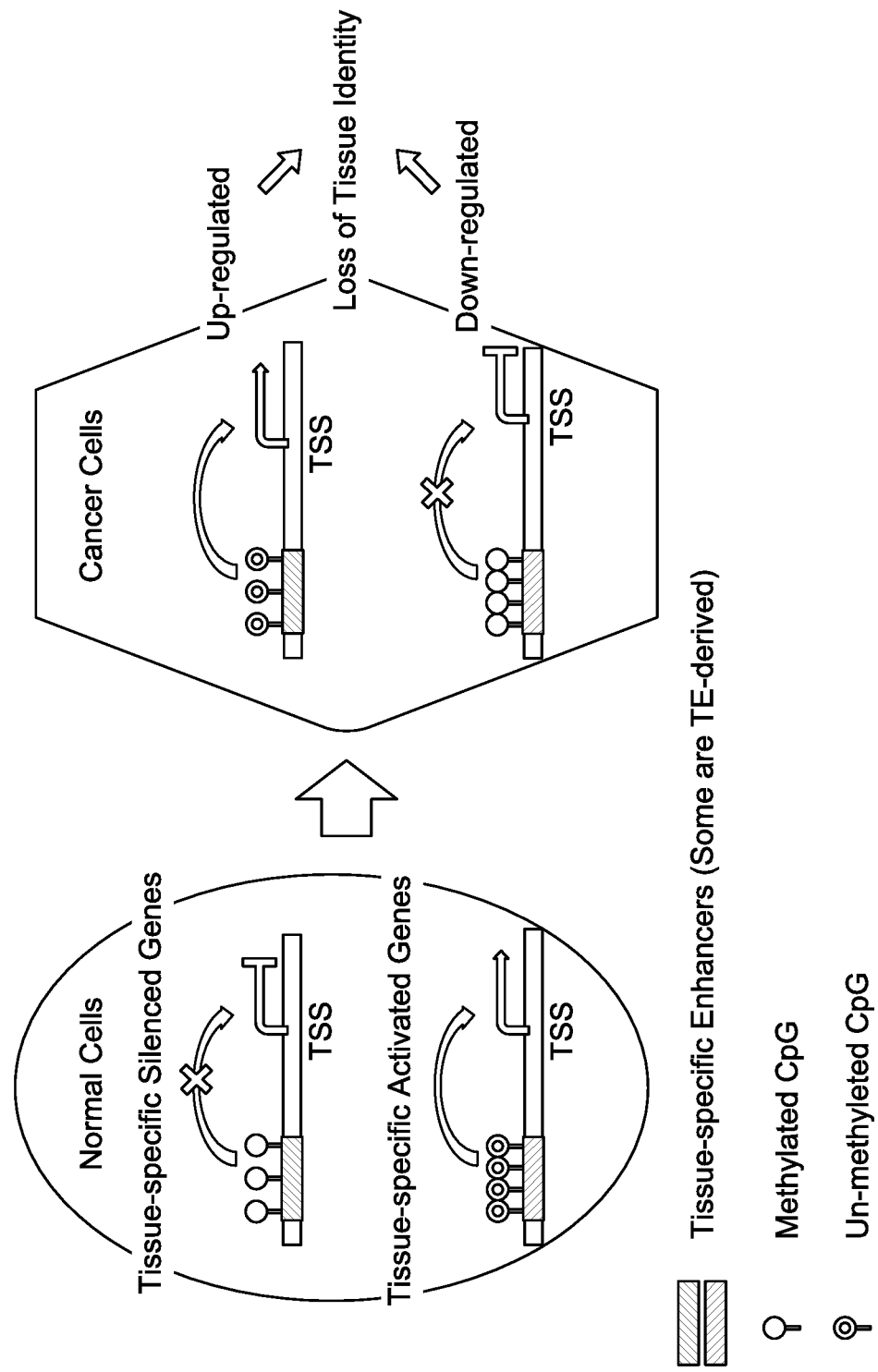
FIG. 20 is a schematic showing example methylation changes in methylation status between normal and cancer cells, and further indicates how changes in methylation status can impact gene expression differences between normal and cancer cells.

DNA methylation (e.g., hypermethylation or hypomethylation) can activate or inactivate genes, including genes that impact cancer development (see, e.g., FIG. 20). Thus, for example, hypermethylation can inactivate one or more genes that typically act to suppress cancer, causing or contributing to development of cancer in a sample or subject.

The present disclosure includes the discovery that determination of the methylation status of one or more methylation loci provided herein, and/or the methylation status of one or more DMRs provided herein, and/or the methylation status of one or more methylation sites provided herein, provides screening for colorectal cancer, e.g., with a high degree of sensitivity and/or specificity. The present disclosure provides compositions and methods including or relating to colorectal cancer methylation biomarkers that, individually or in various panels comprising two or more colorectal cancer methylation biomarkers, provide for screening of colorectal cancer, e.g., with a high degree of specificity and/or sensitivity.

In various embodiments, a colorectal cancer methylation biomarker of the present disclosure is selected from a methylation locus that is or includes ALK, LONRF2, ADAMTS2, FGF14, DMRT1, ST6GALNAC5, MCIDAS, PDGFD, GSG1L, ZNF492, ZNF568, ZNF542, ZNF471, ZNF132, JAM2, and CNRIP1 (see, e.g., Table 1). In various embodiments, a colorectal cancer DMR is selected from ALK '434, CNRIP1 '232, CNRIP1 '272, LONRF2 '281, LONRF2 '387, ADAMTS2 '254, ADAMTS2 '284, ADAMTS2 '328, FGF14 '577, DMRT1 '934, ST6GALNAC5 '456, MCIDAS '855, MCIDAS '003, PDGFD '388, PDGFD '921, GSG1L '861, ZNF492 '499, ZNF492 '069, ZNF568 '252, ZNF568 '405, ZNF542 '525, ZNF542 '502, ZNF471 '527, ZNF471 '558, ZNF471 '662, ZNF132 '268, ZNF132 '415, and JAM2 '320 (see, e.g., Table 7)

For the avoidance of any doubt, any methylation biomarker provided herein can be, or be included in, among other things, a colorectal cancer methylation biomarker.

In some embodiments, a colorectal cancer methylation biomarker can be or include a single methylation locus. In some embodiments, a colorectal cancer methylation biomarker can be or include two or more methylation loci. In some embodiments, a colorectal cancer methylation biomarker can be or include a single differentially methylated region (DMR). In some embodiments, a methylation locus can be or include two or more DMRs. In some embodiments, a methylation biomarker can be or include a single methylation site. In other embodiments, a methylation biomarker can be or include two or more methylation sites. In some embodiments, a methylation locus can include two or more DMRs and further include DNA regions adjacent to one or more of the included DMRs.

In some instances, a methylation locus is or includes a gene, such as a gene provided in Table 1. In some instances a methylation locus is or includes a portion of a gene, e.g., a portion of a gene provided in Table 1. In some instances, a methylation locus includes but is not limited to identified nucleic acid boundaries of a gene.

In some instances, a methylation locus is or includes a coding region of a gene, such as a coding region of a gene provided in Table 1. In some instances a methylation locus is or includes a portion of the coding region of gene, e.g., a portion of the coding region a gene provided in Table 1. In some instances, a methylation locus includes but is not limited to identified nucleic acid boundaries of a coding region of gene.

In some instances, a methylation locus is or includes a promoter and/or other regulatory region of a gene, such as a promoter and/or other regulatory region of a gene provided in Table 1. In some instances a methylation locus is or includes a portion of the promoter and/or regulatory region of gene, e.g., a portion of promoter and/or regulatory region a gene provided in Table 1. In some instances, a methylation locus includes but is not limited to identified nucleic acid boundaries of a promoter and/or other regulatory region of gene. In some embodiments a methylation locus is or includes a high CpG density promoter, or a portion thereof.

In some embodiments, a methylation locus is or includes non-coding sequence. In some embodiments, a methylation locus is or includes one or more exons, and/or one or more introns.

In some embodiments, a methylation locus includes a DNA region extending a predetermined number of nucleotides upstream of a coding sequence, and/or a DNA region extending a predetermined number of nucleotides downstream of a coding sequence. In various instances, a predetermined number of nucleotides upstream and/or downstream and be or include, e.g., 500 bp, 1 kb, 2 kb, 3 kb, 4 kb, 5 kb, 10 kb, 20 kb, 30 kb, 40 kb, 50 kb, 75 kb, or 100 kb. Those of skill in the art will appreciate that methylation biomarkers capable of impacting expression of a coding sequence may typically be within any of these distances of the coding sequence, upstream and/or downstream.

Those of skill in the art will appreciate that a methylation locus identified as a methylation biomarker need not necessarily be assayed in a single experiment, reaction, or amplicon. A single methylation locus identified as a colorectal cancer methylation biomarker can be assayed, e.g., in a method including separate amplification (or providing oligonucleotide primers and conditions sufficient for amplification of) of one or more distinct or overlapping DNA regions within a methylation locus, e.g., one or more distinct or overlapping DMRs. Those of skill in the art will further appreciate that a methylation locus identified as a methylation biomarker need not be analyzed for methylation status of each nucleotide, nor each CpG, present within the methylation locus. Rather, a methylation locus that is a methylation biomarker may be analyzed, e.g., by analysis of a single DNA region within the methylation locus, e.g., by analysis of a single DMR within the methylation locus.

DMRs of the present disclosure can be a methylation locus or include a portion of a methylation locus. In some instances, a DMR is a DNA region with a methylation locus that is, e.g., 1 to 5,000 bp in length. In various embodiments, a DMR is a DNA region with a methylation locus that is equal to or less than 5000 bp, 4,000 bp, 3,000 bp, 2,000 bp, 1,000 bp, 950 bp, 900 bp, 850 bp, 800 bp, 750 bp, 700 bp, 650 bp, 600 bp, 550 bp, 500 bp, 450 bp, 400 bp, 350 bp, 300 bp, 250 bp, 200 bp, 150 bp, 100 bp, 50 bp, 40 bp, 30 bp, 20 bp, or 10 bp in length. In some embodiments, a DMR is 1, 2, 3, 4, 5, 6, 7, 8 or 9 bp in length.

Methylation biomarkers, including without limitation methylation loci and DMRs provided herein, can include at least one methylation site that is a colorectal cancer methylation biomarker.

For clarity, those of skill in the art will appreciate that term methylation biomarker is used broadly, such that a methylation locus can be a methylation biomarker that includes one or more DMRs, each of which DRMs is also itself a methylation biomarker, and each of which DMRs can include one or more methylation sites, each of which methylation sites is also itself a methylation biomarker. Moreover, a methylation biomarker can include two or more methylation loci. Accordingly, status as a methylation biomarker does not turn on the contiguousness of nucleic acids included in a biomarker, but rather on the existence of a change in methylation status for included DNA region(s) between a first state and a second state, such as between colorectal cancer and controls.

As provided herein, a methylation locus can be any of one or more methylation loci each of which methylation loci is, includes, or is a portion of a gene identified in Table 1. In some particular embodiments, a colorectal cancer methylation biomarker includes a single methylation locus that is, includes, or is a portion of a gene identified in Table 1. For example, in various embodiments, e.g., as described herein, a colorectal cancer methylation biomarker can include a methylation locus that is, includes, or is a portion of a gene selected from ZNF132, ADAMTS2, ZNF542, LONRF2, ZNF492, FGF14, ST6GALNAC5, PDGFD, ZNF471, JAM2, GSG1L, DMRT1, and MCIDAS.

In some particular embodiments, a colorectal cancer methylation biomarker includes two or more methylation loci, each of which is, includes, or is a portion of a gene identified in Table 1. In some embodiments, a colorectal cancer methylation biomarker includes 2, 3, 4, 5, 6, 7, 8, 9, 10, 11, 12, 13, 14, 15, or 16, methylation loci, each of which is, includes, or is a portion of a gene identified in Table 1.

In some particular embodiments, a colorectal cancer methylation biomarker includes two or more methylation loci, each of which two or more methylation loci is, includes, or is a portion of a gene identified in any one of Tables 1 to 6. In some particular embodiments, a colorectal cancer methylation biomarker includes two or more methylation loci, each of which two or more methylation loci is, includes, or is a portion of a gene identified in any one of Tables 2 to 6. In some particular embodiments, a colorectal cancer methylation biomarker includes two or more methylation loci, each of which two or more methylation loci is, includes, or is a portion of a gene identified in Table 1. In some particular embodiments, a colorectal cancer methylation biomarker includes two methylation loci, each of which two or more methylation loci is, includes, or is a portion of a gene identified in Table 2. In some particular embodiments, a colorectal cancer methylation biomarker includes three methylation loci, each of which three methylation loci is, includes, or is a portion of a gene identified in Table 3. In some particular embodiments, a colorectal cancer methylation biomarker includes four methylation loci, each of which four methylation loci is, includes, or is a portion of a gene identified in Table 4. In some particular embodiments, a colorectal cancer methylation biomarker includes six methylation loci, each of which six methylation loci is, includes, or is a portion of a gene identified in Table 5. In some particular embodiments, a colorectal cancer methylation biomarker includes eleven methylation loci, each of which eleven methylation loci is, includes, or is a portion of a gene identified in Table 6. In various particular embodiments, a colorectal cancer methylation biomarker or colorectal cancer methylation biomarker panel includes one or more methylation loci of the present disclosure, but does not include a methylation locus that is, includes, or is a portion of one or more of FGF14, ZNF471, PDGFD, and ALK.

TABLE 1

Methylation loci identified by gene name

| Gene | Example DNA Region of *Homo sapiens* (human) genome assembly GRCh38 (hg38) | SEQ ID NO |
|---|---|---|
| ZNF132 | ZNF132 chr19, bp 58439728 to 58440994 | SEQ ID NO: 1 |
| DMRT1 | DMRT1 chr9, bp 841340 to 968090 | SEQ ID NO: 2 |
| ALK | ALK chr2, bp 29193215 to 29922286 | SEQ ID NO: 3 |
| JAM2 | JAM2 chr21, bp 25637848 to 25714704 | SEQ ID NO: 4 |
| FGF14 | FGF14 chr13, bp 101919879 to 102403137 | SEQ ID NO: 5 |
| MCIDAS | MCIDAS chr5, bp 55220951 to 55221051 | SEQ ID NO: 6 |
| ST6GALNAC5 | ST6GALNAC5 chr1, bp 76866255 to 77063388 | SEQ ID NO: 7 |

TABLE 1-continued

Methylation loci identified by gene name

| Gene | Example DNA Region of Homo sapiens (human) genome assembly GRCh38 (hg38) | SEQ ID NO |
|---|---|---|
| LONRF2 | LONRF2 chr2, bp 100285667 to 100323015 | SEQ ID NO: 8 |
| PDGFD | PDGFD chr11, bp 104163499 to 104164026 | SEQ ID NO: 9 |
| GSG1L | GSG1L chr16, bp 27920615 to 28064275 | SEQ ID NO: 10 |
| ZNF492 | ZNF492 chr19, bp 22633051 to 22666433 | SEQ ID NO: 11 |
| ZNF568 | ZNF568 chr19, bp 36916312 to 36943940 | SEQ ID NO: 12 |
| ADAMTS2 | ADAMTS2 chr5, bp 179118114 to 179344392 | SEQ ID NO: 13 |
| ZNF542 | ZNF542 chr19, bp 56367838 to 56370986 | SEQ ID NO: 14 |
| ZNF471 | ZNF471 chr19, bp 56507245 to 56508589 | SEQ ID NO: 15 |
| CNRIP1 | CNRIP1 chr2, bp 68293114 to 68320928 | SEQ ID NO: 16 |

TABLE 2

Combination of 2 methylation loci

ZNF471
FGF14

TABLE 3

Combination of 3 methylation loci

ZNF471
FGF14
PDGFD

TABLE 4

Combination of 4 methylation loci

ZNF471
FGF14
PDGFD
ADAMTS2

TABLE 5

Combination of 6 methylation loci

ZNF471
FGF14
PDGFD
ADAMTS2
ZNF492
ST6GALNAC5

TABLE 6

Combination of 11 methylation loci

ZNF471
FGF14
PDGFD
ADAMTS2

TABLE 6-continued

Combination of 11 methylation loci

ZNF492
ST6GALNAC5
ZNF542
LONRF2
ZNF132
CNRIP1
ALK

As provided herein, a colorectal cancer methylation biomarker can be any of one or more DMRs each of which DMRs is present in a methylation locus that is, includes, or is a portion of a gene identified in Table 1. In some particular embodiments, a colorectal cancer methylation biomarker is or includes a single DMR that is, includes all or a portion of, or is present in a gene identified in Table 1. For example, in various embodiments, a colorectal cancer methylation biomarker can include a single DMR that is, includes all or a portion of, or is present in a gene selected from ALK, CNRIP1, LONRF2, ADAMTS2, FGF14, DMRT1, ST6GALNAC5, MCIDAS, PDGFD, GSG1L, ZNF492, ZNF568, ZNF542, ZNF471, ZNF132, and JAM2.

In some particular embodiments, a colorectal cancer methylation biomarker includes two or more DMRs, each of which is, includes all or a portion of, or is present in a gene identified in Table 1. In some embodiments, a colorectal cancer methylation biomarker includes 2, 3, 4, 5, 6, 7, 8, 9, 10, 11, 12, 13, 14, 15, or 16, DMRs, each of which is, includes all or a portion of, or is present in a gene identified in Table 1.

In some particular embodiments, a colorectal cancer methylation biomarker includes two or more DMRs, each of which two or more DMRs is, includes all or a portion of, or is present in a gene identified in any one of Tables 1-6. In some particular embodiments, a colorectal cancer methylation biomarker includes two DMRs, which two DMRs include DMRs that are, include all or a portion of, or are present in the genes identified in Table 2. In some particular embodiments, a colorectal cancer methylation biomarker includes three DMRs, which three DMRs include DMRs that are, include all or a portion of, or are present in the genes identified in Table 3. In some particular embodiments, a colorectal cancer methylation biomarker includes four DMRs, which four DMRs include DMRs that are, include all or a portion of, or are present in the genes identified in Table 4. In some particular embodiments, a colorectal cancer methylation biomarker includes six DMRs, which six DMRs include DMRs that are, include all or a portion of, or are present in the genes identified in Table 5. In some particular embodiments, a colorectal cancer methylation biomarker includes eleven DMRs, which eleven DMRs include DMRs that are, include all or a portion of, or are present in the genes identified in Table 6. In various particular embodiments, a colorectal cancer methylation biomarker or colorectal cancer methylation biomarker panel includes one or more DMRs, but the one or more DMRs do not include a DMR that is, includes all or a portion of, or is present in one or more of FGF14, ZNF471, PDGFD, and ALK.

As provided herein, a colorectal cancer methylation biomarker can include any of one or more DMRs, each of which DMRs is, includes all of, or includes a portion of a DMR identified in Table 7, including without limitation DMRs specifically as identified in Table 7. In some particular embodiments, a colorectal cancer methylation biomarker is or includes a single DMR that is, includes all of, or includes a portion of a DMR identified in Table 7, including without limitation a DMR specifically as identified in Table 7, e.g., a DMR of Table 7 selected from the group of DMRs including, without limitation, ALK '434, CNRIP1 '232, CNRIP1 '272, LONRF2 '281, LONRF2 '387, ADAMTS2 '254, ADAMTS2 '284, ADAMTS2 '328, FGF14 '577, DMRT1 '934, ST6GALNAC5 '456, MCIDAS '855, MCIDAS '003, PDGFD '388, PDGFD '921, GSG1L '861, ZNF492 '499, ZNF492 '069, ZNF568 '252, ZNF568 '405, ZNF542 '525, ZNF542 '502, ZNF471 '527, ZNF471 '558, ZNF471 '662, ZNF132 '268, ZNF132 '415, and JAM2 '320. For example, in various embodiments, a colorectal cancer methylation biomarker can include a single DMR that is, includes all of, or includes a portion of a DMR selected from LONRF2 '281, LONRF2 '387, ADAMTS2 '254, ADAMTS2 '284, ADAMTS2 '328, FGF14 '577, ST6GALNAC5 '456, PDGFD '388, PDGFD '921, ZNF492 '499, ZNF492 '069, ZNF542 '525, ZNF542 '502, ZNF471 '527, ZNF471 '558, and ZNF471 '662.

In some particular embodiments, a colorectal cancer methylation biomarker includes two or more DMRs, each of which DMRs is, includes all of, or includes a portion of a DMR identified in Table 7, including without limitation DMRs specifically as identified in Table 7. In some embodiments, a colorectal cancer methylation biomarker includes 2, 3, 4, 5, 6, 7, 8, 9, 10, 11, 12, 13, 14, 15, 16, 17, 18, 19, 20, 21, 22, 23, 24, 25, 26, 27, or 28 DMRs, each of which DMRs is, includes all of, or includes a portion of a DMR identified in Table 7, including without limitation DMRs specifically as identified in Table 7.

In some particular embodiments, a colorectal cancer methylation biomarker includes two or more DMRs, each of which two or more DMRs is, includes all of, or includes a portion of a DMR identified in any one of Tables 7 to 12, including without limitation DMRs and combinations thereof specifically as identified in Tables 8 to 12. In some particular embodiments, a colorectal cancer methylation biomarker includes two DMRs, which two DMRs are the DMRs identified in Table 8. In some particular embodiments, a colorectal cancer methylation biomarker includes three DMRs, which three DMRs are the DMRs identified in Table 9. In some particular embodiments, a colorectal cancer methylation biomarker includes five DMRs, which five DMRs are the DMRs identified in Table 10. In some particular embodiments, a colorectal cancer methylation biomarker includes eight DMRs, which eight DMRs are the DMRs identified in Table 11. In some particular embodiments, a colorectal cancer methylation biomarker includes fifteen DMRs, which fifteen DMRs are the DMRs identified in Table 12. In various particular embodiments, a colorectal cancer methylation biomarker or colorectal cancer methylation biomarker panel includes one or more DMRs of Table 7, but the one or more DMRs do not include one or more, or all, DMRs of FGF14, ZNF471, PDGFD, and ALK, e.g., do not include one or more, or all, DMRs of FGF14, ZNF471, PDGFD, and ALK as provided in Table 7.

TABLE 7

Colorectal cancer DMRs

| gene name | chr | start site | end site | width | SEQ ID NO | Loci Reference Name |
| --- | --- | --- | --- | --- | --- | --- |
| ALK | 2 | 29921434 | 29921541 | 108 | SEQ ID NO: 17 | ALK '434 |
| CNRIP1 | 2 | 68319232 | 68319342 | 111 | SEQ ID NO: 18 | CNRIP1 '232 |
| LONRF2 | 2 | 100321281 | 100321395 | 115 | SEQ ID NO: 19 | LONRF2 '281 |
| LONRF2 | 2 | 100322387 | 100322463 | 77 | SEQ ID NO: 20 | LONRF2 '387 |
| ADAMTS2 | 5 | 179344254 | 179344348 | 95 | SEQ ID NO: 21 | ADAMTS2 '254 |
| ADAMTS2 | 5 | 179344284 | 179344383 | 100 | SEQ ID NO: 22 | ADAMTS2 '284 |
| FGF14 | 13 | 102394577 | 102394651 | 75 | SEQ ID NO: 23 | FGF14 '577 |
| DMRT1 | 9 | 841934 | 842046 | 113 | SEQ ID NO: 24 | DMRT1 '934 |
| ST6GALNAC5 | 1 | 76868456 | 76868525 | 70 | SEQ ID NO: 25 | ST6GALNAC5 '456 |
| MCIDAS | 5 | 55220855 | 55220971 | 117 | SEQ ID NO: 26 | MCIDAS '855 |
| MCIDAS | 5 | 55221003 | 55221122 | 120 | SEQ ID NO: 27 | MCIDAS '003 |
| PDGFD | 11 | 104163388 | 104163503 | 116 | SEQ ID NO: 28 | PDGFD '388 |
| PDGFD | 11 | 104163921 | 104164058 | 138 | SEQ ID NO: 29 | PDGFD '921 |
| GSG1L | 16 | 28063861 | 28063964 | 104 | SEQ ID NO: 30 | GSG1L '861 |
| ZNF492 | 19 | 22634499 | 22634596 | 98 | SEQ ID NO: 31 | ZNF492 '499 |
| ZNF568 | 19 | 36916252 | 36916371 | 120 | SEQ ID NO: 32 | ZNF568 '252 |
| ZNF568 | 19 | 36916405 | 36916476 | 72 | SEQ ID NO: 33 | ZNF568 '405 |
| ZNF542 | 19 | 56368525 | 56368610 | 86 | SEQ ID NO: 34 | ZNF542 '525 |
| ZNF542 | 19 | 56368502 | 56368591 | 90 | SEQ ID NO: 35 | ZNF542 '502 |
| ZNF471 | 19 | 56507527 | 56507675 | 149 | SEQ ID NO: 36 | ZNF471 '527 |
| ZNF471 | 19 | 56507558 | 56507675 | 118 | SEQ ID NO: 37 | ZNF471 '558 |
| ZNF471 | 19 | 56507662 | 56507750 | 89 | SEQ ID NO: 38 | ZNF471 '662 |
| ZNF132 | 19 | 58440268 | 58440435 | 168 | SEQ ID NO: 39 | ZNF132 '268 |
| ZNF132 | 19 | 55440415 | 58440523 | 109 | SEQ ID NO: 40 | ZNF132 '415 |
| JAM2 | 21 | 25640320 | 25640399 | 80 | SEQ ID NO: 41 | JAM2 '320 |
| ZNF492 | 19 | 22634069 | 22634174 | 106 | SEQ ID NO: 42 | ZNF492 '069 |
| CNRIP1 | 2 | 68319272 | 68319342 | 71 | SEQ ID NO: 43 | CNRIP1 '272 |
| ADAMTS2 | 5 | 179344328 | 179344412 | 85 | SEQ ID NO: 44 | ADAMTS2 '328 |

TABLE 8

Combination of 2 DMRs

| gene name | chr | start site | end site |
|---|---|---|---|
| ZNF471 | 19 | 56507558 | 56507675 |
| FGF14 | 13 | 102394577 | 102394651 |

TABLE 9

Combination of 3 DMRs

| gene name | chr | start site | end site |
|---|---|---|---|
| ZNF471 | 19 | 56507558 | 56507675 |
| FGF14 | 13 | 102394577 | 102394651 |
| PDGFD | 11 | 104163388 | 104163503 |

TABLE 10

Combination of 5 DMRs

| gene name | chr | start site | end site |
|---|---|---|---|
| ZNF471 | 19 | 56507558 | 56507675 |
| FGF14 | 13 | 102394577 | 102394651 |
| PDGFD | 11 | 104163388 | 104163503 |
| ZNF471 | 19 | 56507527 | 56507675 |
| ADAMTS2 | 5 | 179344284 | 179344383 |

TABLE 11

Combination of 8 DMRs

| gene name | chr | start site | end site |
|---|---|---|---|
| ZNF471 | 19 | 56507558 | 56507675 |
| FGF14 | 13 | 102394577 | 102394651 |
| PDGFD | 11 | 104163388 | 104163503 |
| ZNF471 | 19 | 56507527 | 56507675 |
| ADAMTS2 | 5 | 179344284 | 179344383 |
| ADAMTS2 | 5 | 179344254 | 179344348 |
| ZNF492 | 19 | 22634069 | 22634174 |
| ST6GALNAC5 | 1 | 76868456 | 76868525 |

TABLE 12

Combination of 15 DMRs

| gene name | chr | start site | end site |
|---|---|---|---|
| ZNF471 | 19 | 56507558 | 56507675 |
| FGF14 | 13 | 102394577 | 102394651 |
| PDGFD | 11 | 104163388 | 104163503 |
| ZNF471 | 19 | 56507527 | 56507675 |
| ADAMTS2 | 5 | 179344284 | 179344383 |
| ADAMTS2 | 5 | 179344254 | 179344348 |
| ZNF492 | 19 | 22634069 | 22634174 |
| ST6GALNAC5 | 1 | 76868456 | 76868525 |
| ZNF542 | 19 | 56368502 | 56368591 |
| LONRF2 | 2 | 100321281 | 100321395 |
| ZNF132 | 19 | 58440415 | 58440523 |
| PDGFD | 11 | 104163921 | 104164058 |
| ZNF132 | 19 | 58440268 | 58440435 |
| CNRIP1 | 2 | 68319272 | 68319342 |
| ALK | 2 | 29921434 | 29921541 |

In various embodiments, a methylation biomarker can be or include one or more individual nucleotides (e.g., a single individual cysteine residue in the context of CpG) or a plurality of individual cysteine residues (e.g., of a plurality of CpGs) present within one or more methylation loci (e.g, one or more DMRs) provided herein. Thus, in certain embodiments a methylation biomarker is or includes methylation status of a plurality of individual methylation sites.

In various embodiments, a methylation biomarker is, includes, or is characterized by change in methylation status that is a change in the methylation of one or more methylation sites within one or more methylation loci (e.g., one or more DMRs). In various embodiments, a methylation biomarker is or includes a change in methylation status that is a change in the number of methylated sites within one or more methylation loci (e.g., one or more DMRs). In various embodiments, a methylation biomarker is or includes a change in methylation status that is a change in the frequency of methylation sites within one or more methylation loci (e.g., one or more DMRs). In various embodiments, a methylation biomarker is or includes a change in methylation status that is a change in the pattern of methylation sites within one or more methylation loci (e.g., one or more DMRs).

In various embodiments, methylation status of one or more methylation loci (e.g., one or more DMRs) is expressed as a fraction or percentage of the one or more methylation loci (e.g., the one or more DMRs) present in a sample that are methylated, e.g., as a fraction of the number of individual DNA strands of DNA in a sample that are methylated at one or more particular methylation loci (e.g., one or more particular DMRs). Those of skill in the art will appreciate that, in some instances, the fraction or percentage of methylation can be calculated from the ratio of methylated DMRs to unmethylated DMRs for one or more analyzed DMRs, e.g., within a sample.

In various embodiments, methylation status of one or more methylation loci (e.g., one or more DMRs) is compared to a reference methylation status value and/or to methylation status of the one or more methylation loci (e.g., one or more DMRs) in a reference sample. In certain instances, a reference is a non-contemporaneous sample from the same source, e.g., a prior sample from the same source, e.g., from the same subject. In certain instances, a reference for the methylation status of one or more methylation loci (e.g., one or more DMRs) is the methylation status of the one or more methylation loci (e.g., one or more DMRs) in a sample (e.g., a sample from a subject), or a plurality of samples, known to represent a particular state (e.g., a cancer state or a non-cancer state). Thus, a reference can be or include one or more predetermined thresholds, which thresholds can be quantitative (e.g., a methylation value) or qualitative. In certain instances, a reference for methylation status of a DMR is the methylation status of a nucleotide or plurality of nucleotides (e.g., a plurality of contiguous oligonucleotides) present in the same sample that does not include nucleotides of the DMR. Those of skill in the art will appreciate that a reference measurement is typically produced by measurement using a methodology identical to, similar to, or comparable to that by which the non-reference measurement was taken.

Without wishing to be bound by any particular scientific theory, FIG. 20 provides a schematic of one possible mechanism by which hypermethylation or hypomethylation of a regulatory sequence of gene can impact expression. As shown in FIG. 20, hypomethylation can result in increased expression and/or hypermethylation can result in suppression of expression. In various instances, increased methylation of express-regulatory regions, such as promoter regions and enhancer regions, as compared to a reference can reduce or silence expression of an operably linked gene, e.g., of an operably linked gene that typically acts to suppress cancer. In various embodiments, decreased methylation of expression-regulatory regions, such as promoter regions and enhancer regions, as compared to a reference can increase expression of an operably linked gene, e.g., of an operably linked gene having an activity that contributes to oncogenesis. Without wishing to be bound by any particular scientific theory, DNA methylation may provide a more chemically and biologically stable indicator of cancer status than RNA expression or protein expression per se.

Methylation is typically thought to be highly tissue-specific, providing a dimension of information not necessarily present in DNA sequence analysis.

Methylation events that substantially contribute to oncogenesis can occur, e.g., in expression-regulatory regions of DNA (e.g., at a promoter region, enhancer region, transcription factor binding site, CTCF-binding site, CpG island, or other sequence) operably linked with cancer-associated genes such as genes that typically act to suppress cancer. Accordingly, inactivation of genes that typically act to suppress cancer results in or contribute to oncogenesis. Moreover, hyper methylation is typically found at CpG islands.

Cancers

Methods and compositions of the present disclosure are useful for screening for cancer, particularly colorectal cancer. Colorectal cancers include, without limitation, colon cancer, rectal cancer, and combinations thereof. Colorectal cancers include metastatic colorectal cancers and non-metastatic colorectal cancers. Colorectal cancers include cancer located in the proximal part of the colon cancer and cancer located the distal part of the colon.

Colorectal cancers include colorectal cancers at any of the various possible stages known in the art, including, e.g., Stage I, Stage II, Stage III, and Stage IV colorectal cancers (e.g., stages 0, I, IIA, IIB, IIC, IIIA, IIIB, IIIC, IVA, IVB, and IVC). Colorectal cancers include all stages of the Tumor/Node/Metastasis (TNM) staging system. With respect to colorectal cancer, T can refer to whether the tumor grown into the wall of the colon or rectum, and if so by how many layers; N can refer to whether the tumor has spread to lymph nodes, and if so how many lymph nodes and where they are located; and M can refer to whether the cancer has spread to other parts of the body, and if so which parts and to what extent. Particular stages of T, N, and M are known in the art. T stages can include TX, T0, Tis, T1, T2, T3, T4a, and T4b; N stages can include NX, N0, N1a, N1b, N1c, N2a, and N2b; M stages can include M0, M1a, and M1b. Moreover, grades of colorectal cancer can include GX, G1, G2, G3, and G4. Various means of staging cancer, and colorectal cancer in particular, are well known in the art summarized, e.g., on the world wide web at cancer.net/cancer-types/colorectal-cancer/stages.

In certain instances, the present disclosure includes screening of early stage colorectal cancer. Early stage colorectal cancers can include, e.g., colorectal cancers localized within a subject, e.g., in that they have not yet spread to lymph nodes of the subject, e.g., lymph nodes near to the cancer (stage N0), and have not spread to distant sites (stage M0). Early stage cancers include colorectal cancers corresponding to, e.g., Stages 0 to II C.

Thus, colorectal cancer s of the present disclosure include, among other things, pre-malignant colorectal cancer and malignant colorectal cancer. Methods and compositions of the present disclosure are useful for screening of colorectal cancer in all of its forms and stages, including without limitation those named herein or otherwise known in the art, as well as all subsets thereof. Accordingly, the person of skill in art will appreciate that all references to colorectal cancer provided here include, without limitation, colorectal cancer in all of its forms and stages, including without limitation those named herein or otherwise known in the art, as well as all subsets thereof.

Subjects and Samples

A sample analyzed using methods and compositions provided herein can be any biological sample and/or any sample including nucleic acid. In various particular embodiments, a sample analyzed using methods and compositions provided herein can be a sample from a mammal. In various particular embodiments, a sample analyzed using methods and compositions provided herein can be a sample from a human subject. In various particular embodiments, a sample analyzed using methods and compositions provided herein can be a sample form a mouse, rat, pig, horse, chicken, or cow.

In various instances, a human subject is a subject diagnosed or seeking diagnosis as having, diagnosed as or seeking diagnosis as at risk of having, and/or diagnosed as or seeking diagnosis as at immediate risk of having, a cancer such as a colorectal cancer. In various instances, a human subject is a subjected identified as a subject in need of colorectal cancer screening. In certain instances, a human subject is a subjected identified as in need of colorectal cancer screening by a medical practitioner. In various instances, a human subject is identified as in need of colorectal cancer screening due to age, e.g., due to an age equal to or greater than 50 years, e.g., an age equal to or greater than 50, 55, 60, 65, 70, 75, 80, 85, or 90 years. In various instances, a human subject is a subject not diagnosed as having, not at risk of having, not at immediate risk of having, not diagnosed as having, and/or not seeking diagnosis for a cancer such as a colorectal cancer, or any combination thereof.

A sample from a subject, e.g., a human or other mammalian subject, can be a sample of, e.g., blood, blood component, cfDNA, ctDNA, stool, or colorectal tissue. In some particular embodiments, a sample is an excretion or bodily fluid of a subject (e.g., stool, blood, lymph, or urine of a subject) or a colorectal cancer tissue sample. A sample from a subject can be a cell or tissue sample, e.g., a cell or tissue sample that is of a cancer or includes cancer cells, e.g., of a tumor or of a metastatic tissue. In various embodiments, a sample from a subject, e.g., a human or other mammalian subject, can be obtained by biopsy (e.g., fine needle aspiration or tissue biopsy) or surgery.

In various particular embodiments, a sample is a sample of cell-free DNA (cfDNA). cfDNA is typically found in human biofluids (e.g., plasma, serum, or urine) in short, double-stranded fragments. The concentration of cfDNA is typically low, but can significantly increase under particular conditions, including without limitation pregnancy, autoimmune disorder, myocardial infraction, and cancer. Circulating tumor DNA (ctDNA) is the component of circulating DNA specifically derived from cancer cells. ctDNA can be present in human biofluids bound to leukocytes and erythrocytes or not bound to leukocytes and erythrocytes. Various tests for detection of tumor-derived cfDNA are based on detection of genetic or epigenetic modifications that are characteristic of cancer (e.g., of a relevant cancer). Genetic or epigenetic modifications characteristic of cancer can include, without limitation, oncogenic or cancer-associated mutations in tumor-suppressor genes, activated oncogenes, hypermethylation, and/or chromosomal disorders. Detection of genetic or epigenetic modifications characteristic of cancer can confirm that detected cfDNA is ctDNA.

cfDNA and ctDNA provide a real-time or nearly real time metric of the methylation status of a source tissue. cfDNA and ctDNA demonstrate a half-life in blood of about 2 hours, such that a sample taken at a given time provides a relatively timely reflection of the status of a source tissue.

Various methods of isolating nucleic acids from a sample (e.g., of isolating cfDNA from blood or plasma) are known in the art. Nucleic acids can be isolated, e.g., without limitation, standard DNA purification techniques, by direct gene capture (e.g., by clarification of a sample to remove assay-inhibiting agents and capturing a target nucleic acid, if present, from the clarified sample with a capture agent to produce a capture complex, and isolating the capture complex to recover the target nucleic acid).

Methods of Measuring Methylation Status

Methylation status can be measured by a variety of methods known in the art and/or by methods provided herein. Those of skill in the art will appreciate that a method for measuring methylation status can generally be applied to samples from any source and of any kind, and will further be aware of processing steps available to modify a sample into a form suitable for measurement by a given methodology. Methods of measuring methylation status include, without limitation, methods including methylation-status-specific polymerase chain reaction (PCR), methods including nucleic acid sequencing, methods including mass spectrometry, methods including methylation-specific nucleases, methods including mass-based separation, methods including target-specific capture, and methods including methylation-specific oligonucleotide primers. Certain particular assays for methylation utilize a bisulfite reagent (e.g., hydrogen sulfite ions).

Bisulfite reagents can include, among other things, bisulfite, disulfite, hydrogen sulfite, or combinations thereof, which reagents can be useful in distinguishing methylated and unmethylated nucleic acids. Bisulfite interacts differently with cytosine and 5-methylcytosine. In typical bisulfite-based methods, contacting of DNA with bisulfite deaminates unmethylated cytosine to uracil, while methylated cytosine remains unaffected; methylated cytosines, but not unmethylated cytosines, are selectively retained. Thus, in a bisulfite processed sample, uracil residues stand in place of, and thus provide an identifying signal for, unmethylated cytosine residues, while remaining (methylated) cytosine residues thus provide an identifying signal for methylated cytosine residues. Bisulfite processed samples can be analyzed, e.g., by PCR.

Various methylation assay procedures can be used in conjunction with bisulfite treatment to determine methylation status of a target sequence such as a DMR. Such assays can include, among others, Methylation-Specific Restriction Enzyme qPCR, sequencing of bisulfite-treated nucleic acid, PCR (e.g., with sequence-specific amplification), Methylation Specific Nuclease-assisted Minor-allele Enrichment PCR, and Methylation-Sensitive High Resolution Melting. In some embodiments, DMRs are amplified from a bisulfite-treated DNA sample and a DNA sequencing library is prepared for sequencing according to, e.g., an Illumina protocol or transpose-based Nextera XT protocol. In certain embodiments, high-throughput and/or next-generation sequencing techniques are used to achieve base-pair level resolution of DNA sequence, permitting analysis of methylation status.

In various embodiments, methylation status is detected by a method including PCR amplification with methylation-specific oligonucleotide primers (MSP methods), e.g., as applied to bisulfite-treated sample (see, e.g., Herman 1992 Proc. Natl. Acad. Sci. USA 93: 9821-9826, which is herein incorporated by reference with respect to methods of determining methylation status). Use of methylation-status-specific oligonucleotide primers for amplification of bisulfite-treated DNA allows differentiation between methylated and unmethylated nucleic acids. Oligonucleotide primer pairs for use in MSP methods include at least one oligonucleotide primer capable of hybridizing with sequence that includes a methylation cite, e.g., a CpG. An oligonucleotide primer that includes a T residue at a position complementary to a cytosine residue will selectively hybridize to templates in which the cytosine was unmethylated prior to bisulfite treatment, while an oligonucleotide primer that includes a G residue at a position complementary to a cytosine residue will selectively hybridize to templates in which the cytosine was methylated cytosine prior to bisulfite treatment. MSP results can be obtained with or without sequencing amplicons, e.g., using gel electrophoresis. MSP (methylation-specific PCR) allows for highly sensitive detection (detection level of 0.1% of the alleles, with full specificity) of locus-specific DNA methylation, using PCR amplification of bisulfite-converted DNA.

Another method that can be used to determine methylation status after bisulfite treatment of a sample is Methylation-Sensitive High Resolution Melting (MS-HRM) PCR (see, e.g., Hussmann 2018 Methods Mol Biol. 1708:551-571, which is herein incorporated by reference with respect to methods of determining methylation status). MS-HRM is an in-tube, PCR-based method to detect methylation levels at specific loci of interest based on hybridization melting. Bisulfite treatment of the DNA prior to performing MS-HRM ensures a different base composition between methylated and unmethylated DNA, which is used to separate the resulting amplicons by high resolution melting. A unique primer design facilitates a high sensitivity of the assays enabling detection of down to 0.1-1% methylated alleles in an unmethylated background. Oligonucleotide primers for MS-HRM assays are designed to be complementary to the methylated allele, and a specific annealing temperature enables these primers to anneal both to the methylated and the unmethylated alleles thereby increasing the sensitivity of the assays.

Another method that can be used to determine methylation status after bisulfite treatment of a sample is Quantitative Multiplex Methylation-Specific PCR (QM-MSP). QM-MSP uses methylation specific primers for sensitive quantification of DNA methylation (see, e.g., Fackler 2018 Methods Mol Biol. 1708:473-496, which is herein incorporated by reference with respect to methods of determining methylation status). QM-MSP is a two-step PCR approach, where in the first step, one pair of gene-specific primers (forward and reverse) amplifies the methylated and unmethylated copies of the same gene simultaneously and in multiplex, in one PCR reaction. This methylation-independent amplification step produces amplicons of up to $10^9$ copies per µL after 36 cycles of PCR. In the second step, the amplicons of the first reaction are quantified with a standard curve using real-time PCR and two independent fluorophores to detect methylated/unmethylated DNA of each gene in the same well (e.g., 6FAM and VIC). One methylated copy is detectable in 100,000 reference gene copies.

Another method that can be used to determine methylation status after bisulfite treatment of a sample is Methylation Specific Nuclease-assisted Minor-allele Enrichment (MS-NaME) (see, e.g., Liu 2017 Nucleic Acids Res. 45(6): e39, which is herein incorporated by reference with respect to methods of determining methylation status). Ms-NaME is based on selective hybridization of probes to target sequences in the presence of DNA nuclease specific to double-stranded (ds) DNA (DSN), such that hybridization results in regions of double-stranded DNA that are subsequently digested by the DSN. Thus, oligonucleotide probes targeting unmethylated sequences generate local double stranded regions resulting to digestion of unmethylated targets; oligonucleotide probes capable of hybridizing to methylated sequences generate local double-stranded regions that result in digestion of methylated targets, leaving methylated targets intact. Moreover, oligonucleotide probes can direct DSN activity to multiple targets in bisulfite-treated DNA, simultaneously. Subsequent amplification can enrich non-digested sequences. Ms-NaME can be used, either independently or in combination with other techniques provided herein.

Another method that can be used to determine methylation status after bisulfite treatment of a sample is Methylation-sensitive Single Nucleotide Primer Extension (Ms-SNuPE™) (see, e.g., Gonzalgo 2007 Nat Protoc. 2(8):1931-6, which is herein incorporated by reference with respect to methods of determining methylation status). In Ms-SNuPE, strand-specific PCR is performed to generate a DNA template for quantitative methylation analysis using Ms-SNuPE. SNuPE is then performed with oligonucleotide(s) designed to hybridize immediately upstream of the CpG site(s) being interrogated. Reaction products can be electrophoresed on polyacrylamide gels for visualization and quantitation by phosphor-image analysis. Amplicons can also carry a directly or indirectly detectable labels such as a fluorescent label, radionuclide, or a detachable molecule fragment or other entity having a mass that can be distinguished by mass spectrometry. Detection may be carried out and/or visualized by means of, e.g., matrix assisted laser desorption/ionization mass spectrometry (MALDI) or using electron spray mass spectrometry (ESI).

Certain methods that can be used to determine methylation status after bisulfite treatment of a sample utilize a first oligonucleotide primer, a second oligonucleotide primer, and an oligonucleotide probe in an amplification-based method. For instance, the oligonucleotide primers and probe can be used in a method of real-time polymerase chain reaction (PCR) or droplet digital PCR (ddPCR). In various instances, the first oligonucleotide primer, the second oligonucleotide primer, and/or the oligonucleotide probe selectively hybridize methylated DNA and/or unmethylated DNA, such that amplification or probe signal indicate methylation status of a sample.

Other bisulfite-based methods for detecting methylation status (e.g., the presence of level of 5-methylcytosine) are disclosed, e.g., in Frommer (1992 Proc Natl Acad Sci USA. 1; 89(5):1827-31, which is herein incorporated by reference with respect to methods of determining methylation status).

Certain methods that can be used to determine methylation status do not include bisulfite treatment of a sample. For instance, changes in methylation status can be detected by a PCR-based process in which DNA is digested with one or more methylation-sensitive restriction enzymes (MSREs) prior to PCR amplification (e.g., by MSRE-qPCR). Typically, MSREs have recognition sites that include at least one CpG motif, such that activity of the MSRE is blocked from cleaving a possible recognition site if the site includes 5-methylcytosine. (see, e.g., Beikircher 2018 Methods Mol Biol. 1708:407-424, which is herein incorporated by reference with respect to methods of determining methylation status). Thus, MSREs selectively digest nucleic acids based upon methylation status of the recognition site of the MSRE; they can digest DNA at MSRE recognition sites that are unmethylated, but not digest DNA in MSRE recognition sites that are methylated. In certain embodiments, an aliquot of sample can be digested with MSREs, generating a processed sample in which unmethylated DNA has been cleaved by the MSREs, such that, the proportion of uncleaved and/or amplifiable DNA with at least one methylated site within MSRE recognition sites (e.g., at least one methylated site within each MSRE recognition site of the DNA molecule) is increased relative to uncleaved and/or amplifiable DNA that did not include at least one methylated site within MSRE recognition sites (e.g., did not include at least one methylated site within each MSRE recognition site of the DNA molecule). Uncleaved sequences of a restriction-enzyme-digested sample can then be preamplified, e.g, in PCR, and quantified e.g. by qPCR, real-time PCR, or digital PCR. Oligonucleotide primers for MSRE-qPCR amplify regions that include one or more MSRE cleavage sites, and/or a plurality of MSRE cleavage sites. Amplicons including a plurality of MSRE cleavage sites are typically more likely to yield robust results. The number of cleavage sites within a DMR amplicon, and in some instances the resulting robustness of methylation status determination for the DMR, can be increased by design of DMRs that include a plurality of MSRE recognition sites (as opposed to a single recognition site) in a DMR amplicon. In various instances, a plurality of MSREs can be applied to the same sample, including, e.g., two or more of AciI, Hin6I, HpyCH4IV, and HpaII (e.g., including AciI, Hin6I, and HpyCH4IV). A plurality of MSREs (e.g., the combination of AciI, Hin6I, HpyCH4IV, and HpaII, or the combination of AciI, Hin6I, and HpyCH4IV) can provide improved frequency of MSRE recognition sites within DMR amplicons.

MSRE-qPCR can also include a pre-amplification step following sample digestion by MSREs but before qPCR in order to improve the amount of available sample, given the low prevalence of cfDNA in blood.

In certain MSRE-qPCR embodiments, the amount of total DNA is measured in an aliquot of sample in native (e.g., undigested) form using, e.g., real-time PCR or digital PCR.

Various amplification technologies can be used alone or in conjunction with other techniques described herein for detection of methylation status. Those of skill in the art, having reviewed the present specification, will understand how to combine various amplification technologies known in the art and/or described herein together with various other technologies for methylation status determination known in the art and/or provided herein. Amplification technologies include, without limitation, PCR, e.g., quantitative PCR (qPCR), real-time PCR, and/or digital PCR. Those of skill in the art will appreciate that polymerase amplification can multiplex amplification of multiple targets in a single reaction. PCR amplicons are typically 100 to 2000 base pairs in length. In various instances, an amplification technology is sufficient to determine methylations status.

Digital PCR (dPCR) based methods involve dividing and distributing a sample across wells of a plate with 96-, 384-, or more wells, or in individual emulsion droplets (ddPCR) e.g., using a microfluidic device, such that some wells include one or more copies of template and others include no copies of template. Thus, the average number of template molecules per well is less than one prior to amplification. The number of wells in which amplification of template occurs provides a measure of template concentration. If the sample has been contacted with MSRE, the number of wells in which amplification of template occurs provides a measure of the concentration of methylated template.

In various embodiments a fluorescence-based real-time PCR assay, such as MethyLight™, can be used to measure methylation status (see, e.g., Campan 2018 Methods Mol Biol. 1708:497-513, which is herein incorporated by reference with respect to methods of determining methylation status) MethyLight is a quantitative, fluorescence-based, real-time PCR method to sensitively detect and quantify DNA methylation of candidate regions of the genome. MethyLight is uniquely suited for detecting low-frequency methylated DNA regions against a high background of unmethylated DNA, as it combines methylation-specific priming with methylation-specific fluorescent probing. Additionally, MethyLight can be combined with Digital PCR, for the highly sensitive detection of individual methylated molecules, with use in disease detection and screening.

Real-time PCR-based methods for use in determining methylation status typically include a step of generating a standard curve for unmethylated DNA based on analysis of external standards. A standard curve can be constructed from at least two points and can permit comparison of a real-time Ct value for digested DNA and/or a real-time Ct value for undigested DNA to known quantitative standards. In particular instances, sample Ct values can be determined for MSRE-digested and/or undigested samples or sample aliquots, and the genomic equivalents of DNA can be calculated from the standard curve. Ct values of MSRE-digested and undigested DNA can be evaluated to identify amplicons digested (e.g., efficiently digested; e.g., yielding a Ct value of 45). Amplicons not amplified under either digested or undigested conditions can also be identified. Corrected Ct values for amplicons of interest can then be directly compared across conditions to establish relative differences in methylation status between conditions. Alternatively or additionally, delta-difference between the Ct values of digested and undigested DNA can be used to establish relative differences in methylation status between conditions.

Methods of measuring methylation status can include, without limitation, massively parallel sequencing (e.g., next-generation sequencing) to determine methylation state, e.g., sequencing by—synthesis, real-time (e.g., single-molecule) sequencing, bead emulsion sequencing, nanopore sequencing, or other sequencing techniques known in the art. In some embodiments, a method of measuring methylation status can include whole-genome sequencing, e.g., with base-pair resolution.

In certain particular embodiments, MSRE-qPCR, among other techniques, can be used to determine the methylation status of a colorectal cancer methylation biomarker that is or includes a single methylation locus. In certain particular embodiments, MSRE-qPCR, among other techniques, can be used to determine the methylation status of a colorectal cancer methylation biomarker that is or includes two or more methylation loci. In certain particular embodiments, MSRE-qPCR, among other techniques, can be used to determine the methylation status of a colorectal cancer methylation biomarker that is or includes a single differentially methylated region (DMR). In certain particular embodiments, MSRE-qPCR, among other techniques, can be used to determine the methylation status of a colorectal cancer methylation biomarker that is or includes two or more DMRs. In certain particular embodiments, MSRE-qPCR, among other techniques, can be used to determine the methylation status of a colorectal cancer methylation biomarker that is or includes a single methylation site. In certain particular embodiments, MSRE-qPCR, among other techniques, can be used to determine the methylation status of a colorectal cancer methylation biomarker that is or includes two or more methylation sites. In various embodiments, a colorectal cancer methylation biomarker can be any colorectal cancer methylation biomarker provided herein. The present disclosure includes, among other things, oligonucleotide primer pairs for amplification of DMRs, e.g., for amplification of DMRs identified in Table 7.

In certain particular embodiments, a cfDNA sample is derived from subject plasma and contacted with MSREs that are or include one or more of AciI, Hin6I, HpyCH4IV, and HpaII (e.g., AciI, Hin6I, and HpyCH4IV). The digested sample can be preamplified with oligonucleotide primer pairs of one or more DMRs, e.g., with one or more oligonucleotide primer pairs provided in Table 13. Digested DNA, e.g., preamplified digested DNA, can be quantified with qPCR with oligonucleotide primer pairs of one or more DMRs, e.g., with one or more oligonucleotide primer pairs provided in Table 13. qPCR ct values can then be determined and used to determine methylation status of each DMR amplicon.

It will be appreciated by those of skill in the art that oligonucleotide primer pairs provided in Table 13 can be used in accordance with any combination of colorectal cancer methylation biomarkers identified herein. The skilled artisan will be aware that the oligonucleotide primer pairs of Table 13 may be individual included or not included in a given analysis in order to analyze a particular desire combination of DRMs.

The person of skill in the art will further appreciate that while other oligonucleotide primer pairs may be used, selection and pairing of oligonucleotide primers to produce useful DMR amplicons is non-trivial and represents a substantial contribution.

Those of skill in the art will further appreciate that methods, reagents, and protocols for qPCR are well-known in the art. Unlike traditional PCR, qPCR is able to detect the production of amplicons over time in amplification (e.g., at the end of each amplification cycle), often by use of an amplification-responsive fluorescence system, e.g., in combination with a thermocycler with fluorescence-detection capability. Two common types of fluorescent reporters used in qPCR include (i) double-stranded DNA binding dyes that fluoresce substantially more brightly when bound than when unbound; and (ii) labeled oligonucleotides (e.g., labeled oligonucleotide primers or labeled oligonucleotide probes).

Those of skill in the art will appreciate that in embodiments in which a plurality of methylation loci (e.g., a plurality of DMRs) are analyzed for methylation status in a method of screening for colorectal cancer provided herein, methylation status of each methylation locus can be measured or represented in any of a variety of forms, and the methylation statuses of a plurality of methylation loci (preferably each measured and/or represented in a same, similar, or comparable manner) be together or cumulatively analyzed or represented in any of a variety of forms. In various embodiments, methylation status of each methylation locus can be measured as a ct value. In various embodiments, methylation status of each methylation locus can be represented as the difference in ct value between a measured sample and a reference. In various embodiments, methylation status of each methylation locus can be represented as a qualitative comparison to a reference, e.g., by identification of each methylation locus as hypermethylated or not hypermethyated.

In some embodiments in which a single methylation locus is analyzed, hypermethylation of the single methylation locus constitutes a diagnosis that a subject is suffering from or possibly suffering from colorectal cancer, while absence of hypermethylation of the single methylation locus constitutes a diagnosis that the subject is likely not suffering from colorectal cancer. In some embodiments, hypermethylation of a single methylation locus (e.g., a single DMR) of a plurality of analyzed methylation loci constitutes a diagnosis that a subject is suffering from or possibly suffering from colorectal cancer, while the absence of hypermethylation at any methylation locus of a plurality of analyzed methylation loci constitutes a diagnosis that a subject is likely not suffering from colorectal cancer. In some embodiments, hypermethylation of a determined percentage (e.g., a predetermined percentage) of methylation loci (e.g., at least 10% (e.g., at least 10%, at least 20%, at least 30%, at least 40%, at least 50%, at least 60%, at least 70%, at least 80%, at least 90%, or 100%)) of a plurality of analyzed methylation loci constitutes a diagnosis that a subject is suffering from or possibly suffering from colorectal cancer, while the absence of hypermethylation of a determined percentage (e.g., a predetermined percentage) of methylation loci (e.g., at least 10% (e.g., at least 10%, at least 20%, at least 30%, at least 40%, at least 50%, at least 60%, at least 70%, at least 80%, at least 90%, or 100%)) of a plurality of analyzed methylation loci constitutes a diagnosis that a subject is not likely suffering from colorectal cancer. In some embodiments, hypermethylation of a determined number (e.g., a predetermined number) of methylation loci (e.g., at least 1, 2, 3, 4, 5, 6, 7, 8, 9, 10, 11, 12, 13, 14, 15, 16, 17, 18, 19, 20, 21, 22, 23, 24, 25, 26, 27, or 28 DMRs) of a plurality of analyzed methylation loci (e.g., 2, 3, 4, 5, 6, 7, 8, 9, 10, 11, 12, 13, 14, 15, 16, 17, 18, 19, 20, 21, 22, 23, 24, 25, 26, 27, or 28 DMRs) constitutes a diagnosis that a subject is suffering from or possibly suffering from colorectal cancer, while the absence of hypermethylation of a determined number (e.g., a predetermined number) of methylation loci (e.g., at least 1, 2, 3, 4, 5, 6, 7, 8, 9, 10, 11, 12, 13, 14, 15, 16, 17, 18, 19, 20, 21, 22, 23, 24, 25, 26, 27, or 28 DMRs) of a plurality of analyzed methylation loci (e.g., 2, 3, 4, 5, 6, 7, 8, 9, 10, 11, 12, 13, 14, 15, 16, 17, 18, 19, 20, 21, 22, 23, 24, 25, 26, 27, or 28 DMRs) constitutes a diagnosis that a subject is not likely suffering from colorectal cancer.

In some embodiments, methylation status of a plurality of methylation loci (e.g., a plurality of DMRs) is measured qualitatively or quantitatively and the measurement for each of the plurality of methylation loci are combined to provide a diagnosis. In some embodiments, the qualitative of quantitatively measured methylation status of each of a plurality of methylation loci is individually weighted, and weighted values are combined to provide a single value that can be comparative to a reference in order to provide a diagnosis. To provide but one example of such an approach, support vector machine (SVM) algorithm can be used to analyze the methylation statuses of a plurality of methylation loci of the present disclosure to produce a diagnosis. At least one objective of the support vector machine algorithm is to identify a hyperplane in an N-dimensional space (N—the number of features) that distinctly classifies the data points with the objective to find a plane that has the maximum margin, i.e. the maximum distance between data points of both classes. As discussed in the present Examples, an SVM model is built on marker values (e.g., ct values) derived from a training sample set (e.g., the first subject group and/or the second subject group) that are transformed to support vector values upon which a prediction is made. In application of the SVM model to new samples, samples will be mapped onto vectoral space the model and categorized as having a probability of belonging to the first condition or the second condition, e.g., based on each new sample's location relative to the gap between the two conditions. Those of skill in the art will appreciate that, once relevant compositions and methods have been identified, vector values can be used in conjunction with an SVM algorithm defined by predict( ) function of R-package (see Hypertext Transfer Protocol Secure (HTTPS):/cran.r-project.org/web/packages/e1071/index.html, the SVM of which is hereby incorporated by reference) to easily generate a prediction on a new sample. Accordingly, with compositions and methods for colorectal cancer diagnosis disclosed herein in hand (and only then), generation of a predictive model utilizing algorithm input information in combination to predict( ) function of R-package (see Hypertext Transfer Protocol Secure (HTTPS):/cran.r-project.org/web/packages/e1071/index.html, the SVM of which is hereby incorporated by reference) to provide colorectal cancer diagnosis would be straightforward. By way of example, one non-limiting example of SVM vectors for use in diagnosis of colorectal cancer by analysis of methylation status of a plurality of DMRs provided herein is provided in Table 17. Those of skill in the art will appreciate that, with the present disclosure in hand, generation of SVM vectors can be accomplished according to methods provided herein and otherwise known in the art.

TABLE 13

Colorectal cancer DMR oligonucleotide primer pairs, e.g., for MSRE-qPCR

| gene name | Fp_Seq | Rp_Seq | Fp SEQ ID | Rp SEQ ID | Loci Reference Name |
|---|---|---|---|---|---|
| ALK | CCTCCTCACCATCATCAGCGCCC | GGTACCTCCCGCCGCCTCTGTTC | 45 | 46 | ALK '434 |
| CNRIP1 | GCGTGCTGGGTTTAATCTTCACCTCAA | ACGGCCCGGTCTTTTACAAGGTGG | 47 | 48 | CNRIP1 '232 |
| LONRF2 | AGGAAGCAAAGTGACCCCTAAGCCT | GGTCCGCCTCCCCTACACCT | 49 | 50 | LORNF2 '281 |
| LONRF2 | CTCTCAGTCCCGCCGGCTTAGGTA | GCAAGAGACGCGGACCTGGAGC | 51 | 52 | LORNF2 '387 |
| ADAMTS2 | CCACTGCGAAGGGAAGGGGCA | CCCTGTTAACGCCCCTTCCCGGTT | 53 | 54 | ADAMTS2 '254 |
| ADAMTS2 | GCGACCCCAGAAAGCCAGCCT | AACGGCTGGGGAGTCGCGGA | 55 | 56 | ADAMTS2 '284 |
| FGF14 | CAACGGAAACTTCCCGCGCTAC | CTCGCCGGGGCTTCGCTAC | 57 | 58 | FGF14 '577 |
| DMRT1 | CAAAGCGTCTGGGGCGCTAGT | ACTTCTTGCTCCCGGCACCCAGGTC | 59 | 60 | DMRT1 '934 |
| ST6GALNAC5 | CGCTCAGCCGCTCTCCTCTTCTCT | AGCGCTAAACACACTGCCAGACCA | 61 | 62 | ST6GALNAC5 '456 |

TABLE 13-continued

Colorectal cancer DMR oligonucleotide primer pairs, e.g., for MSRE-qPCR

| gene name | Fp_Seq | Rp_Seq | Fp SEQ ID | Rp SEQ ID | Loci Reference Name |
|---|---|---|---|---|---|
| MCIDAS | GGGTTCGGAGCGTGCAAAAGGTGA | GAACAGTTCAGTGCATCCCCGCCC | 63 | 64 | MCIDAS '855 |
| MCIDAS | GCGCCCCACTTACATCCAGCACC | ACGTGACATTGACCCAGAAACAGGAGGA | 65 | 66 | MCIDAS '003 |
| PDGFD | AACGTCTATCACCCAGGGAAAGCT | TCCCGGAGTTGGCGAAAGTTGCAA | 67 | 68 | PDGFD '388 |
| PDGFD | GGTGCATTTGGCATCAGCGACTAGAGAC | CATTAGCACAGCGACCCGGGCCAG | 69 | 70 | PDGFD '921 |
| GSG1L | CCGAAAGAAATCCGAGCCAGGGTGA | GGTTTTGTTGCCCCACGTCC | 71 | 72 | GSG1L '861 |
| ZNF492 | CGAGAGAGGGGAAGGGGCTGGTTG | CGAACTTGGGGCGCAGATTGTGG | 73 | 74 | ZNF492 '499 |
| ZNF568 | GCCCAAGCCTCACCCTCACACAG | CGAACCATCCCTCCGCGCCA | 75 | 76 | ZNF568 '252 |
| ZNF568 | GGTCGCCTTCACCCAGCATCTCAG | CAGCGTCACCTGCCGGAAACACC | 77 | 78 | ZNF568 '405 |
| ZNF542 | CCAGAGGCCCAGGGATCCGTTCAG | ACGCGAGCATTCTTGTAAGGCACCC | 79 | 80 | ZNF542 '525 |
| ZNF542 | GGGAGGAGTGGGCGGCTGAATGG | GCACCCGCCACCTCCAAACTCAG | 81 | 82 | ZNF542 '502 |
| ZNF471 | CCCCACGCGTACTCACACCGAAG | GCGGGTAAGAGCAGGAGTGTG | 83 | 84 | ZNF471 '527 |
| ZNF471 | GTCGCGCGTTTCCCTCCCAG | GCGGGTAAGAGCGAGGAGTGTG | 85 | 86 | ZNF471 '558 |
| ZNF471 | CTGCTCTTACCCGCCGGAACCCTG | GAGGGACCTTAGAGCAGAGCGGGC | 87 | 88 | ZNF471 '662 |
| ZNF132 | CTACTGCTAGGTCGTTGCCAAGG | TGATTGGCCAGCGTCTTACACTCCG | 89 | 90 | ZNF132 '268 |
| ZNF132 | GTGTAAGACGCTGGCCAATCACA | ACAACGCGGTCCCTTCAGAAGCAG | 91 | 92 | ZNF132 '415 |
| JAM2 | CCGCGTGGTCTGGGCTCTGTAG | GAATTCCCTCCACCTCCGCCCAC | 93 | 94 | JAM2 '320 |
| ZNF492 | CAACGTTAAAGGCAAACACCTTCTGC | GGCCGAATGAGGACAGAGTGACAG | 95 | 96 | ZNF492 '069 |
| CNRIP1 | GCCGGTGAGCAGCTTGATGGT | ACGGCCCGGTCTTTTACAAGG | 97 | 98 | CNRIP1 '272 |
| ADAMTS2 | CGGGAGGGCGTTAACAGGGC | TCTTGGCAGGCAAGGTCTCCGGAG | 99 | 100 | ADAMTS2 '328 |

Applications

Methods and compositions of the present disclosure can be used in any of a variety of applications. For example, methods and compositions of the present disclosure can be used to screen, or aid in screening for, colorectal cancer. In various instances, screening using methods and compositions of the present disclosure can detect any stage of colorectal cancer, including without limitation early-stage colorectal cancer. In some embodiments, colorectal cancer screening using methods and compositions of the present disclosure is applied to individuals 50 years of age or older, e.g., 50, 55, 60, 65, 70, 75, 80, 85, or 90 years or older. In some embodiments, colorectal cancer screening using methods and compositions of the present disclosure is applied to individuals 20 years of age or older, e.g., 20, 25, 30, 35, 40, 45, 50, 55, 60, 65, 70, 75, 80, 85, or 90 years or older. In some embodiments, colorectal cancer screening using methods and compositions of the present disclosure is applied to individuals 20 to 50 years of age, e.g., 20 to 30 years of age, 20 to 40 years of age, 20 to 50 years of age, 30 to 40 years of age, 30 to 50 years of age, or 40 to 50 years of age. In various embodiments, colorectal cancer screening using methods and compositions of the present disclosure is applied to individuals experiencing abdominal pain or discomfort, e.g., experiencing undiagnosed or incompletely diagnosed abdominal pain or discomfort. In various embodiments, colorectal cancer screening using methods and compositions of the present disclosure is applied to individuals experiencing no symptoms likely to be associated with colorectal cancer. Thus, in certain embodiments, colorectal cancer screening using methods and compositions of the present disclosure is fully or partially preventative or prophylactic, at least with respect to later or non-early stages of colorectal cancer.

In various embodiments, colorectal cancer screening using methods and compositions of the present disclosure can be applied to an asymptomatic human subject. As used herein, a subject can be referred to as "asymptomatic" if the subject does not report, and/or demonstrate by non-invasively observable indicia (e.g., without one, several, or all of device-based probing, tissue sample analysis, bodily fluid analysis, surgery, or colorectal cancer screening), sufficient characteristics of colorectal cancer to support a medically reasonable suspicion that the subject is likely suffering from colorectal cancer, and/or from cancer. Detection of early stage colorectal cancer is particularly likely in asymptomatic individuals screened in accordance with methods and compositions of the present disclosure.

In various embodiments, colorectal cancer screening using methods and compositions of the present disclosure can be applied to a symptomatic human subject. As used herein, a subject can be referred to as "symptomatic" if the subject report, and/or demonstrates by non-invasively observable indicia (e.g., without one, several, or all of device-based probing, tissue sample analysis, bodily fluid analysis, surgery, or colorectal cancer screening), sufficient characteristics of colorectal cancer to support a medically reasonable suspicion that the subject is likely suffering from colorectal cancer, and/or from cancer. Symptoms of colorectal cancer can include, without limitation, change in bowel habits (diarrhea, constipation, or narrowing of the stool) that are persistent (e.g., lasting more than 3 days), feeling of a need to have a bowel movement which feeling is not relieved upon bowel movement, rectal bleeding (e.g., with bright red blood), blood in stool (which can cause stool to appear dark), abdominal cramping, abdominal pain, weakness, fatigue, unintended weight loss, anemia, and combinations thereof. Those of skill in the art will appreciate that individual symptoms that would not alone indicate or raise a suspicion of colorectal cancer may do so when presented in combination, e.g., a combination of abdominal cramping and blood in stool, to provide but one non-limiting example.

Those of skill in the art will appreciate that regular, preventative, and/or prophylactic screening for colorectal cancer improves diagnosis of colorectal cancer, including and/or particularly early stage cancer. As noted above, early stage cancers include, according to at least one system of cancer staging, Stages 0 to II C of colorectal cancer. Thus, the present disclosure provides, among other things, methods and compositions particularly useful for the diagnosis and treatment of early stage colorectal cancer. Generally, and particularly in embodiments in which colorectal cancer screening in accordance with the present disclosure is carried out annually, and/or in which a subject is asymptomatic at time of screening, methods and compositions of the present invention are especially likely to detect early stage colorectal cancer.

In various embodiments colorectal cancer screening in accordance with the present disclosure is performed once for a given subject or multiple times for a given subject. In various embodiments, colorectal cancer screening in accordance with the present disclosure is performed on a regular basis, e.g., every six months, annually, every two years, every three years, every four years, every five years, or every ten years.

In various embodiments, screening for colorectal cancer using methods and compositions disclosed herein will be provide a diagnosis of colorectal cancer. In other instances, screening for colorectal cancer using methods and compositions disclosed herein will be indicative of colorectal cancer diagnosis but not definitive for colorectal cancer diagnosis. In various instances in which methods and compositions of the present disclosure are used to screen for colorectal cancer, screening using methods and compositions of the present disclosure can be followed by a further diagnosis-confirmatory assay, which further assay can confirm, support, undermine, or reject a diagnosis resulting from prior screening, e.g., screening in accordance with the present disclosure. As used herein, a diagnosis-confirmatory assay can be a colorectal cancer assay that provides a diagnosis recognized as definitive by medical practitioners, e.g., a colonoscopy-based diagnosed, or a colorectal cancer assay that substantially increases or decreases the likelihood that a prior diagnosis was correct, e.g., a diagnosis resulting from screening in accordance with the present disclosure. Diagnosis-confirmatory assays could include existing screening technologies, which are generally in need of improvement with respect to one or more of sensitivity, specificity, and non-invasiveness, particularly in the detection of early stage colorectal cancers.

In some instances, a diagnosis-confirmatory assay is a test that is or includes a visual or structural inspection of subject tissues, e.g., by colonoscopy. In some embodiments, colonoscopy includes or is followed by histological analysis. Visual and/or structural assays for colorectal cancer can include inspection of the structure of the colon and/or rectum for any abnormal tissues and/or structures. Visual and/or structural inspection can be conducted, for example, by use of a scope via the rectum or by CT-scan. In some instances, a diagnosis-confirmatory assay is a colonoscopy, e.g., including or followed by histological analysis. According to some reports, colonoscopy is currently the predominant and/or most relied upon diagnosis-confirmatory assay.

Another visual and/or structural diagnosis confirmatory assay based on computer tomography (CT) is CT colonography, sometimes referred to as virtual colonoscopy. A CT scan utilizes numerous x-ray images of the colon and/or rectum to produce dimensional representations of the colon. Although useful as a diagnosis-confirmatory assay, some reports suggest that CT colonography is not sufficient for replacement of colonoscopy, at least in part because a medical practitioner has not physically accessed the subject's colon to obtain tissue for histological analysis.

Another diagnosis-confirmatory assay can be a sigmoidoscopy. In sigmoidoscopy, a sigmoidoscope is used via the rectum to image portions of the colon and/or rectum. According to some reports, sigmoidoscopy is not widely used.

In some instances, a diagnosis-confirmatory assay is a stool-based assay. Typically, stool-based assays, when used in place of visual or structural inspection, are recommended to be utilized at a greater frequency than would be required if using visual or structural inspection. In some instances, a diagnosis-confirmatory assay is a guiac-based fecal occult blood test or a fecal immunochemical test (gFOBTs/FITs) (see, e.g., Navarro 2017 World J Gastroenterol. 23(20): 3632-3642, which is herein incorporated by reference with respect to colorectal cancer assays). FOBTs and FITs are sometimes used for diagnosis of colorectal cancer (see, e.g., Nakamura 2010 J Diabetes Investig. October 19; 1(5):208-11, which is herein incorporated by reference with respect to colorectal cancer assays). FIT is based on detection of occult blood in stool, the presence of which is often indicative of colorectal cancer but is often not in sufficient volume to permit identification by the unaided eye. For example, in a typical FIT, the test utilizes hemoglobin-specific reagent to test for occult blood in a stool sample. In various instances, FIT kits are suitable for use by individuals in their own homes. When used in the absence of other diagnosis-confirmatory assays, FIT may be recommended for use on an annual basis. FIT is generally not relied upon to provide sufficient diagnostic information for conclusive diagnosis of colorectal cancer.

Diagnosis-confirmatory assays also include gFOBT, which is designed to detect occult blood in stool by chemical reaction. Like FIT, when used in the absence of other diagnosis-confirmatory assays, gFOBT may be recommended for use on an annual basis. gFOBT is generally not relied upon to provide sufficient diagnostic information for conclusive diagnosis of colorectal cancer.

Diagnosis-confirmatory assays can also include stool DNA testing. Stool DNA testing for colorectal cancer can be designed to identify DNA sequences characteristic of cancer in stool samples. When used in the absence of other diagnosis-confirmatory assays, stool DNA testing may be recommended for use every three years. Stool DNA testing is generally not relied upon to provide sufficient diagnostic information for conclusive diagnosis of colorectal cancer.

One particular screening technology is a stool-based screening test (Cologuard® (Exact Sciences Corporation, Madison, Wis., United States), which combines an FIT assay with analysis of DNA for abnormal modifications, such as mutation and methylation. The Cologuard® test demonstrates improved sensitivity as compared to FIT assay alone, but can be clinically impracticable or ineffective due to low compliance rates, which low compliance rates are at least in part due to subject dislike of using stool-based assays (see, e.g., doi: 10.1056/NEJMc1405215 (e.g., 2014 N Engl J Med. 371(2):184-188)). The Cologuard® test appears to leave almost half of the eligible population out of the screening programs (see, e.g., van der Vlugt 2017 Br J Cancer. 116(1):44-49). Use of screening as provided herein, e.g., by a blood-based analysis, would increase the number of individuals electing to screen for colorectal cancer (see, e.g., Adler 2014 BMC Gastroenterol. 14:183; Liles 2017 Cancer Treatment and Research Communications 10: 27-31). To present knowledge, only one existing screening technology for colorectal cancer, Epiprocolon, is FDA-approved and CE-IVD marked and is blood-based. Epiprocolon is based on hypermethylation of SEPT9 gene. The Epiprocolon test suffers from low accuracy for colorectal cancer detection with sensitivity of 68% and advanced adenoma sensitivity of only 22% (see, e.g., Potter 2014 Clin Chem. 60(9):1183-91). There is need in the art for, among other things, a non-invasive colorectal cancer screen that will likely achieve high subject adherence with high and/or improved specificity and/or sensitivity.

In various embodiments, screening in accordance with methods and compositions of the present disclosure reduces colorectal cancer mortality, e.g., by early colorectal cancer diagnosis. Data supports that colorectal cancer screening reduces colorectal cancer mortality, which effect persisted for over 30 years (see, e.g., Shaukat 2013 N Engl J Med. 369(12):1106-14). Moreover, colorectal cancer is particularly difficult to treat at least in part because colorectal cancer, absent timely screening, may not be detected until cancer is past early stages. For at least this reason, treatment of colorectal cancer is often unsuccessful. To maximize population-wide improvement of colorectal cancer outcomes, utilization of screening in accordance with the present disclosure can be paired with, e.g., recruitment of eligible subjects to ensure widespread screening.

In various embodiments, screening of colorectal cancer including one or more methods and/or composition s disclosed herein is followed by treatment of colorectal cancer, e.g., treatment of early stage colorectal cancer. In various embodiments, treatment of colorectal cancer, e.g., early stage colorectal cancer, includes administration of a therapeutic regimen including one or more of surgery, radiation therapy, and chemotherapy. In various embodiments, treatment of colorectal cancer, e.g., early stage colorectal cancer, includes administration of a therapeutic regimen including one or more of treatments provided herein for treatment of stage 0 colorectal cancer, stage I colorectal cancer, and/or stage II colorectal cancer.

In various embodiments, treatment of colorectal cancer includes treatment of early stage colorectal cancer, e.g., stage 0 colorectal cancer or stage I colorectal cancer, by one or more of surgical removal of cancerous tissue e.g., by local excision (e.g., by colonoscope), partial colectomy, or complete colectomy.

In various embodiments, treatment of colorectal cancer includes treatment of early stage colorectal cancer, e.g., stage II colorectal cancer, by one or more of surgical removal of cancerous tissue (e.g., by local excision (e.g., by colonoscope), partial colectomy, or complete colectomy), surgery to remove lymph nodes near to identified colorectal cancer tissue, and chemotherapy (e.g., administration of one or more of 5-FU and leucovorin, oxaliplatin, or capecitabine).

In various embodiments, treatment of colorectal cancer includes treatment of stage III colorectal cancer, by one or more of surgical removal of cancerous tissue (e.g., by local excision (e.g., by colonoscopy-based excision), partial colectomy, or complete colectomy), surgical removal of lymph nodes near to identified colorectal cancer tissue, chemotherapy (e.g., administration of one or more of 5-FU, leucovorin, oxaliplatin, capecitabine, e.g., in a combination of (i) 5-FU and leucovorin, (ii) 5-FU, leucovorin, and oxaliplatin (e.g., FOLFOX), or (iii) capecitabine and oxaliplatin (e.g., CAPEOX)), and radiation therapy.

In various embodiments, treatment of colorectal cancer includes treatment of stage IV colorectal cancer, by one or more of surgical removal of cancerous tissue (e.g., by local excision (e.g., by colonoscope), partial colectomy, or complete colectomy), surgical removal of lymph nodes near to identified colorectal cancer tissue, surgical removal of metastases, chemotherapy (e.g., administration of one or more of 5-FU, leucovorin, oxaliplatin, capecitabine, irinotecan, VEGF-targeted therapeutic agent (e.g., bevacizumab, ziv-aflibercept, or ramucirumab), EGFR-targeted therapeutic agent (e.g., cetuximab or panitumumab), Regorafenib, trifluridine, and tipiracil, e.g., in a combination of or including (i) 5-FU and leucovorin, (ii) 5-FU, leucovorin, and oxaliplatin (e.g., FOLFOX), (iii) capecitabine and oxaliplatin (e.g., CAPEOX), (iv) leucovorin, 5-FU, oxaliplatin, and irinotecan (FOLFOXIRI), and (v) trifluridine and tipiracil (Lonsurf)), radiation therapy, hepatic artery infusion (e.g., if cancer has metastasized to liver), ablation of tumors, embolization of tumors, colon stent, colorectomy, colostomy (e.g., diverting colostomy), and immunotherapy (e.g., pembrolizumab).

Those of skill in the art that treatments of colorectal cancer provided herein can be utilized, e.g., as determined by a medical practitioner, alone or in any combination, in any order, regimen, and/or therapeutic program. Those of skill in the art will further appreciate that advanced treatment options may be appropriate for earlier stage cancers in subjects previously having suffered a cancer or colorectal cancer, e.g., subjects diagnosed as having a recurrent colorectal cancer.

In some embodiments, methods and compositions for colorectal cancer screening provided herein can inform treatment and/or payment (e.g., reimbursement for or reduction of cost of medical care, such as screening or treatment) decisions and/or actions, e.g., by individuals, healthcare facilities, healthcare practitioners, health insurance providers, governmental bodies, or other parties interested in healthcare cost.

In some embodiments, methods and compositions for colorectal cancer screening provided herein can inform decision making relating to whether health insurance providers reimburse a healthcare cost payer or recipient (or not), e.g., for (1) screening itself (e.g., reimbursement for screening otherwise unavailable, available only for periodic/regular screening, or available only for temporally- and/or incidentally-motivated screening); and/or for (2) treatment, including initiating, maintaining, and/or altering therapy, e.g., based on screening results. For example, in some embodiments, methods and compositions for colorectal cancer screening provided herein are used as the basis for, to contribute to, or support a determination as to whether a reimbursement or cost reduction will be provided to a healthcare cost payer or recipient. In some instances, a party seeking reimbursement or cost reduction can provide results of a screen conducted in accordance with the present specification together with a request for such reimbursement or cost reduction of a healthcare cost. In some instances, a party making a determination as to whether or not to provide a reimbursement or cost reduction of a healthcare cost will reach a determination based in whole or in part upon receipt and/or review of results of a screen conducted in accordance with the present specification.

For the avoidance of any doubt, those of skill in the art will appreciate from the present disclosure that methods and compositions for colorectal cancer diagnosis of the present specification are at least for in vitro use. Accordingly, all aspects and embodiments of the present disclosure can be performed and/or used at least in vitro.

Kits

The present disclosure includes, among other things, kits including one or more compositions for use in colorectal cancer screening as provided herein, optionally in combination with instructions for use thereof in colorectal cancer screening. In various embodiments, a kit for screening of colorectal cancer can include one or more of: one or more oligonucleotide primers (e.g., one or more oligonucleotide primer pairs, e.g., as found in Table 13), one or more MSREs, one or more reagents for qPCR (e.g., reagents sufficient for a complete qPCR reaction mixture, including without limitation dNTP and polymerase), and instructions for use of one or more components of the kit for colorectal cancer screening. In various embodiments, a kit for screening of colorectal cancer can include one or more of: one or more oligonucleotide primers (e.g., one or more oligonucleotide primer pairs, e.g., as found in Table 13), one or more bisulfite reagents, one or more reagents for qPCR (e.g., reagents sufficient for a complete qPCR reaction mixture, including without limitation dNTP and polymerase), and instructions for use of one or more components of the kit for colorectal cancer screening.

In certain embodiments, a kit of the present disclosure includes at least one oligonucleotide primer pair for amplification of a methylation locus and/or DMR as disclosed herein.

In some instances, a kit of the present disclosure includes one or more oligonucleotide primer pairs for amplification of one or more methylation loci of the present disclosure. In some instances, kit of the present disclosure includes one or more oligonucleotide primer pairs for amplification of one or more methylation loci that are or include all or a portion of one or more genes provided in Table 1. In some particular instances, a kit of the present disclosure includes oligonucleotide primer pairs for a plurality of methylation loci that each are or include all or a portion of a gene identified in Table 1, the plurality of methylation loci including, e.g., 3, 4, 5, 6, 7, 8, 9, 10, 11, 12, 13, 14, 15, or 16 methylation loci, e.g., as provided in any of Tables 1 to 6.

In some instances, a kit of the present disclosure includes one or more oligonucleotide primer pairs for amplification of one or more DMRs of the present disclosure. In some instances, kit of the present disclosure includes one or more oligonucleotide primer pairs for amplification of one or more DMRs that are, include all or a portion of, or are within a gene identified in Table 1. In some particular embodiments, a kit of the present disclosure includes oligonucleotide primer pairs for a plurality of DMRs each of which is, includes all or a portion of, or is within a gene identified in Table 1, e.g., 2, 3, 4, 5, 6, 7, 8, 9, 10, 11, 12, 13, 14, 15, or 16 DMRs, e.g., in accordance with any one of Tables 1 to 6.

In some instances, kit of the present disclosure includes one or more oligonucleotide primer pairs for amplification of one or more DMRs of Table 7. In some particular instances, a kit of the present disclosure includes oligonucleotide primer pairs for a plurality of DMRs of Table 7, the plurality of DMRs including, e.g., 2, 3, 4, 5, 6, 7, 8, 9, 10, 11, 12, 13, 14, 15, 16, 17, 18, 19, 20, 21, 22, 23, 24, 25, 26, 27, or 28 DMRs of Table 7, e.g., as provided in any of Tables 8 to 12.

In various embodiments, a kit of the present disclosure includes one or more oligonucleotide primer pairs provided in Table 13. Those of skill in the art will appreciate that oligonucleotide primer pairs provided in Table 13 can be provided in any combination of one or more oligonucleotide primer pairs, e.g., in a combination as provided in any one of Tables 1-12.

In various particular embodiments, kit of the present disclosure does not include oligonucleotide primer pairs that amplify all or a portion of one or more of FGF14, ZNF471, PDGFD, and ALK.

A kit of the present disclosure can further include one or more MSREs individually or in a single solution. In various embodiments, one or more MSREs are selected from the set of MSREs including AciI, Hin6I, HpyCH4IV, and HpaII (e.g., such that the kit includes AciI, Hin6I, and HpyCH4IV, either individually or in a single solution). In certain embodiments, a kit of the present disclosure includes one or more reagents for qPCR (e.g., reagents sufficient for a complete qPCR reaction mixture, including without limitation dNTP and polymerase).

EXAMPLES

The present Examples confirm that the present disclosure provides methods and compositions for, among other things, screening for and treatment of colorectal cancer. The present Examples further demonstrate that compositions and methods provided herein provide a remarkably high degree of sensitivity and specificity in screening and/or treatment of colorectal cancer. Also provided are clinical studies comparing methylation of biomarkers in samples from subjects diagnosed as having colorectal cancer and methylation of biomarkers in samples from control subjects, further demonstrating screening for colorectal cancer including methods and/or compositions of the present disclosure. Except as specifically stated otherwise, samples of the present Examples are humans or of human origin. With the exception of Example 1, all experiments were performed using plasma samples.

Example 1. Identification of Methylation Biomarkers Associated with Colorectal Cancer The present Example includes identification of CpG loci that are hypermethylated in one or more of colon cancer and rectal cancer as compared to healthy controls. In particular, experiments of the present Example examined CpG methylation in samples from (i) colon cancers of 341 subjects previously diagnosed as suffering from colon cancer, which subjects had not been previously treated by chemotherapy or radiotherapy; (ii) rectal cancers of 118 subjects previously diagnosed as suffering from rectal cancer, which subjects had not been previously treated by chemotherapy or radiotherapy; (iii) colons of 40 healthy control subjects not diagnosed as suffering from colorectal cancer; and (iv)

leukocytes of 10 healthy control subjects not diagnosed as suffering from a colorectal cancer. Tissue samples were of fresh frozen tissue.

Samples were analyzed for DNA methylation by a global methylomics analysis platform (Infinium HumanMethylation450 (HM450) beadarray). The Infinium HumanMethylation450 array assesses methylation status of >450 000 CpGs located throughout the genome. DNA methylation profiles were obtained from all the tissue samples.

CpG methylation sites for which methylation status did not substantially differ between a colorectal cancer and healthy controls were identified and removed from consideration (mean b-value <0.25 and b-value >0.3 in no more than five samples across the entire set). This filtering produced a list of CpG methylation sites for which methylation status substantially differed between a colorectal cancer and healthy controls. The resulting set of CpG methylation sites was then further filtered by excluding CpG methylation sites with a mean b-value difference equal to or less than 0.1, yielding 253 CpG methylation sites. Each of the 253 CpG methylation sites was associated with a hypermethylated status in colorectal cancer status as compared to controls.

Thus, the present Example generated a set of 253 individual CpG methylation sites that are methylation biomarkers for colorectal cancer. The 253 methylation biomarkers represent a plurality of DMRs together found within 36 genes, i.e., within 36 methylation loci. Each of the 36 DMRs is hypermethylated in colorectal cancer as compared to healthy controls.

Example 2: Development of Cell-Free DNA Assay for Methylation Biomarkers by MSRE-qPCR The present Example develops an assay for determining the methylation status of colorectal cancer methylation biomarkers based on circulating cell free DNA (cfDNA. cfDNA is incomplete and fragmented, and the mechanism by which the cfDNA is transmitted from cancer cells to blood (as a portion called circulating tumor DNA) is unknown. At least because the 253 methylation biomarkers of Example 1 were identified from tissue samples, it was not known prior to the experiments of the present Example whether identified colorectal cancer methylation biomarkers could be sufficiently analyzed from cfDNA to successfully capture the ctDNA portion that allows for identifying subjects or samples for colorectal cancer.

As a critical step toward determining whether colorectal cancer methylation biomarkers identified in Example 1 could be sufficiently analyzed from cfDNA to successfully capture the ctDNA portion that allows for identification of subjects or samples for colorectal cancer, a sensitive assay was developed for screening of these biomarkers. In particular, a Methylation-Sensitive Restriction Enzyme (MSRE)-qPCR methodology was developed. The MSRE-qPCR methodology was developed to measure methylation of DMRs covering identified CpG sites in blood samples, in particular in cell-free DNA (cfDNA) of tumors present in blood.

Development of the MSRE-qPCR methodology was significant at least in part because analyzing CpG methylation biomarkers derived from tumor tissue by analysis of cfDNA is challenging due to the low concentration of tumor-derived DNA circulating in blood (0.1-1%) as compared to the non-tumor DNA background of the sample. Thus, while it is generally preferred to develop biomarker analyses that rely on readily obtainable samples such as blood, urine, or stool, use of blood for analysis of tumor derived methylation biomarkers is challenging. Thus, even after identification of methylation biomarkers characteristic of colorectal cancer in tissue, as discussed above, it cannot be predicted whether the fragmented and poorly understood nature of ctDNA will permit successful screening using methylation biomarkers identified in tissue.

MSRE-qPCR requires design of oligonucleotide primers (MSRE-qPCR oligonucleotide primer pairs) that amplify loci that each include at least one colorectal cancer MSRE cleavage site (i.e., an MSRE cleavage site that covers at least one colorectal cancer methylation biomarker site, such that cleavage of the MSRE cleavage site is permitted in nucleic acid molecules where all of the at least one colorectal cancer methylation biomarker sites are unmethylated and blocked in nucleic acid molecules where at least one of the at least one colorectal cancer methylation biomarker sites is methylated). MSRE-qPCR assays can utilize multiple restriction enzymes to enhance the range of colorectal cancer methylation biomarker sites that can be assayed by a single MSRE-qPCR reaction, as a single MSRE is unlikely to cleavage sites that together include all methylation biomarker sites of interest. MSRE-qPCR assays of the present Examples utilize the MSREs AciI, Hin6I, and HpyCH4IV, which together were found to provide sufficient coverage.

Figure 1:
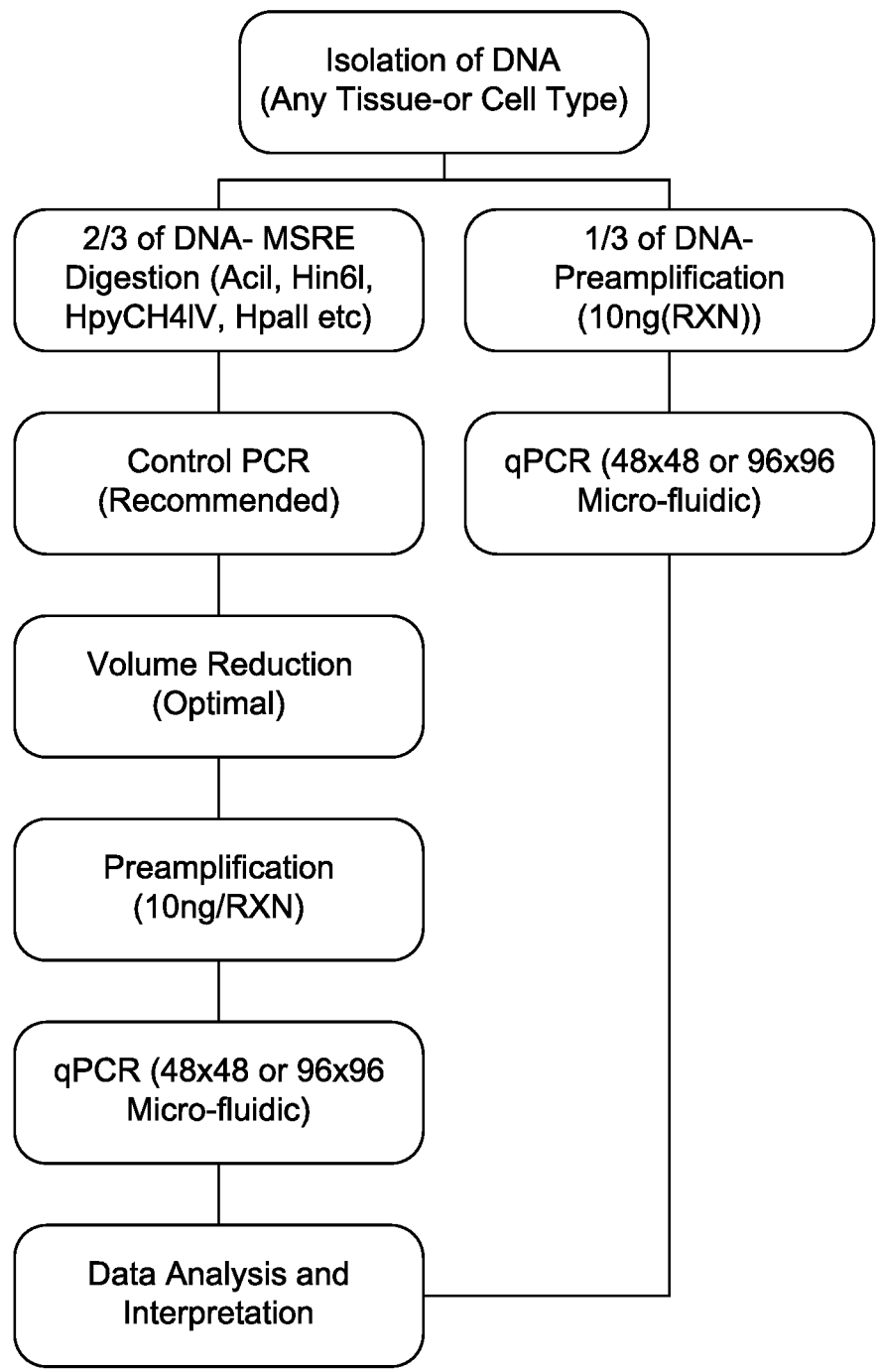
FIG. 1 is a schematic showing an example MSRE-qPCR approach.

An exemplary schematic work flow for MSRE-qPCR is provided in FIG. 1. As performed in the present Examples, circulating cell-free tumor DNA was extracted from subject blood (typically a plasma sample of approximately 4 mL) by QIAamp MinElute ccfDNA Kit in accordance with manufacturer protocol (QIAamp MinElute ccfDNA Handbook August 2018, Qiagene). As shown in FIG. 1, isolated cfDNA was divided into two aliquots, a first of which aliquots is utilized in a qPCR quality control analysis, and a second of which aliquots is used in MSRE-qPCR For MSRE-qPCR, ⅔ of eluted cfDNA by volume was digested with MSREs. Because non-methylated DNA is selectively cleaved, contacting the cfDNA with the MSREs enriches the sample for methylation-derived signal; methylated DNA remains intact and quantifiable. The remaining ⅓ of eluted cfDNA by volume was used for qPCR using the MSRE-qPCR oligonucleotide primers to confirm that amplicons were successfully amplified from cfDNA, which amplification confirms that template is present, hence providing technical quality control.

As applied herein, MSRE-qPCR oligonucleotide primer pairs were successfully developed for amplification of DMRs together including 180 of the 253 CpG methylation biomarker sites identified in Example 1. DMRs typically included 1 to 15 MSRE cleavage sites, which MSRE cleavage sites together covered each of the 180 methylation biomarker sites. As applied herein, methylation status of six genes (JUB, H19, TBP, TCEB2, SNRPN, IRF4) provided a methylation control, which control permitted monitoring of assay robustness and reproducibility.

Figure 4:
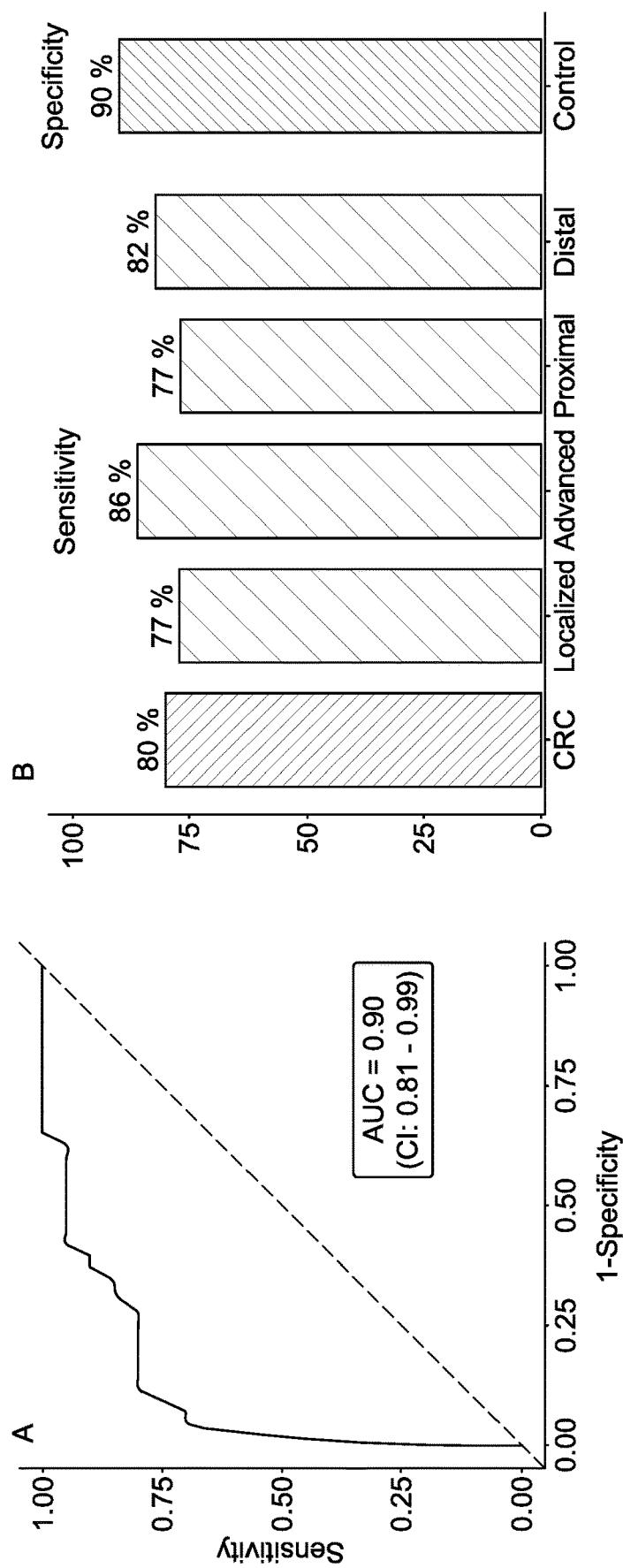
FIG. 4 includes panels A and B. Panel A of FIG. 4 is a graph showing performance of colorectal cancer screening using a representative proof-of-principle panel of DMRs on the second subject group. ROC curve and AUC for all subjects of the second subject group are shown. Panel B of FIG. 4 is a chart showing accuracy values, including, from left to right, overall sensitivity of colorectal screening for colorectal cancer, sensitivity of colorectal screening for localized colorectal cancer, sensitivity of colorectal screening for advanced colorectal cancer, sensitivity of colorectal screening for proximal colorectal cancer, sensitivity of colorectal screening for distal colorectal cancer, and specificity of colorectal screening for control subjects (healthy subjects and subjects with non-advanced adenoma).
Figure 5:
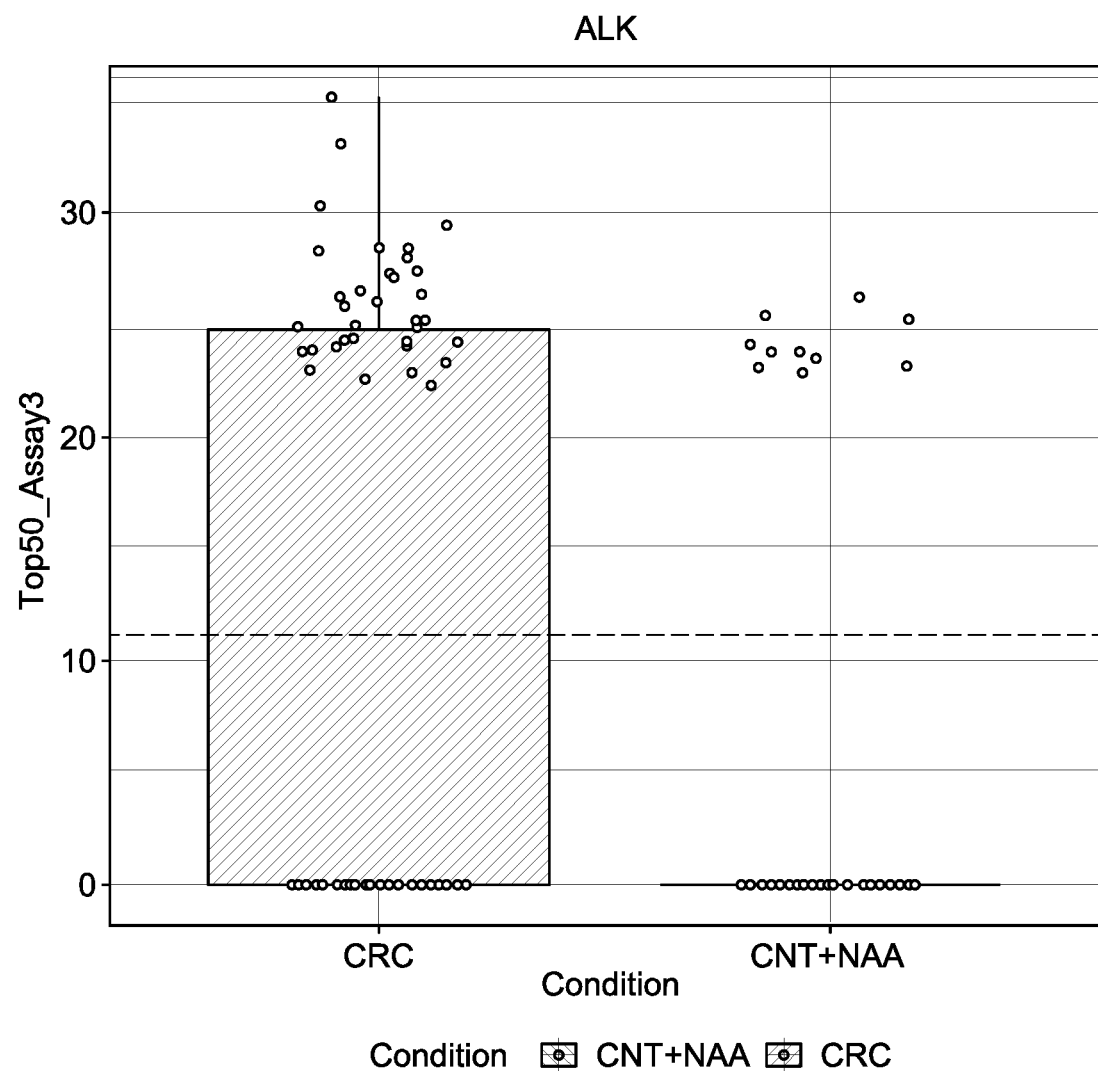
FIG. 5 is a graph representing Ct values from MSRE-qPCR of ALK '434 for subjects with colorectal cancer and control subjects (healthy subjects and subjects with non-advanced adenoma). Data represent the second subject group (63 subjects) used for testing. For display purposes, Ct values are subtracted from 45 (45−Ct). Higher 45−Ct values correspond to higher methylation status, demonstrating hypermethylation in subjects with colorectal cancer.
Figure 6:
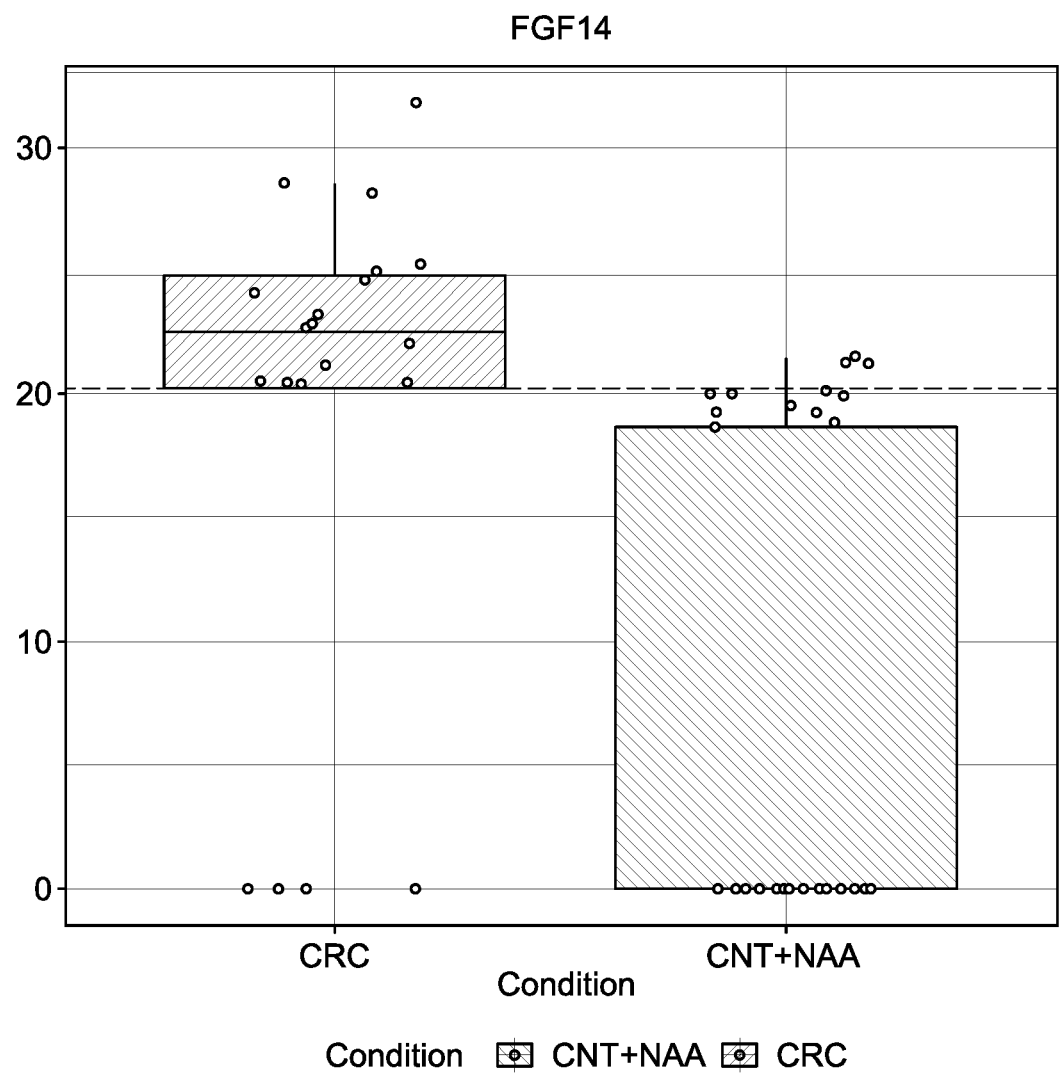
FIG. 6 is a graph representing Ct values from MSRE-qPCR of FGF14 '577 DMR for subjects with colorectal cancer and control subjects (healthy subjects and subjects with non-advanced adenoma). Data represent the second subject group (63 subjects) used for testing. For display purposes, Ct values are subtracted from 45 (45−Ct). Higher 45−Ct values correspond to higher methylation status, demonstrating hypermethylation in subjects with colorectal cancer.
Figure 7:
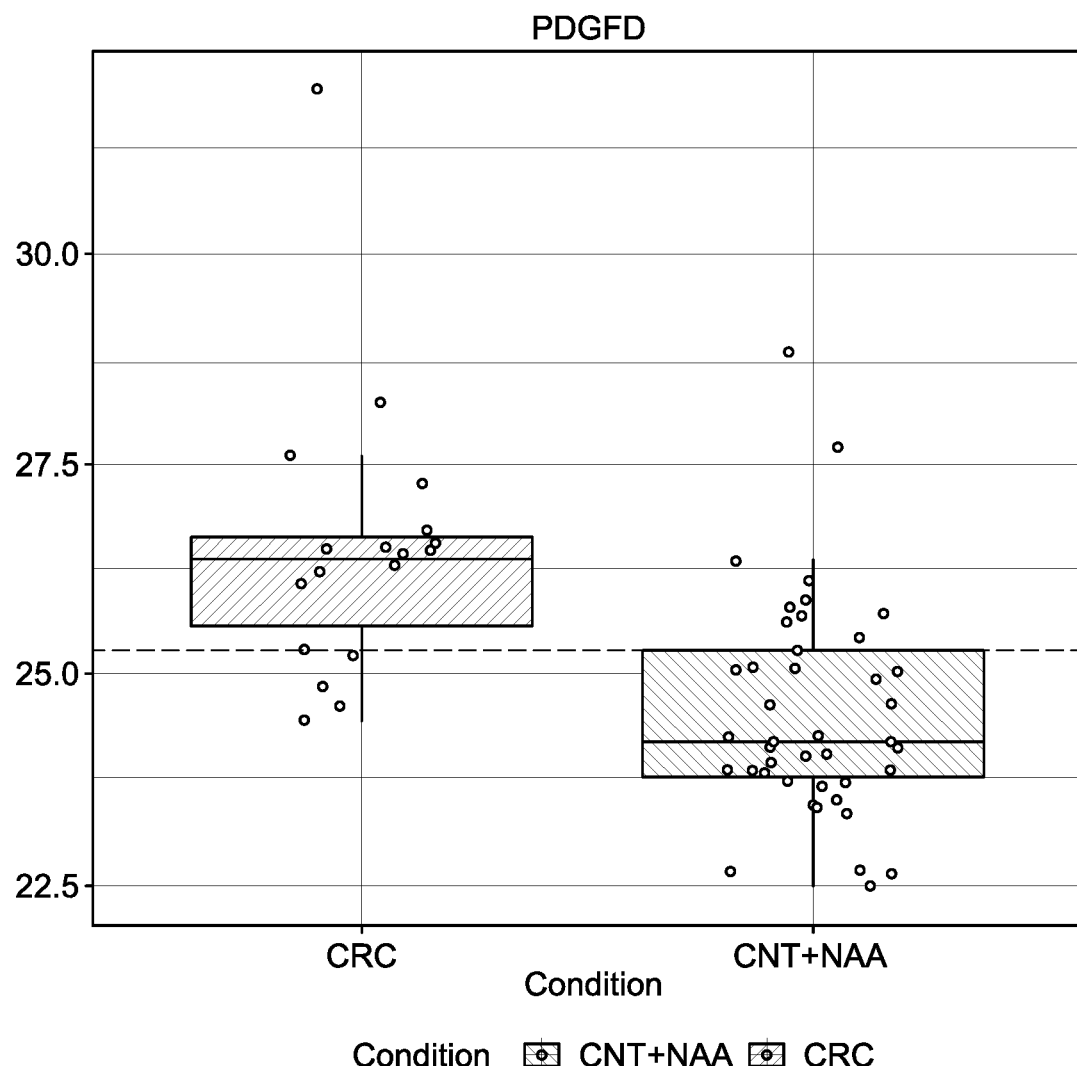
FIG. 7 is a graph representing Ct values from MSRE-qPCR of PDGFD '388 for subjects with colorectal cancer and control subjects (healthy subjects and subjects with non-advanced adenoma). Data represent the second subject group (63 subjects) used for testing. For display purposes, Ct values are subtracted from 45 (45−Ct). Higher 45−Ct values correspond to higher methylation status, demonstrating hypermethylation in subjects with colorectal cancer.
Figure 8:
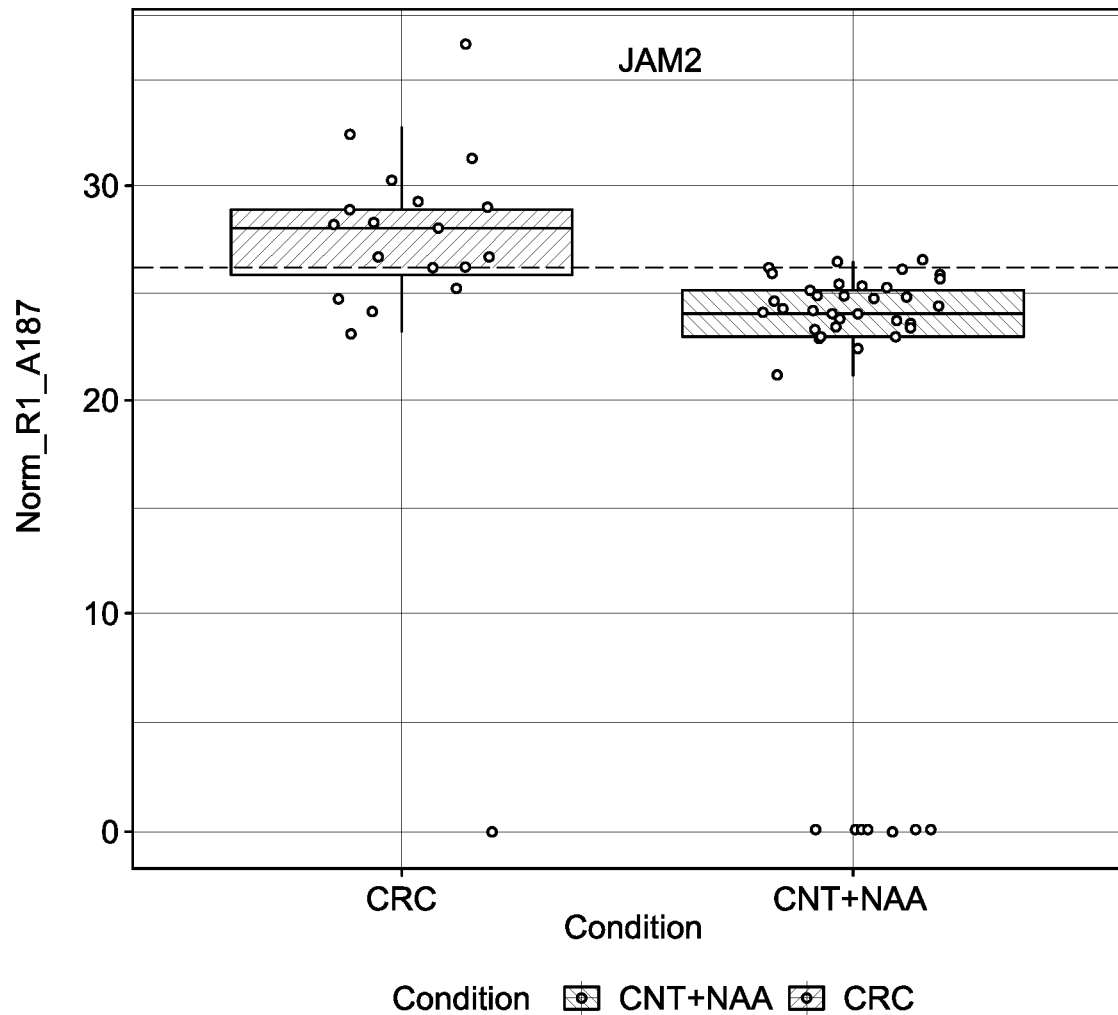
FIG. 8 is a graph representing Ct values from MSRE-qPCR of JAM2 '320 for subjects with colorectal cancer and control subjects (healthy subjects and subjects with non-advanced adenoma). Data represent the d second subject group (63 subjects) used for testing. For display purposes, Ct values are subtracted from 45 (45−Ct). Higher 45−Ct values correspond to higher methylation status, demonstrating hypermethylation in subjects with colorectal cancer.
Figure 9:
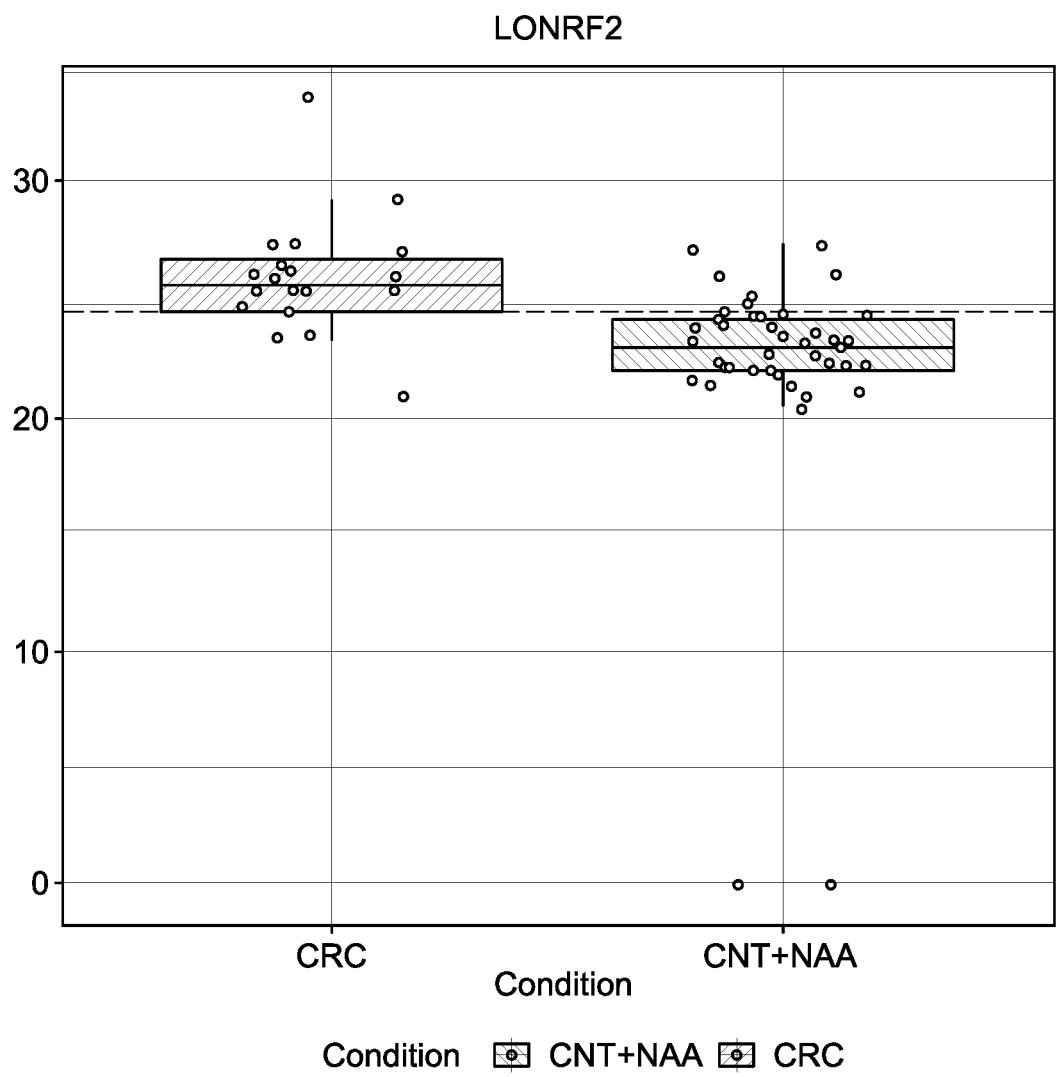
FIG. 9 is a graph representing Ct values from MSRE-qPCR of LONRF2 '281 for subjects with colorectal cancer and control subjects (healthy subjects and subjects with non-advanced adenoma). Data represent the second subject group (63 subjects) used for testing. For display purposes, Ct values are subtracted from 45 (45−Ct). Higher 45−Ct values correspond to higher methylation status, demonstrating hypermethylation in subjects with colorectal cancer.

Example 3: MSRE-qPCR of cfDNA Successfully Distinguishes Subjects by Colorectal Cancer Status To probe clinical diagnostic and prognostic power of identified methylation biomarkers, the DMRs amplified by the MSRE-qPCR oligonucleotide primer pairs covering the 180 methylation biomarker sites, and appropriate controls, were assayed in cfDNA extracted from plasma of human subjects. Subjects were undiagnosed individuals seeking, or in the process of obtaining, a diagnosis regarding possible colorectal cancer, such that methylation biomarker analysis could be performed prior to traditional diagnostic testing for colorectal cancer and then compared to a subsequent traditional diagnosis. In particular, cfDNA was sampled from undiagnosed individuals seeking, or in the process of obtaining, a diagnosis regarding possible colorectal cancer at screening centers and oncology clinics in Spain and the United States between 2017 and 2018. A first subject group included 70 such individuals (see description of the first subject group in FIG. 2), and a second subject group included 63 such individuals (see description of second subject group in FIG. 3). Initial results based on MSRE-qPCR analysis of a small panel of tested DMRs of genes shown in Table 14 in the second subject group provided proof-of-principle for colorectal cancer diagnosis: results demonstrated overall diagnostic sensitivity of 80%, for colorectal cancer, with diagnostic sensitivity of up to 75% for early localized colorectal cancer, and 90% specificity (FIG. 4). The representative proof-of-principle panel of DMRs performed similarly, and/or statistically equally, well with respect to proximal cancers and distal cancers (FIG. 4). The proof-of-principle panel of DMRs also performed similarly, and/or statistically equally, well with respect to localized cancer and advanced cancer (FIG. 4). Moreover, MSRE-qPCR analysis of methylation of MSRE-qPCR control genes and of undigested DNA controls showed high technical reliability of the developed MSRE-qPCR assays in measuring colorectal cancer biomarker methylation status in plasma cfDNA.

FIGS. 5-9 show the association of methylation status of colorectal cancer DMRs with colorectal cancer. Results are displayed as the MSRE-qPCR Ct value subtracted from 45 (i.e., 45−Ct value) for display purposes. Results demonstrate the surprisingly high predictive power of individual colorectal cancer methylation biomarkers, or of as few as three individual colorectal cancer methylation biomarkers, of the present disclosure for colorectal cancer, e.g., for use in determining screening for colorectal cancer in a subject.

were used for building a support-vector machine (SVM) algorithm-based classification model. This analysis identified several subsets of markers (2,3,5,8,15,28 as described in Tables 7-12) that in SVM-model gave a good prediction.

All models (2, 3, 5, 8, 15 and 28 colorectal cancer DMR panels) were applied to cfDNA extracted from plasma of a third subject group. The third subject group included 82 subjects who had either previously received a confirmed diagnosis of colorectal cancer or were control subjects known to not have colorectal cancer deemed (the control group including subjects having hyperplastic polyps and/or non-advanced adenoma, but not colorectal cancer), based on colonoscopy screening. The 82 subjects were subjects attending colorectal cancer screening and oncology units in Spain and the United States. Further description of the third subject group is shown in FIG. 10.

Oligonucleotide primer pairs (Table 13) for amplification of the 28 DRMs in MSRE-qPCR cover at least one MSRE cleavage site, typically 3 to 15 MSRE cleavage sites. MSRE-qPCR was carried out according to the methodology described in Example 2.

Figure 11:
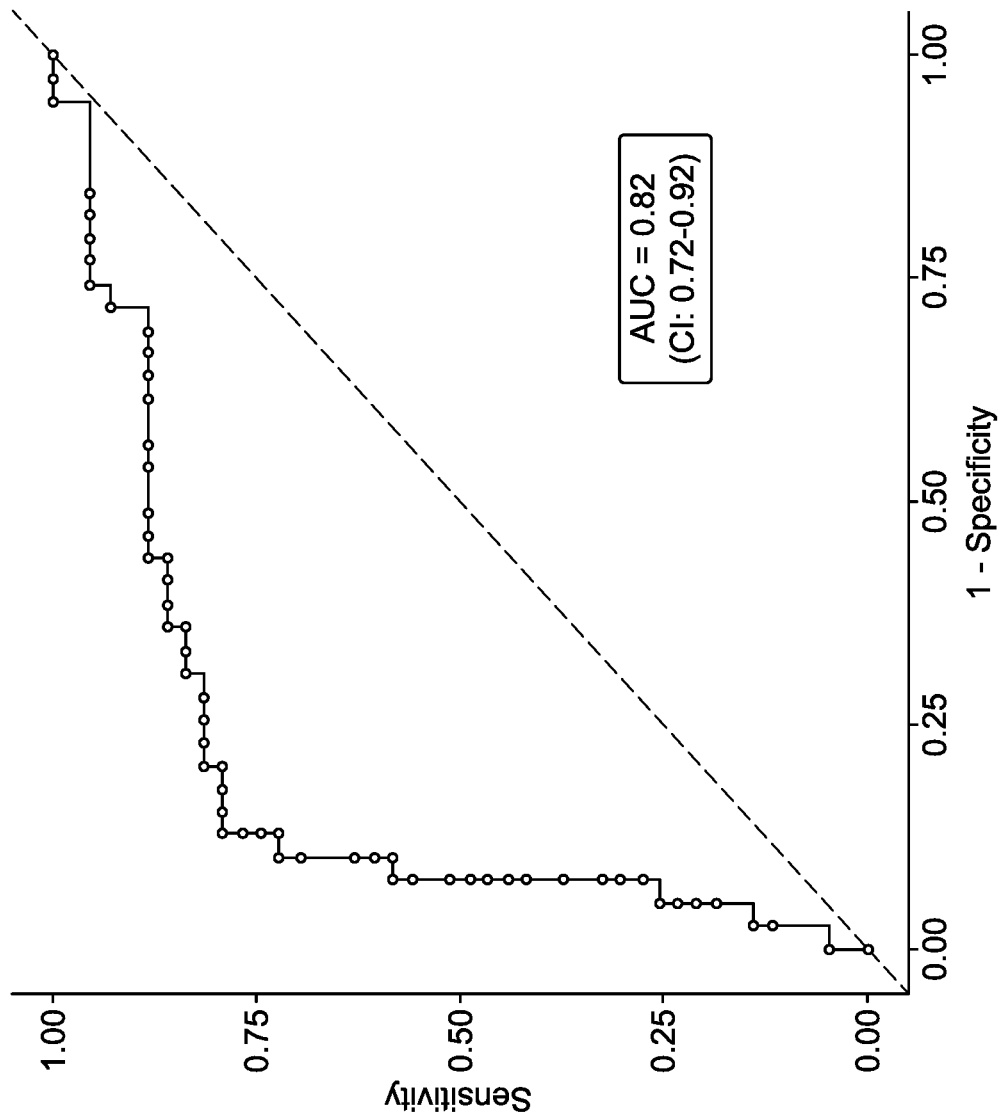
FIG. 11 is a graph showing performance of colorectal cancer screening using a 28 DMR panel in the third subject group. ROC curve and AUC for all subjects of the third subject group are shown. ROC-curve analysis showed that a 28 DMR panel achieved general colorectal cancer sensitivity of 79%, with 75% sensitivity for localized (early) cancer and 84% sensitivity for advanced cancer, on a very stable specificity of 87% at AUC 82% (see also Table 15).
Figure 12:
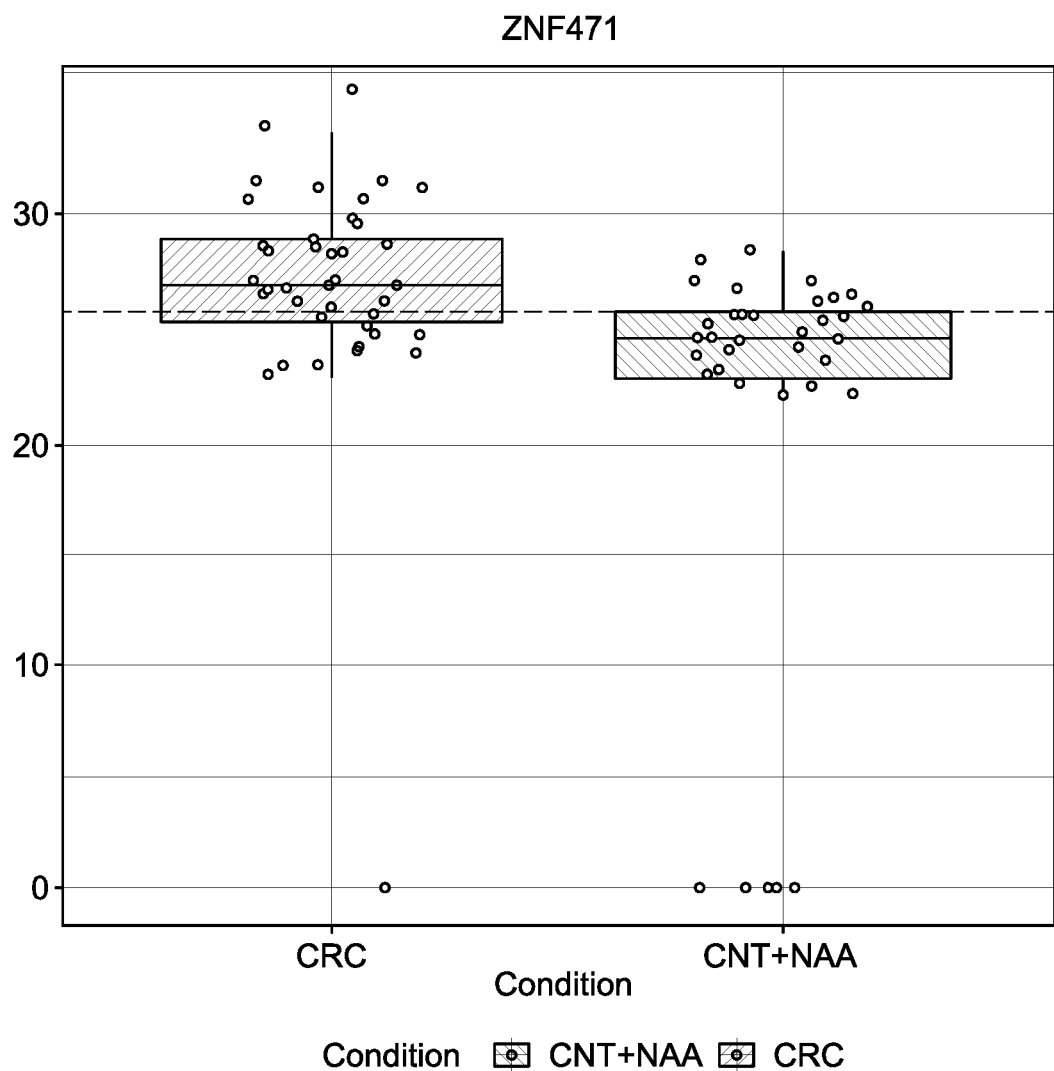
FIG. 12 is a graph representing Ct values from MSRE-qPCR of ZNF471 '527 for subjects with colorectal cancer and control subjects (healthy subjects and subjects with non-advanced adenoma). Data represent the third subject group (82 subjects). For display purposes, Ct values are subtracted from 45 (45−Ct). Higher 45−Ct values correspond to higher methylation status, demonstrating hypermethylation in subjects with colorectal cancer.
Figure 13:
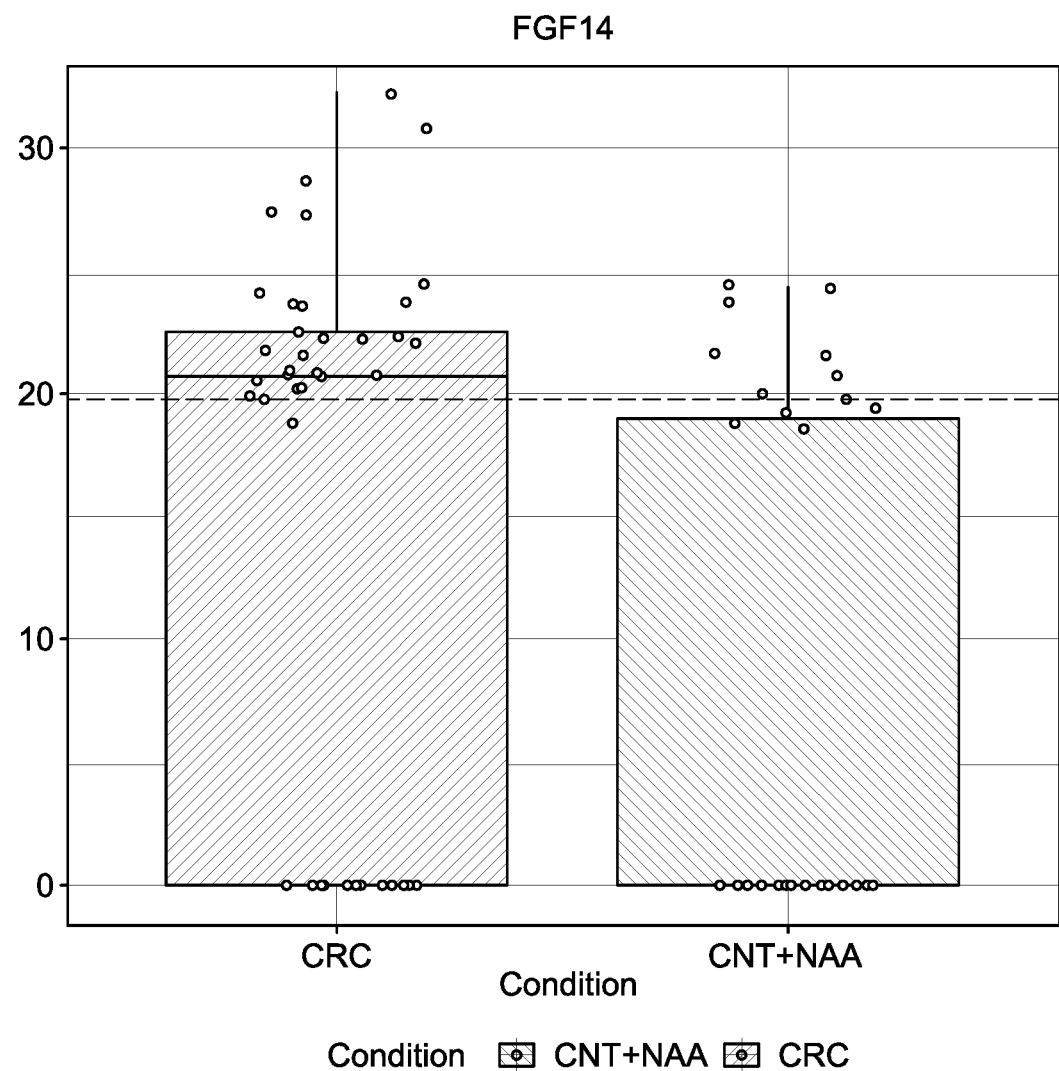
FIG. 13 is a graph representing Ct values from MSRE-qPCR of FGF14 '577 for subjects with colorectal cancer and control subjects (healthy subjects and subjects with non-advanced adenoma). Data represent the third subject group (82 subjects). For display purposes, Ct values are subtracted from 45 (45−Ct). Higher 45−Ct values correspond to higher methylation status, demonstrating hypermethylation in subjects with colorectal cancer.
Figure 14:
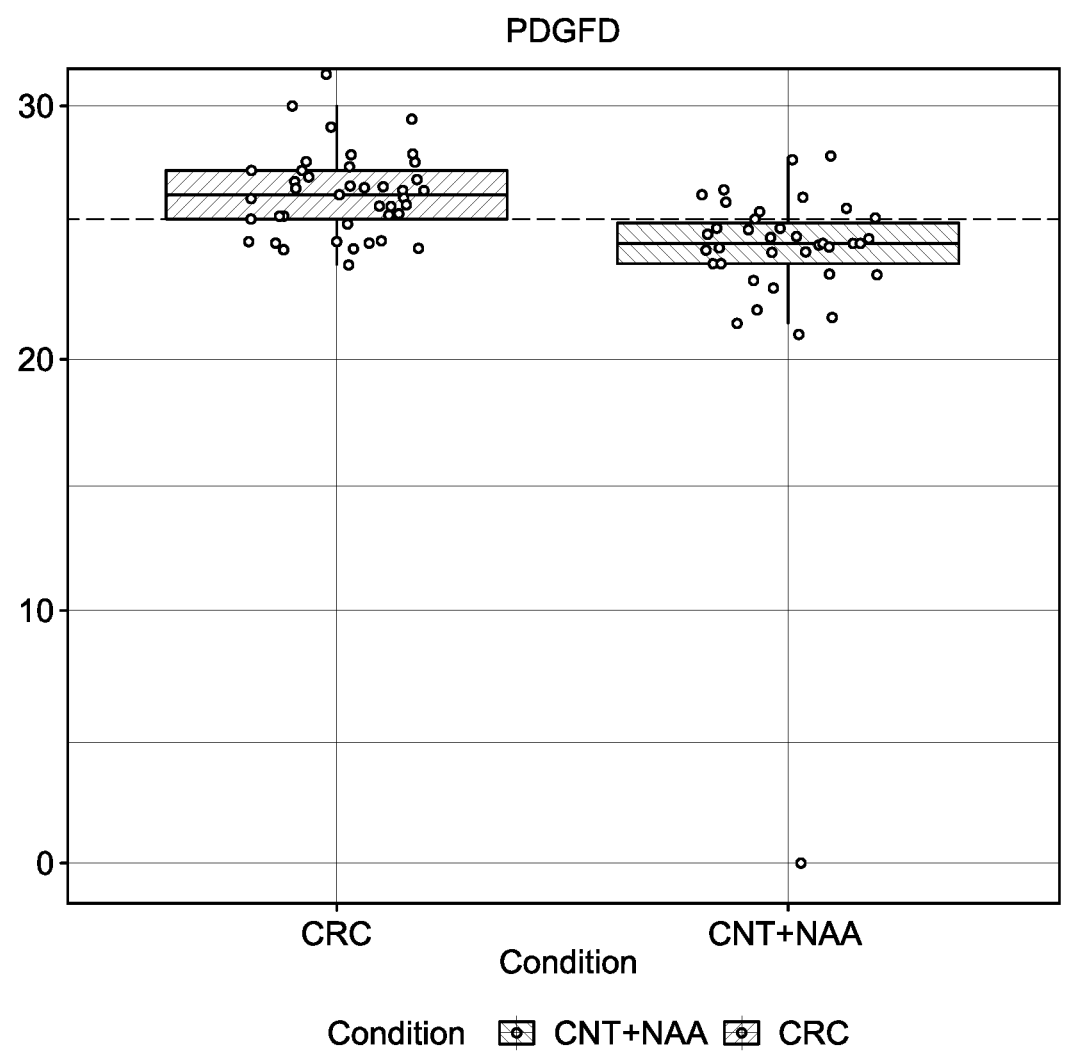
FIG. 14 is a graph representing Ct values from MSRE-qPCR of PDGFD '388 for subjects with colorectal cancer and control subjects (healthy subjects and subjects with non-advanced adenoma). Data represent the third subject group (82 subjects). For display purposes, Ct values are subtracted from 45 (45−Ct). Higher 45−Ct values correspond to higher methylation status, demonstrating hypermethylation in subjects with colorectal cancer.
Figure 15:
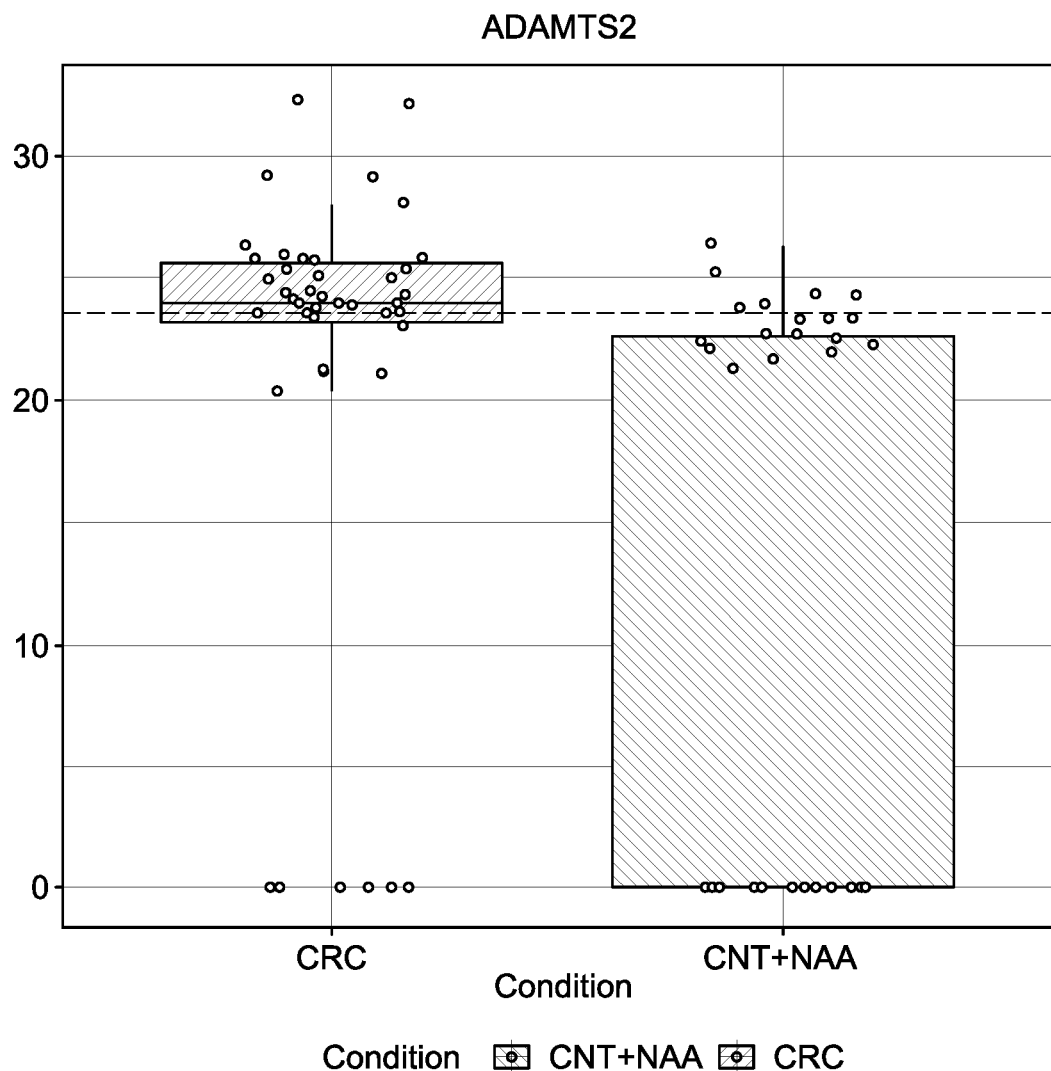
FIG. 15 is a graph representing Ct values from MSRE-qPCR of ADAMTS2 '254 for subjects with colorectal cancer and control subjects (healthy subjects and subjects with non-advanced adenoma). Data represent the third subject group (82 subjects). For display purposes, Ct values are subtracted from 45 (45−Ct). Higher 45−Ct values correspond to higher methylation status, demonstrating hypermethylation in subjects with colorectal cancer.
Figure 16:
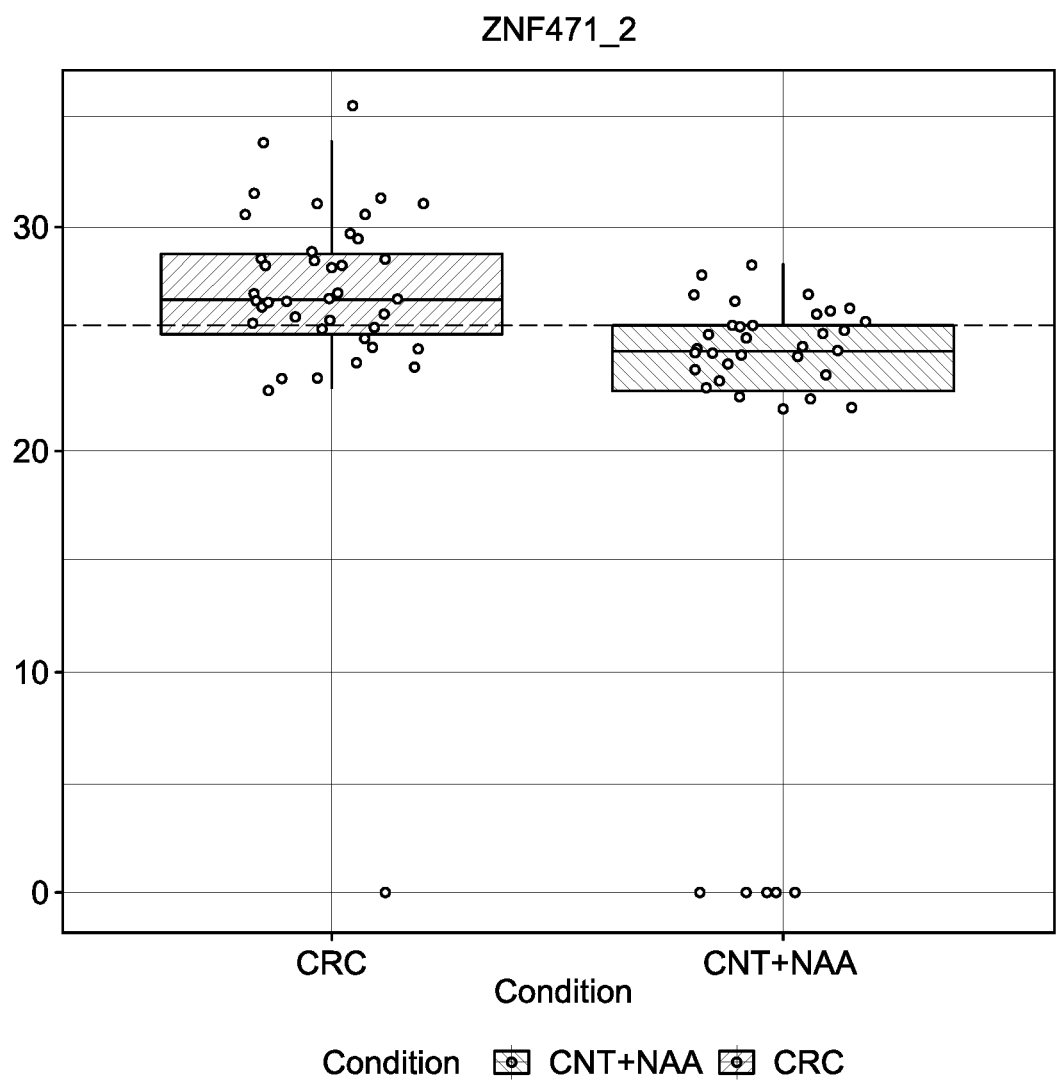
FIG. 16 is a graph representing Ct values from MSRE-qPCR of ZNF471 '558 (which DMR is alternatively referred to herein as ZNF471_2) for subjects with colorectal cancer and control subjects (healthy subjects and subjects with non-advanced adenoma). Data represent the third subject group (82 subjects). For display purposes, Ct values are subtracted from 45 (45−Ct). Higher 45−Ct values correspond to higher methylation status, demonstrating hypermethylation in subjects with colorectal cancer.
Figure 17:
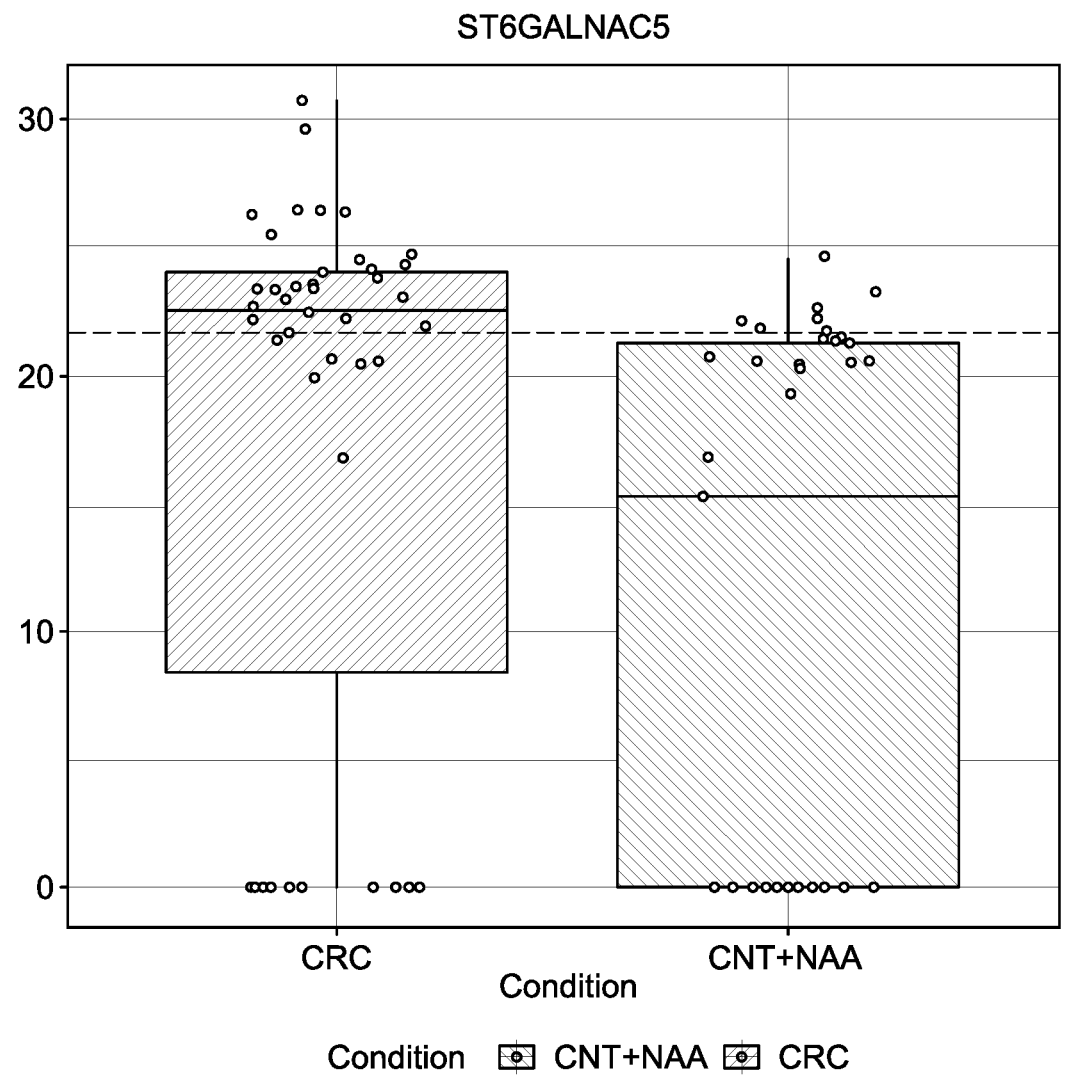
FIG. 17 is a graph representing Ct values from MSRE-qPCR of ST6GALNAC5 '456 for subjects with colorectal cancer and control subjects (healthy subjects and subjects with non-advanced adenoma). Data represent the third subject group (82 subjects). For display purposes, Ct values are subtracted from 45 (45−Ct). Higher 45−Ct values correspond to higher methylation status, demonstrating hypermethylation in subjects with colorectal cancer.
Figure 18:
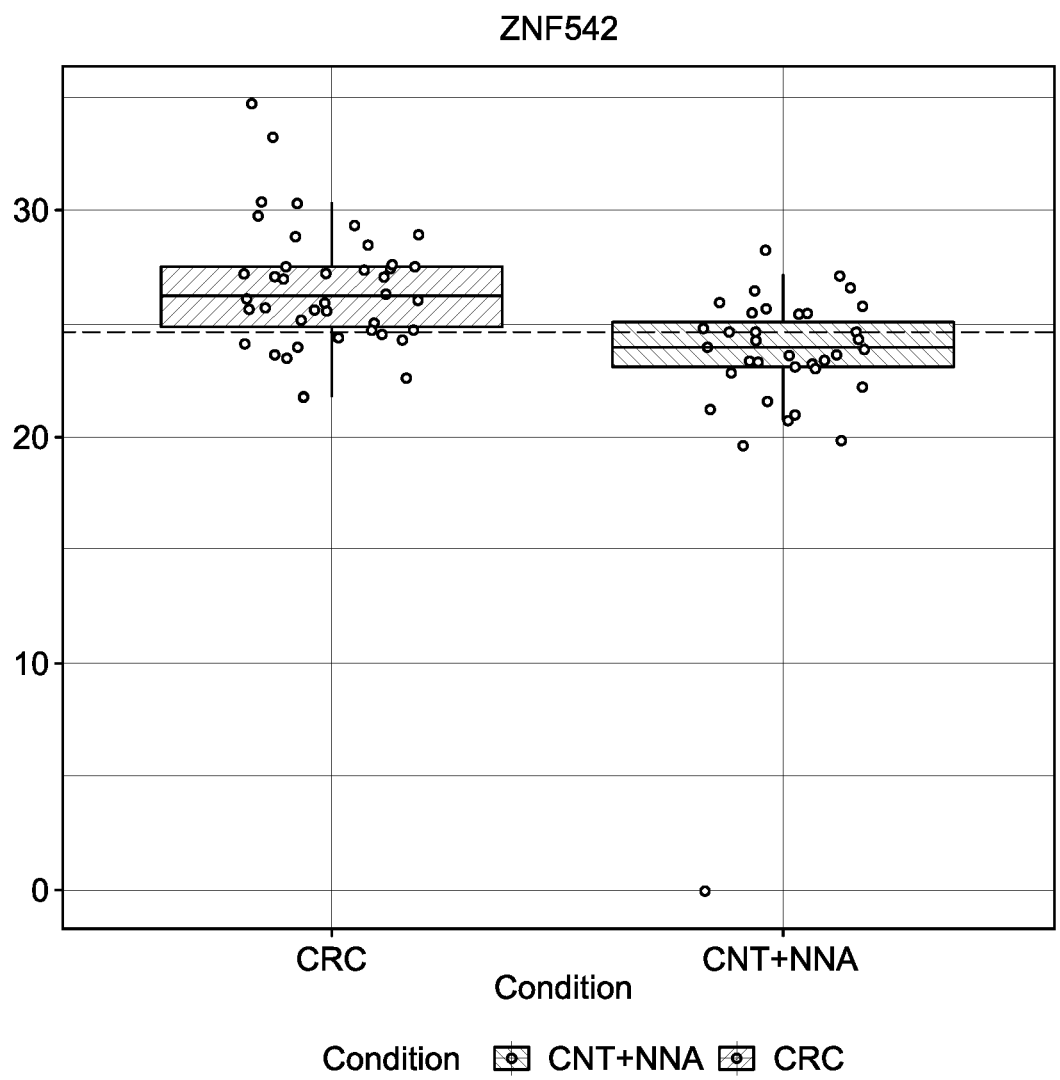
FIG. 18 is a graph representing Ct values from MSRE-qPCR of ZNF542 '525 for subjects with colorectal cancer and control subjects (healthy subjects and subjects with non-advanced adenoma). Data represent the third subject group (82 subjects). For display purposes, Ct values are subtracted from 45 (45−Ct). Higher 45−Ct values correspond to higher methylation status, demonstrating hypermethylation in subjects with colorectal cancer.
Figure 19:
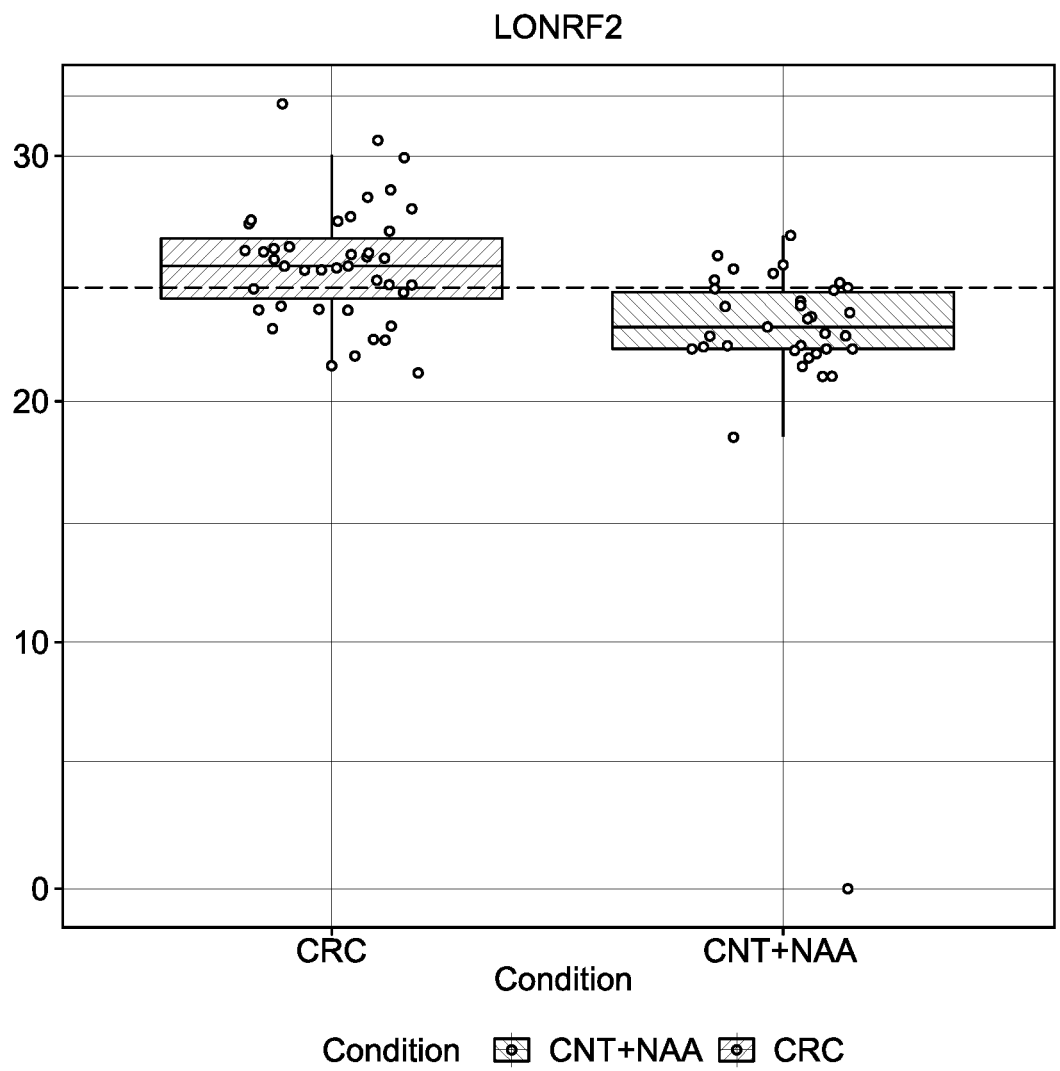
FIG. 19 is a graph representing Ct values from MSRE-qPCR of LONRF2 '281 for subjects with colorectal cancer and control subjects (healthy subjects and subjects with non-advanced adenoma). Data represent the third subject group (82 subjects). For display purposes, Ct values are subtracted from 45 (45−Ct). Higher 45−Ct values correspond to higher methylation status, demonstrating hypermethylation in subjects with colorectal cancer.

Notwithstanding the sufficiency and utility of all tested panels for screening for colorectal cancer, those of skill in the art will appreciate that the 28-DMR panel provided increased sensitivity and comparable specificity as compared to all other DMR panels indicated in Table 15. For the avoidance of any doubt, all of the panels tested, e.g., as described in Tables 7-14, are individually alone sufficient (e.g., in both sensitivity and specificity), and useful, for clinical screening of colorectal cancer. Analysis of the third subject group using the 28 colorectal cancer DMR panel showed general sensitivity for diagnosis of colorectal cancer of 79%, with 75% sensitivity for localized (early) cancer and 84% sensitivity for advanced cancer. Data also revealed specificity of 87% at AUC 82% (FIG. 11). A ROC curve analysis of the second validation group data based on a 28-marker panel identified by the SVM model is provided in FIG. 11.

Thus, evaluation of the performance of the 28 colorectal cancer DMR panel and subsets thereof reveal that both the full panel and each of the various subsets of 2, 3, 5, 8, and 15 of the 28 colorectal cancer DMRs are individually sufficient for clinical screening of colorectal cancer (See Tables 7-14). For instance, to highlight just one example, the 3-DMR subset (Table 9) achieved good separation of col-

TABLE 14

Proof-of-principle DMR panel

| gene | chr | start | end | width | uid |
|------|-----|-------|-----|-------|-----|
| PDGFD | chr11 | 104163499 | 104164026 | 528 | PDGFD_chr11_104163499_104164026 |
| FGF14 | chr13 | 101919879 | 102403137 | 483259 | FGF14_chr13_101919879_102403137 |
| ALK | chr19 | 58439728 | 58440994 | 1267 | ALK_chr19_58439728_58440994 |
| LONRF2 | chr2 | 29193215 | 29922286 | 729072 | LONRF2_chr2_29193215_29922286 |
| JAM2 | chr2 | 68293114 | 68320928 | 27815 | JAM2_chr2_68293114_68320928 |

Example 4. Further Validation of Methylation Biomarkers by MSRE-qPCR

To verify the predictive power of methylation biomarker DMRs for colorectal cancer, data derived from MSRE-qPCR analysis of samples from the 133 subjects of the first and second subject groups identified in Example 3 (see FIGS. 2 and 3) were further analyzed. Monte-Carlo cross-validation was used over 50 runs and random forest algorithm was used for feature ranking and markers with VIP>2 orectal cancer subjects from control subjects, demonstrating sufficient performance for clinical screening of colorectal cancer, at least in part as demonstrated by the determined sensitivity of 60% and specificity of 87% (Table 15).

SVM-model characteristics are described in Table 16. Input support SVM Vectors and their coefficiency (weight) values are given in Table 17 (due to the size of Table 17, Table 17 is presented in several portions, with the coefficients and gene names repeated in each portion for reference). For prediction purposes the provided information was used in combination with predict( ) function in R-package (see Hypertext Transfer Protocol Secure (HTTPS)://cran.r-project.org/web/packages/e1071/index.html).

TABLE 15

Accuracy metrics for application of 28 colorectal cancer DMR panel and subsets thereof to third subject group

|  | 2 | 3 | 5 | 8 | 15 | 28 |
|---|---|---|---|---|---|---|
| AUC | 0.77 | 0.82 | 0.83 | 0.83 | 0.82 | 0.82 |
| AUC_CI_LOW | 0.67 | 0.73 | 0.73 | 0.74 | 0.73 | 0.72 |
| AUC_CI_HIGH | 0.87 | 0.91 | 0.92 | 0.92 | 0.92 | 0.92 |
| Sensitivity | 0.63 | 0.60 | 0.65 | 0.53 | 0.72 | 0.79 |
| Specificity | 0.79 | 0.87 | 0.82 | 0.87 | 0.79 | 0.87 |

TABLE 16

SVM-model input characteristics

| vars | value |
|---|---|
| type | 0 |
| kernel | 2 |
| cost | 1 |
| degree | 3 |
| gamma | 0.035714 |
| coef0 | 0 |
| nu | 0.5 |
| epsilon | 0.1 |
| nclasses | 2 |
| rho | −0.73551 |
| probA | −2.14936 |
| probB | −0.10114 |
| sigma | 0 |

TABLE 17

SVM Vectors

| coefs | GSG1L<br>GSG1L '861 | 7NF492_2<br>7NF492 '499 | ZNF568_2<br>ZNF568 '252 | ZNF568_1<br>ZNF568 '405 | ZNF542_2<br>ZNF542 '525 |
|---|---|---|---|---|---|
| 1 | 0.166333806 | 0.423405118 | −0.939531248 | 0.275236404 | −0.052862411 |
| 1 | 0.183718034 | −2.19255911 | −0.092363545 | −0.327541264 | 0.309450278 |
| 0.160992568 | −0.094429617 | −2.19255911 | −0.939531248 | −0.413652359 | 0.137466406 |
| 1 | 0.475386751 | 0.318930431 | −0.147777884 | 0.019978514 | 0.164983826 |
| 1 | −0.152377044 | 0.473593938 | 1.146062978 | 0.429006217 | 0.574305439 |
| 1 | 0.315065536 | 0.442866089 | 0.835406834 | 0.041506288 | 0.55940017 |
| 0.539110203 | −0.428593114 | 0.344536972 | 0.864793226 | −0.0507556 | 0.174156299 |
| 1 | 0.143154835 | −2.19255911 | 0.848840613 | −0.373672208 | 0.025103611 |
| 0.228841426 | −0.16396653 | 0.392677269 | −0.939531248 | −0.0507556 | 0.161544148 |
| 1 | 0.691723813 | 0.288202582 | −0.939531248 | 0.232180856 | 0.641952428 |
| 1 | 0.152812739 | 0.548365038 | 0.897538063 | 0.321367348 | 0.6259006 |
| 0.086502196 | 0.152812739 | 0.413162502 | −0.939531248 | −0.318315075 | 0.260148235 |
| 1 | 0.058165275 | 0.455157229 | −0.939531248 | −0.035378619 | 0.421813073 |
| 0.022981588 | −0.055797999 | −2.19255911 | −0.939531248 | −0.469009492 | 0.310596837 |
| 0.199753156 | 0.029191561 | 0.425453641 | −0.939531248 | −0.192223828 | 0.392002536 |
| 0.640672506 | 0.401986676 | 0.512515881 | 0.731295044 | −0.352144434 | −2.050168434 |
| 0.488436741 | 0.11224954 | −2.19255911 | −0.939531248 | −0.327541264 | −2.050168434 |
| 0.290813367 | 0.038849466 | 0.455157229 | 0.842963334 | 0.038430892 | 0.370217912 |
| 0.93438076 | −0.165898111 | 0.292299628 | 0.996612184 | −0.293711905 | 0.182182213 |
| 1 | 0.34597083 | 0.531976852 | −0.939531248 | 0.622756182 | 0.534175869 |
| 0.177133374 | 0.291886565 | 0.201140342 | 0.931122511 | 0.312141159 | 0.439011461 |
| 0.363673626 | −0.252819252 | 0.199091819 | −0.939531248 | −0.232203979 | 0.408054364 |
| 0.372869951 | −0.022961123 | −2.19255911 | −0.939531248 | −0.438255529 | −2.050168434 |
| 0.180416799 | −0.0152348 | 0.246207854 | −0.939531248 | −0.247580961 | 0.130587052 |
| 1 | 1.837151292 | 1.131169911 | −0.939531248 | 1.084065621 | 1.180835225 |
| 0.236974727 | −4.54286045 | 0.032137172 | −0.240135117 | −0.619703909 | −2.050168434 |
| 0.433173404 | −4.54286045 | −2.19255911 | −0.939531248 | −0.40442617 | 0.427545869 |
| 0.037394649 | 0.15474432 | −2.19255911 | −0.939531248 | −0.204525413 | 0.471115116 |
| 1 | 0.245528623 | 0.455157229 | −0.939531248 | −0.207600809 | 0.380536944 |
| 0.263636311 | −4.54286045 | −2.19255911 | −0.939531248 | −1.72992196 | −2.050168434 |
| 1 | 0.682065908 | 0.557583393 | 1.034394689 | 0.828807731 | 0.838014042 |
| 1 | −0.042276933 | 0.55553487 | 0.775294438 | 0.158371346 | 0.349579848 |
| 1 | 0.025328399 | 0.467448369 | 0.848001002 | −0.524366624 | 0.018224256 |
| 0.26169536 | −4.54286045 | −2.19255911 | −0.939531248 | −7.963750185 | −2.050168434 |
| 0.1799778 | 0.295749727 | 0.267717349 | −0.939531248 | 0.226030064 | 0.467675439 |
| 0.898868481 | −0.18521392 | 0.324051739 | −0.939531248 | −0.023077034 | 0.29339845 |
| 0.042908076 | 0.019533657 | 0.191921987 | −0.939531248 | −0.622779305 | 0.275053503 |
| 0.140898434 | −4.54286045 | 0.204213127 | −0.939531248 | −0.567422172 | 0.123707697 |
| 0.140415448 | 0.293818146 | −2.19255911 | −0.939531248 | −0.699664211 | 0.061793503 |
| 1 | 0.166333806 | 0.135587597 | −0.939531248 | −0.044604807 | 0.459649525 |
| 0.108835219 | −0.378372011 | 0.333270094 | −0.939531248 | −0.604326927 | −2.050168434 |
| 1 | 0.608665834 | 0.370143513 | 0.901736119 | 0.641208559 | 0.750875547 |
| −1 | 0.322791859 | −2.19255911 | 1.066299914 | 0.186049912 | 0.550227697 |
| −1 | 0.025328399 | −2.19255911 | −0.497895756 | 0.026129307 | 0.433278665 |
| −1 | 0.311202374 | 0.387555961 | −0.939531248 | −0.182997639 | 0.5192706 |
| −1 | −0.059661161 | 0.322003216 | 1.020121298 | 0.422855425 | 0.403468127 |
| −1 | 0.403918257 | 0.612893521 | 0.959669292 | 0.468986368 | 0.589210708 |
| −1 | 0.172128548 | 0.145830214 | 0.701908652 | 0.182974516 | 0.491753181 |
| −1 | −0.16396653 | 0.411113978 | −0.939531248 | −0.336767452 | 0.473408235 |
| −1 | 0.336312926 | 0.694834453 | −0.939531248 | 0.819581542 | 0.740556515 |
| −0.27309104 | 1.360050807 | 0.923244798 | 1.68509337 | 2.378807448 | 1.22669759 |
| −1 | 2.101777876 | 1.346264856 | 1.939495565 | 3.255295383 | 1.550027268 |

TABLE 17-continued

SVM Vectors

| | | | | | |
|---|---|---|---|---|---|
| −1 | 0.712971203 | 0.404968409 | 0.776634049 | 0.475137161 | −2.050168434 |
| −0.675668601 | 0.382670867 | 0.677422005 | 1.048668079 | 0.579700634 | 0.674056084 |
| −1 | 0.245528623 | 0.403944147 | −0.939531248 | −0.545894398 | −2.050168434 |
| −0.228886868 | 1.516508861 | 0.993918852 | 1.713640151 | 2.252716201 | 1.264534042 |
| −1 | 0.523676274 | 0.505346049 | 0.922726399 | 0.272161008 | 0.602969418 |
| −0.253709663 | 0.53719734 | 0.671276435 | −0.939531248 | 0.186049912 | 0.764634257 |
| −1 | −0.007508476 | −2.19255911 | −0.939531248 | −0.284485716 | 0.336967697 |
| −1 | 0.465728846 | 0.297420936 | −0.939531248 | 0.075335647 | 0.648831783 |
| −1 | 0.206897005 | 0.52480702 | 0.981499183 | 0.066109458 | 0.583477912 |
| −1 | 0.626050062 | 0.583189934 | −0.939531248 | 0.804204561 | 0.654564579 |
| −1 | 0.094865312 | 0.356828111 | 0.968065404 | 0.112240402 | 0.397735331 |
| −1 | 0.04850737 | −2.19255911 | −0.939531248 | −1.041033197 | 0.29339845 |
| −1 | −0.241229766 | −2.19255911 | 0.913490675 | −0.14916828 | 0.136319847 |
| −1 | 0.419370905 | −2.19255911 | −0.939531248 | 0.099938817 | 0.659150816 |
| −1 | 0.228144395 | 0.438769043 | 0.834567222 | 0.413629236 | 0.549081138 |
| −1 | 0.45220778 | 0.585238457 | 0.886623117 | −0.103037336 | 0.838014042 |
| −1 | 0.237802299 | 0.444914613 | −0.939531248 | 0.078411043 | 0.295691568 |

| coefs | ZNF542_1<br>ZNF542 '502 | ZNF471_2<br>ZNF471 '527 | ZNF471_1<br>ZNF471 '558 | ZNF471_3<br>ZNF471 '662 | ZNF132_2<br>ZNF132 '268 |
|---|---|---|---|---|---|
| 1 | 0.210023302 | 0.448781467 | 0.381358009 | 0.276869984 | −0.079808848 |
| 1 | 0.096511033 | −1.701659498 | 0.111027436 | 0.245615084 | 0.220719423 |
| 0.160992568 | 0.011755205 | 0.491015986 | 0.192253523 | 0.011882788 | 0.004011962 |
| 1 | 0.075322076 | 0.362552655 | 0.179561947 | 0.342097602 | 0.355650484 |
| 1 | 0.438561338 | 0.531490735 | 0.353436542 | 0.351609963 | 0.275918493 |
| 1 | 0.322022075 | 0.502454502 | 0.314092655 | 0.193976554 | 0.091921755 |
| 0.539110203 | 0.007214715 | 0.395108431 | 0.091990071 | 0.143696932 | −0.206562268 |
| 1 | 0.010241709 | 0.604521258 | 0.298862764 | 0.238820541 | 0.200275323 |
| 0.228841426 | 0.010241709 | −1.701659498 | −0.009542539 | −3.291624259 | 0.120543333 |
| 1 | 0.477912258 | 0.220891037 | 0.146563849 | 0.172234015 | 0.333161974 |
| 1 | 0.228185265 | 0.381030258 | 0.097066702 | 0.160003836 | 0.380183404 |
| 0.086502196 | 0.116186493 | −1.701659498 | −0.38775151 | −0.122649173 | −0.237228418 |
| 1 | 0.194888333 | 0.592202857 | 0.357244014 | 0.299971432 | 0.053077803 |
| 0.022981588 | −0.13808099 | −1.701659498 | −0.060308843 | −3.291624259 | −0.186118168 |
| 0.199753156 | 0.15705091 | 0.495415416 | 0.260788035 | 0.227949271 | −0.034831828 |
| 0.640672506 | 0.120726984 | −1.701659498 | 0.215098361 | 0.210283458 | 0.183920043 |
| 0.488436741 | 0.05867361 | −1.701659498 | 0.02853219 | 0.007806062 | −0.341493329 |
| 0.290813367 | 0.063214101 | 0.449661352 | 0.10848912 | 0.248332902 | 0.433338064 |
| 0.93438076 | 0.043538641 | 0.359912998 | 0.034877978 | −0.051985921 | 0.051033393 |
| 1 | 0.211536799 | −1.701659498 | −0.187224606 | −0.012577568 | 0.482403904 |
| 0.177133374 | 0.264509192 | 0.375750943 | 0.046300397 | −3.291624259 | −7.69E−05 |
| 0.363673626 | 0.073808579 | 0.258726128 | 0.171947002 | −0.049268103 | −0.204517858 |
| 0.372869951 | −3.407234345 | 0.527971191 | 0.279825399 | 0.138261297 | −0.406914449 |
| 0.180416799 | −3.407234345 | −1.701659498 | −0.136458301 | −3.291624259 | −0.406914449 |
| 1 | 1.345145995 | 1.182606248 | 1.282459921 | 1.285180239 | 1.347189337 |
| 0.236974727 | −3.407234345 | −1.701659498 | −2.980640533 | −0.383559643 | −0.085942078 |
| 0.433173404 | 0.001160727 | 0.382790029 | 0.060261131 | −0.069651734 | −0.110474998 |
| 0.037394649 | −0.468023319 | 0.373111285 | 0.013302299 | −0.008500842 | −0.257672518 |
| 1 | 0.455209804 | 0.5957224 | 0.409279477 | 0.446733572 | 0.001967552 |
| 0.263636311 | −3.407234345 | −1.701659498 | −2.980640533 | 0.049932232 | −5.066124854 |
| 1 | 0.721585263 | 0.52181199 | 0.325815074 | 0.344815419 | 0.791109815 |
| 1 | 0.060187107 | 0.342315281 | 0.10848912 | −0.046550286 | 0.071477493 |
| 1 | −0.038190193 | 0.419745234 | 0.317900128 | 0.173592923 | −0.413047679 |
| 0.26169536 | −3.407234345 | 0.529730963 | 0.213829203 | −0.096829908 | −0.366026249 |
| 0.1799778 | 0.155537413 | −1.701659498 | −0.034925691 | 0.191258736 | −5.066124854 |
| 0.898868481 | 0.278130664 | 0.655554636 | 0.5463485 | 0.405966311 | −0.192251398 |
| 0.042908076 | 0.079862567 | 0.491895872 | 0.225251622 | 0.179028558 | 0.020367243 |
| 0.140898434 | 0.051106125 | −1.701659498 | −0.243067541 | −3.291624259 | −5.066124854 |
| 0.140415448 | −0.074514119 | −1.701659498 | −2.980640533 | 0.154568201 | −0.304693949 |
| 1 | 0.128294469 | 0.220011151 | −0.135189143 | 0.202130006 | 0.106232463 |
| 0.108835219 | −3.407234345 | −1.701659498 | −2.980640533 | −3.291624259 | 0.026500473 |
| 1 | 0.526344159 | −1.701659498 | −0.140265774 | 0.233384906 | 0.603024094 |
| −1 | 0.368940479 | 0.572845368 | 0.377550536 | 0.036343145 | 0.177786813 |
| −1 | 0.31445459 | 0.503334388 | 0.298862764 | 0.181746375 | 0.132809793 |
| −1 | 0.240293241 | 0.61683966 | 0.287440345 | 0.473911746 | 0.378138994 |
| −1 | 0.134348456 | 0.407426833 | 0.248096459 | 0.279587802 | −0.165674068 |
| −1 | 0.424939866 | 0.570205711 | 0.39151127 | 0.305407067 | 0.523292104 |
| −1 | 0.347751522 | 0.558767195 | 0.404202846 | 0.324431789 | 0.210497373 |
| −1 | 0.325049069 | 0.280723273 | 0.102143332 | 0.295894706 | −0.286294258 |
| −1 | 0.577803055 | 0.540289593 | 0.434662629 | 0.505166646 | 0.881063855 |
| −0.27309104 | 1.379956424 | 0.847369747 | 0.820486547 | 0.710361859 | 1.046661066 |
| 1 | 1.806762557 | 1.486166858 | 1.711435198 | 1.720031023 | 2.25286297 |
| −1 | 0.343211032 | 0.614200002 | 0.400395374 | 0.426349941 | 0.654134345 |
| −0.675668601 | 0.455209804 | 0.547328679 | 0.424509368 | 0.408684128 | 0.776798945 |
| −1 | −0.012460745 | 0.328237108 | −0.031118218 | −0.007141934 | 0.077610723 |
| −0.228886868 | 1.384496915 | 1.151810244 | 1.269768345 | 1.328665317 | 1.330834057 |
| −1 | 0.391642933 | 0.754981735 | 0.631382061 | −3.291624259 | 0.118498923 |

TABLE 17-continued

SVM Vectors

| | | | | | |
|---|---|---|---|---|---|
| −0.253709663 | 0.741260723 | 1.184366019 | 1.220271198 | 1.031064312 | 0.367916944 |
| −1 | −0.147161972 | −1.701659498 | −0.187224606 | −0.133520443 | 0.065344263 |
| −1 | 0.536938638 | 0.610680459 | 0.408010319 | 0.446733572 | 0.425160424 |
| −1 | 0.188834345 | −1.701659498 | 0.259518877 | 0.237461632 | 0.480359494 |
| −1 | 0.421912872 | 0.484856786 | 0.344552438 | 0.318996154 | 0.692978135 |
| −1 | 0.190347842 | 0.604521258 | 0.31663097 | 0.270075441 | −0.024609778 |
| −1 | 0.060187107 | 0.410946376 | 0.26332635 | 0.282305619 | 0.108276873 |
| −1 | 0.043538641 | 0.546448794 | 0.279825399 | 0.100211854 | −0.063453568 |
| −1 | 0.443101829 | 0.402147518 | 0.429585999 | 0.274152167 | 0.055122213 |
| −1 | 0.446128822 | 0.451421124 | 0.211290888 | 0.308124884 | 0.220719423 |
| −1 | 0.774557655 | 0.410946376 | 0.221444149 | 0.145055841 | 0.717511055 |
| −1 | 0.110132505 | 0.549968337 | 0.243019828 | −0.111777904 | 0.273874083 |

| coefs | ZNF132_1<br>ZNF132 '415 | JAM2<br>JAM2 '320 | MCIDAS_1<br>MCIDAS '855 | MCIDAS_2<br>MCIDAS '003 | PDGFD_1<br>PDGFD '388 |
|---|---|---|---|---|---|
| 1 | 0.238896666 | 0.406419198 | 0.492859834 | 0.416450063 | 0.046762915 |
| 1 | −0.397730773 | −2.423671354 | 0.320276073 | 0.121123394 | −0.124572283 |
| 0.160992568 | −0.170552517 | −2.423671354 | −2.052243039 | 0.091026409 | −0.261640442 |
| 1 | 0.347202579 | 0.464995238 | 0.485753444 | 0.245273459 | 0.426555938 |
| 1 | 0.120024323 | 0.545266109 | 0.761887461 | 0.544362251 | −0.027482338 |
| 1 | 0.006435195 | 0.297945048 | 0.524330991 | 0.190722673 | 0.235231633 |
| 0.539110203 | −0.693590827 | 0.228521593 | 0.262409754 | 0.038356684 | −0.53577676 |
| 1 | −0.550944015 | 0.287097633 | 0.044142056 | −0.183608583 | 0.20382018 |
| 0.228841426 | −0.352823443 | 0.214419954 | 0.199467441 | 0.028951376 | 0.121008168 |
| 1 | 0.299653641 | 0.447639374 | 0.58219731 | 0.501097835 | 0.423700352 |
| 1 | 0.26795435 | 0.317470395 | 0.572045325 | 0.252797705 | 0.266643087 |
| 0.086502196 | −0.487545432 | 0.333741518 | 0.359868819 | 0.213295412 | −0.16169491 |
| 1 | 0.088325031 | 0.395571783 | 0.40961355 | 0.333683353 | 0.126719341 |
| 0.022981588 | −1.155872162 | −2.423671354 | −2.052243039 | 0.019546069 | −0.669989332 |
| 0.199753156 | −0.231309492 | −2.423671354 | 0.225862604 | 0.043999869 | −0.17882843 |
| 0.640672506 | 0.407959554 | 0.378215919 | 0.320276073 | 0.141815072 | 0.152419621 |
| 0.488436741 | −0.410938811 | −0.105578787 | 0.311139286 | −4.590935879 | −0.375863908 |
| 0.290813367 | −0.049038566 | 0.15367443 | −2.052243039 | 0.168149934 | 0.358021859 |
| 0.93438076 | −0.614342598 | 0.187301416 | −0.001541881 | −0.078269134 | −0.624299946 |
| 1 | 0.415884377 | 0.216589437 | 0.588288502 | 0.241511336 | 0.469389738 |
| 0.177133374 | 0.135873968 | 0.230691076 | 0.443115103 | 0.15122038 | 0.132430514 |
| 0.363673626 | −0.025264097 | 0.130894859 | 0.318245676 | 0.072215793 | −0.247362509 |
| 0.372869951 | −0.281500037 | 0.267572287 | 0.200482639 | −0.042528964 | −0.190250776 |
| 0.180416799 | −6.542110115 | 0.37930066 | 0.199467441 | −0.245683615 | −0.435831227 |
| 1 | 1.855560534 | 1.410889819 | 1.44105532 | 1.953277379 | 1.120463492 |
| 0.236974727 | −0.71208208 | −2.423671354 | −2.052243039 | −4.590935879 | −0.344452455 |
| 0.433173404 | 0.104174677 | −0.128358358 | 0.297941704 | −0.078269134 | 0.292343366 |
| 0.037394649 | −0.226026277 | 0.150420206 | −2.052243039 | 0.049643054 | −0.104583177 |
| 1 | −0.424146849 | 0.275165477 | −2.052243039 | 0.072215793 | 0.063896435 |
| 0.263636311 | −6.542110115 | −0.08605344 | −2.052243039 | −0.591798947 | −7.103626036 |
| 1 | 0.69061157 | 0.407503939 | 0.605546878 | 0.314872738 | 1.134741426 |
| 1 | −0.038472135 | 0.309877205 | 0.161905093 | −0.241921492 | 0.295198953 |
| 1 | −0.014697667 | 0.199233573 | 0.256318562 | −0.24004043 | −0.407275361 |
| 0.26169536 | −0.878503361 | 0.122216927 | 0.038050865 | −4.590935879 | −0.415842121 |
| 0.1799778 | −0.125645187 | 0.492113775 | 0.581182112 | 0.352493969 | −7.103626036 |
| 0.898868481 | 0.101533069 | −2.423671354 | 0.41671994 | 0.02142713 | −0.470098267 |
| 0.042908076 | −0.281500037 | −2.423671354 | 0.402507159 | −0.345379879 | −0.235940162 |
| 0.140898434 | −0.532452762 | 0.177538743 | −2.052243039 | −0.040647902 | −0.707111958 |
| 0.140415448 | −0.136211617 | −2.423671354 | 0.160889894 | 0.143696133 | −0.147416977 |
| 1 | 0.006435195 | 0.180792967 | 0.542604565 | 0.326159107 | −0.304474242 |
| 0.108835219 | −0.292066467 | −2.423671354 | 0.051248446 | −0.388644296 | −0.632866706 |
| 1 | 0.574380834 | 0.446554633 | 0.667473992 | 0.598913037 | 0.812060135 |
| −1 | 0.196630944 | 0.384724368 | 0.345656038 | 0.218938597 | 0.363733032 |
| −1 | 0.180781298 | 0.228521593 | 0.117236355 | −0.119652489 | 0.546490577 |
| −1 | 0.471358137 | 0.249131681 | 0.483677471 | −0.149749474 | 0.483667671 |
| −1 | −0.022622489 | 0.469334204 | 0.406567954 | 0.145577195 | −0.007493231 |
| −1 | 0.574380834 | 0.309877205 | 0.617729261 | 0.132409764 | 0.466534151 |
| −1 | 0.030209663 | 0.205742022 | 0.451236692 | −0.003026671 | −0.010348818 |
| −1 | 0.02228484 | 0.213335212 | 0.123327546 | 0.237749213 | 0.078174368 |
| −1 | 0.970621979 | 0.511639122 | 0.606562077 | 0.311110614 | 0.689269909 |
| −0.27309104 | 0.981188409 | 1.000857535 | 1.309079503 | 1.5507302 | 1.465989476 |
| −1 | 2.840880179 | 1.538889315 | 1.185225275 | 1.65795071 | 2.031395631 |
| −1 | 0.574380834 | 0.560452489 | 0.650215616 | 0.561291805 | 0.777793095 |
| −0.675668601 | 1.139684867 | 0.64072336 | 0.720264319 | 0.572578175 | 0.892016561 |
| −1 | −0.178477339 | 0.079912009 | 0.120281951 | 0.008259699 | 0.123863754 |
| −0.228886868 | 1.945375193 | 1.1646535 | 1.014671911 | 1.069178434 | 1.683014061 |
| −1 | 0.064550562 | 0.462825755 | 0.547665058 | 0.290418859 | 0.395144485 |
| −0.253709663 | 0.79099266 | 0.783909237 | 0.578136516 | 0.538719066 | 0.709259016 |
| −1 | −0.276216822 | −2.423671354 | 0.205558632 | −0.010550917 | −0.298763069 |
| −1 | 0.36833544 | 0.443300408 | 0.530422182 | 0.094788532 | 0.400855659 |
| −1 | 0.36833544 | 0.212250471 | 0.372051202 | 0.143696133 | 0.226664874 |
| −1 | 0.761934976 | 0.514893347 | 0.615698864 | 0.350612908 | 0.717825776 |

TABLE 17-continued

| | | SVM Vectors | | | |
|---|---|---|---|---|---|
| −1 | 0.283803995 | 0.427029286 | 0.48169265 | 0.243392397 | 0.149564034 |
| −1 | −0.659249928 | 0.18296245 | 0.281698527 | −0.371714741 | 0.118152581 |
| −1 | −0.241875922 | 0.190555641 | 0.327382464 | −0.001145609 | −0.116005524 |
| −1 | 0.149082006 | 0.290351858 | 0.572045325 | 0.388234139 | 0.452256218 |
| −1 | 0.347202579 | 0.420520837 | 0.494890231 | 0.164387811 | 0.466534151 |
| −1 | 1.055153423 | 0.579977836 | 0.862392122 | 0.811472996 | 0.186686661 |
| −1 | −0.123003579 | −2.423671354 | 0.184239462 | 0.29418106 | 0.443689458 |

| coefs | PDGFD_2 PDGFD '921 | ST6GALNAC5 ST6GALNAC5 '456 | ZNF492_1 ZNF492 '069 | CNRIP1_1 CNRIP1 '272 | LONRF2_1 LONRF2 '281 |
|---|---|---|---|---|---|
| 1 | 1.302789852 | 0.466406944 | −0.240707793 | −0.064165795 | 0.182108844 |
| 1 | −0.682617737 | 0.569041467 | −0.17761095 | −0.307307386 | −0.063816882 |
| 0.160992568 | −0.682617737 | 0.705281983 | −0.150569446 | 0.093547669 | −0.189987472 |
| 1 | −0.682617737 | 0.569041467 | 0.176933218 | 0.189928119 | 0.325387311 |
| 1 | 1.475318586 | 0.828806718 | −0.132541776 | 0.498783653 | 0.197078236 |
| 1 | −0.682617737 | −1.277471664 | 0.08679487 | 0.38268902 | 0.201355206 |
| 0.539110203 | −0.682617737 | −1.277471664 | −0.210661677 | 0.019071866 | 0.100846431 |
| 1 | −0.682617737 | 0.367405503 | 0.056748754 | −0.149593922 | 0.090154008 |
| 0.228841426 | −0.682617737 | 0.246605578 | 0.194960887 | 0.161452077 | −0.098032635 |
| 1 | 1.096640133 | 0.76522781 | 0.480398989 | 0.178975795 | 0.534958799 |
| 1 | −0.682617737 | 0.792475913 | 0.065762589 | 0.119833246 | 0.338218218 |
| 0.086502196 | 1.281555546 | −1.277471664 | −0.327841529 | −0.079499049 | −0.207095348 |
| 1 | −0.682617737 | 0.638978265 | 0.149891714 | 0.369546231 | 0.333941249 |
| 0.022981588 | −0.682617737 | −1.277471664 | −0.360892257 | −3.744146627 | −0.585607118 |
| 0.199753156 | −0.682617737 | −1.277471664 | −0.162587892 | −0.042261148 | −5.029378066 |
| 0.640672506 | −0.682617737 | 0.586298599 | 0.23702545 | −0.07073719 | −0.22634171 |
| 0.488436741 | 1.209005001 | −1.277471664 | 0.017688804 | −0.348926217 | −0.160048688 |
| 0.290813367 | −0.682617737 | 0.638069995 | 0.110831763 | −0.007213711 | 0.165000968 |
| 0.93438076 | 1.368262294 | 0.469131755 | −0.57421968 | −0.379592724 | −0.014631737 |
| 1 | −0.682617737 | −1.277471664 | 0.423311368 | 0.316975076 | 0.498604562 |
| 0.177133374 | −0.682617737 | 0.554509145 | 0.243034673 | 0.222785091 | 0.154308545 |
| 0.363673626 | −0.682617737 | 0.566316656 | −0.369906092 | −0.186831823 | −0.068093851 |
| 0.372869951 | −0.682617737 | −1.277471664 | −0.231693959 | −0.06635626 | −0.435913198 |
| 0.180416799 | −0.682617737 | −1.277471664 | −1.154109717 | −2.41672497 | −0.136525357 |
| 1 | −0.682617737 | 1.508192759 | 1.468916202 | 2.071537366 | 0.917747538 |
| 0.236974727 | −0.682617737 | −1.277471664 | −0.330846141 | −4.848140877 | −5.029378066 |
| 0.433173404 | −0.682617737 | 0.542701634 | 0.056748754 | −0.243783907 | 0.263371258 |
| 0.037394649 | −0.682617737 | −1.277471664 | 0.149891714 | −0.362069006 | −0.068093851 |
| 1 | −0.682617737 | 0.620812863 | 0.336177632 | 0.045357444 | −0.311881093 |
| 0.263636311 | −0.682617737 | −1.277471664 | −7.154319065 | −0.734448018 | −5.029378066 |
| 1 | 1.438158551 | −1.277471664 | 1.072307472 | 0.660878047 | 0.791576948 |
| 1 | 1.220506917 | 0.624445943 | 0.131864044 | −0.048832542 | −0.016770221 |
| 1 | −0.682617737 | 0.609913622 | −0.204652454 | −0.160546246 | −0.269111401 |
| 0.26169536 | −0.682617737 | −1.277471664 | −7.154319065 | 0.207451837 | −5.029378066 |
| 0.1799778 | −0.682617737 | −1.277471664 | 0.534481997 | 0.062881162 | 0.607667275 |
| 0.898868481 | −0.682617737 | 0.698015822 | −0.02137147 | 0.268784851 | −0.040293551 |
| 0.042908076 | −0.682617737 | −1.277471664 | −0.339859976 | −0.567972695 | −0.326850485 |
| 0.140898434 | −0.682617737 | −1.277471664 | −0.571215068 | −0.537306188 | −0.442328652 |
| 0.140415448 | −0.682617737 | −1.277471664 | −0.144560222 | −3.146149742 | 0.111538853 |
| 1 | −0.682617737 | −1.277471664 | −0.02137147 | 0.178975795 | 0.505020015 |
| 0.108835219 | −0.682617737 | −1.277471664 | −0.318827695 | −4.848140877 | −0.463713497 |
| 1 | −0.682617737 | −1.277471664 | 0.429320592 | 0.560116667 | 0.757361195 |
| −1 | 1.29571175 | −1.277471664 | 0.092804093 | −0.136451133 | 0.107261884 |
| −1 | −0.682617737 | 0.76613608 | 0.393265253 | −0.094832302 | 0.220601567 |
| −1 | −0.682617737 | −1.277471664 | 0.324159186 | 0.260022992 | 0.415203663 |
| −1 | 1.442582365 | 0.811549586 | −0.108504883 | 0.424307851 | 0.248401866 |
| −1 | −0.682617737 | 0.770677431 | 0.579551171 | 0.380498555 | 0.637606059 |
| −1 | 1.147071609 | −1.277471664 | −0.084467991 | −0.241593443 | 0.094430977 |
| −1 | −0.682617737 | 0.633528644 | 0.342186855 | 0.216213697 | 0.081600069 |
| −1 | −0.682617737 | 0.821540557 | 0.792878594 | 0.619259216 | 0.872839362 |
| −0.27309104 | 2.042451502 | 1.427356719 | 1.264602614 | 1.732015325 | 1.51224625 |
| −1 | −0.682617737 | 1.5981115 | 2.0127509 | 2.529344505 | 2.128129808 |
| −1 | 1.308398191 | 0.435525761 | 0.480398989 | 0.316975076 | 0.733837865 |
| −0.675668601 | −0.682617737 | 0.837889419 | 0.726777139 | 0.551354808 | 0.63332909 |
| −1 | −0.682617737 | −1.277471664 | 0.083790259 | −0.06635626 | −0.040293551 |
| −0.228886868 | 1.923893295 | 1.317456036 | 1.381782466 | 1.839348099 | 1.349721423 |
| −1 | −0.682617737 | 0.856963091 | 0.315145351 | 0.343260654 | 0.259094289 |
| −0.253709663 | 1.235547883 | 1.01500209 | 0.964141455 | 1.026685666 | 0.729560896 |
| −1 | 1.354106091 | −1.277471664 | −0.048412651 | −0.099213232 | −0.076647789 |
| −1 | −0.682617737 | 0.617179782 | 0.393265253 | 0.303832288 | 0.505020015 |
| −1 | 1.269168867 | 0.629895564 | 0.342186855 | 0.481259935 | 0.421619117 |
| −1 | 1.248819324 | 0.831531528 | 0.315145351 | 0.308213217 | 0.673960297 |
| −1 | 1.336410836 | 0.788842833 | −0.168597115 | 0.371736696 | 0.188524298 |
| −1 | 1.133800168 | 0.567224926 | −0.126532553 | −0.134260668 | −0.001800829 |
| −1 | −0.682617737 | −1.277471664 | −0.105500272 | −0.090451373 | 0.216324598 |
| −1 | −0.682617737 | 0.717997765 | 0.390260641 | 0.411165062 | 0.513573954 |

TABLE 17-continued

SVM Vectors

| | | | | | |
|---|---|---|---|---|---|
| −1 | −0.682617737 | 0.735254897 | 0.231016227 | 0.384879485 | 0.541374253 |
| −1 | −0.682617737 | 1.01681863 | 0.231016227 | 1.147161228 | 0.703899081 |
| −1 | 1.284209834 | −1.277471664 | 0.158905548 | −0.103594161 | −0.574914695 |

| coefs | LONRF2_2<br>LONRF2 '387 | ADAMTS2_2<br>ADAMTS2 '254 | ADAMTS2_1<br>ADAMTS2 '284 | ADAMTS2_3<br>ADAMTS2 '328 | ALK<br>ALK '434 |
|---|---|---|---|---|---|
| 1 | 0.816278101 | −1.226540092 | 0.479237716 | 0.308464228 | 1.224961864 |
| 1 | 0.707526931 | 0.608032885 | 0.377972809 | 0.108720604 | −0.67135809 |
| 0.160992568 | −1.17952336 | −1.226540092 | −1.402761026 | −3.569757964 | −0.67135809 |
| 1 | 0.644016248 | 0.715511247 | 0.413319994 | 0.342021157 | −0.67135809 |
| 1 | 1.028560383 | 0.889956898 | 0.805960341 | 0.757487893 | −0.67135809 |
| 1 | 0.704916903 | 0.774210969 | 0.512674242 | 0.359598595 | −0.67135809 |
| 0.539110203 | −1.17952336 | 0.74444773 | 0.34931293 | −0.159734825 | −0.67135809 |
| 1 | −1.17952336 | −1.226540092 | −1.344485938 | −0.001537876 | 1.290071562 |
| 0.228841426 | −1.17952336 | 0.651850986 | 0.265243951 | 0.155061125 | −0.67135809 |
| 1 | 0.849338456 | 0.647717203 | 0.611073161 | 0.319649871 | 1.311232214 |
| 1 | 0.788437801 | 0.675826929 | 0.455354484 | 0.27330935 | −0.67135809 |
| 0.086502196 | 0.548315219 | −1.226540092 | 0.357910549 | 0.155061125 | 1.30146576 |
| 1 | 0.564845397 | 0.690708548 | −1.172526662 | 0.340423208 | 1.271352524 |
| 0.022981588 | −1.17952336 | −1.226540092 | −1.818329276 | −0.437777949 | −0.67135809 |
| 0.199753156 | 0.650976323 | 0.717164761 | 0.579547294 | 0.310062177 | −0.67135809 |
| 0.640672506 | −1.17952336 | 0.763463132 | 0.44580119 | 0.290886789 | −0.67135809 |
| 0.488436741 | −1.17952336 | 0.617127208 | 0.287216525 | −0.153343029 | −0.67135809 |
| 0.290813367 | 0.570935463 | 0.735353407 | 0.491656997 | 0.316453973 | −0.67135809 |
| 0.93438076 | −1.17952336 | 0.666732606 | 0.444845861 | 0.169442666 | −0.67135809 |
| 1 | −0.840219712 | 0.793226371 | 0.47350574 | 0.389959626 | −0.67135809 |
| 0.177133374 | −1.17952336 | −1.226540092 | 0.355044906 | 0.129493941 | −0.67135809 |
| 0.363673626 | 0.538745116 | −1.226540092 | 0.304412453 | −0.142157387 | −0.67135809 |
| 0.372869951 | −1.17952336 | −1.226540092 | 0.354089577 | 0.111916502 | −0.67135809 |
| 0.180416799 | 0.499594695 | −1.226540092 | −1.818329276 | −3.569757964 | −0.67135809 |
| 1 | 0.880658793 | 1.437269791 | 1.395398525 | 1.705071643 | 1.21519541 |
| 0.236974727 | 1.17952336 | −1.226540092 | −1.818329276 | −3.569757964 | −0.67135809 |
| 0.433173404 | −1.17952336 | −1.226540092 | 0.347402271 | 0.057586237 | −0.67135809 |
| 0.037394649 | −1.17952336 | −1.226540092 | −1.818329276 | −3.569757964 | −0.67135809 |
| 1 | −1.17952336 | 0.671693146 | 0.532736158 | −0.081435325 | −0.67135809 |
| 0.263636311 | −1.17952336 | −1.226540092 | −1.818329276 | −3.569757964 | −0.67135809 |
| 1 | 0.846728428 | 0.660118553 | 0.491656997 | 0.417124759 | 1.282746721 |
| 1 | 0.650106314 | −1.226540092 | 0.401856042 | −0.322725622 | −0.67135809 |
| 1 | 0.640536211 | −1.226540092 | 0.567128013 | 0.254133962 | −0.67135809 |
| 0.26169536 | 0.519604911 | −1.226540092 | 0.536557475 | 0.284494993 | −0.67135809 |
| 0.1799778 | 0.525694976 | 0.613820181 | 0.533691487 | 0.266917554 | −0.67135809 |
| 0.898868481 | −1.17952336 | 0.719645031 | 0.407588018 | −0.172518417 | 1.353553518 |
| 0.042908076 | 0.605735837 | 0.541065597 | 0.508852925 | 0.28928884 | −0.67135809 |
| 0.140898434 | −1.17952336 | −1.226540092 | −1.818329276 | −3.569757964 | −0.67135809 |
| 0.140415448 | −1.17952336 | −1.226540092 | −1.818329276 | −0.332313316 | −0.67135809 |
| 1 | 0.771037614 | −1.226540092 | 0.249958682 | −0.099012764 | −0.67135809 |
| 0.108835219 | 0.456094228 | 0.611339911 | −1.818329276 | −0.242828173 | −0.67135809 |
| 1 | 0.865868634 | −1.226540092 | 0.373196163 | 0.410732963 | −0.67135809 |
| −1 | −1.17952336 | 0.717991517 | 0.575725977 | 0.27330935 | 1.293327047 |
| −1 | −0.466985698 | 0.596458292 | 0.295814489 | 0.17903036 | −0.67135809 |
| −1 | 0.741457296 | 0.675000172 | 0.399945384 | 0.287609091 | −0.67135809 |
| −1 | 0.838898344 | 0.763463132 | 0.587189928 | 0.35160885 | −0.67135809 |
| −1 | 0.764077539 | 0.795706641 | 0.609162503 | 0.4315063 | −0.67135809 |
| −1 | 0.920679223 | −1.226540092 | 0.530825499 | 0.139081635 | 1.257516713 |
| −1 | −1.17952336 | 0.608859641 | 0.236584071 | 0.044802645 | −0.67135809 |
| −1 | 0.706656922 | 0.8155488 | 0.656928968 | 0.760683791 | 1.349484162 |
| −0.27309104 | 1.371344069 | 1.329791428 | 1.262607751 | 1.433420315 | 1.942796285 |
| −1 | 1.875079486 | 1.591046526 | 1.560670496 | 2.013475797 | 2.200793463 |
| −1 | 0.539615126 | 0.697322601 | 0.524138194 | 0.247742166 | −0.67135809 |
| −0.675668601 | 0.845858419 | 0.760982862 | 0.572859599 | 0.501816055 | 1.410524504 |
| −1 | −1.17952336 | 0.765943402 | 0.286261196 | −0.031898906 | 1.241239289 |
| −0.228886868 | 1.433114734 | 1.358727911 | 1.26451841 | 1.481358784 | 1.862223034 |
| −1 | 0.513514845 | 0.884996358 | 0.706606092 | 0.567331964 | 1.322626411 |
| −0.253709663 | 1.074670879 | 0.993301477 | 0.790675072 | 0.69996173 | 1.619689409 |
| −1 | −1.17952336 | 0.583230186 | 0.338804308 | 0.166246768 | −0.67135809 |
| −1 | 0.977229831 | 0.713030978 | 0.603430527 | 0.370784238 | −0.67135809 |
| −1 | 0.684036679 | 0.742794216 | 0.471595082 | 0.263721656 | −0.67135809 |
| −1 | 0.950259541 | 0.777517995 | 0.650241663 | 0.568929913 | 1.333206737 |
| −1 | 0.843248391 | 0.738660433 | 0.582413282 | 0.319649871 | −0.67135809 |
| −1 | −1.17952336 | −1.226540092 | 0.244226706 | −0.234838428 | −0.67135809 |
| −1 | 0.717097034 | −1.226540092 | 0.458220472 | 0.107122655 | −0.67135809 |
| −1 | 0.689256735 | −1.226540092 | 0.342625625 | 0.242948319 | −0.67135809 |
| −1 | 0.864128615 | 0.785785562 | 0.597698551 | 0.452279637 | −0.67135809 |
| −1 | 1.023340327 | −1.226540092 | 0.275752573 | 0.006451869 | 1.64085006 |
| −1 | −1.17952336 | 0.702283141 | 0.516495559 | 0.334031412 | −0.67135809 |

TABLE 17-continued

| | SVM Vectors | | |
|---|---|---|---|
| coefs | FGF14<br>FGF14 '577 | DMRT1<br>DMRT1 '934 | CNRIP1_2<br>CNRIP1 '232 |
| 1 | 0.955300844 | 1.131612847 | 0.296394201 |
| 1 | −0.93950462 | −0.701307401 | 0.101966839 |
| 0.160992568 | 0.846924723 | −0.701307401 | −2.336804129 |
| 1 | −0.93950462 | −0.701307401 | 0.230086604 |
| 1 | 1.296419127 | 1.516680127 | 0.443619546 |
| 1 | 0.974844079 | −0.701307401 | 0.407656103 |
| 0.539110203 | −0.93950462 | 1.17300758 | 0.203114022 |
| 1 | −0.93950462 | −0.701307401 | 0.261554616 |
| 0.228841426 | −0.93950462 | 1.199962289 | 0.268297762 |
| 1 | −0.93950462 | −0.701307401 | 0.368321087 |
| 1 | 0.734106957 | −0.701307401 | 0.228962746 |
| 0.086502196 | 0.761645152 | −0.701307401 | 0.236829749 |
| 1 | −0.93950462 | −0.701307401 | 0.536899725 |
| 0.022981588 | −0.93950462 | −0.701307401 | −2.336804129 |
| 0.199753156 | 0.771416769 | −0.701307401 | 0.216600313 |
| 0.640672506 | 0.814944884 | −0.701307401 | 0.384055093 |
| 0.488436741 | −0.93950462 | −0.701307401 | 0.073870399 |
| 0.290813367 | −0.93950462 | −0.701307401 | 0.268297762 |
| 0.93438076 | −0.93950462 | −0.701307401 | 0.027792238 |
| 1 | 0.960630817 | −0.701307401 | 0.3997891 |
| 0.177133374 | −0.93950462 | −0.701307401 | 0.092975978 |
| 0.363673626 | 0.769640112 | −0.701307401 | 0.317747496 |
| 0.372869951 | −0.93950462 | −0.701307401 | 0.225591173 |
| 0.180416799 | −0.93950462 | 1.108508811 | −2.336804129 |
| 1 | 1.728146955 | 1.533045486 | 1.467453809 |
| 0.236974727 | −0.93950462 | −0.701307401 | −2.336804129 |
| 0.433173404 | −0.93950462 | −0.701307401 | 0.284031768 |
| 0.037394649 | −0.93950462 | −0.701307401 | −2.336804129 |
| 1 | 0.834488119 | −0.701307401 | 0.25031604 |
| 0.263636311 | −0.93950462 | −0.701307401 | −2.336804129 |
| 1 | 0.798066635 | −0.701307401 | 0.540271298 |
| 1 | −0.93950462 | −0.701307401 | −0.045258506 |
| 1 | 0.853143025 | 1.17300758 | −2.336804129 |
| 0.26169536 | −0.93950462 | −0.701307401 | 0.450362691 |
| 0.1799778 | −0.93950462 | 1.108508811 | 0.412151533 |
| 0.898868481 | −0.93950462 | −0.701307401 | 0.412151533 |
| 0.042908076 | −0.93950462 | −0.701307401 | 0.205361737 |
| 0.140898434 | −0.93950462 | −0.701307401 | −2.336804129 |
| 0.140415448 | 0.748320219 | −0.701307401 | −2.336804129 |
| 1 | 0.726111997 | −0.701307401 | 0.384055093 |
| 0.108835219 | −0.93950462 | −0.701307401 | −2.336804129 |
| 1 | −0.93950462 | 1.12487417 | 0.598711893 |
| −1 | 0.830046474 | −0.701307401 | 0.314375923 |
| −1 | −0.93950462 | −0.701307401 | 0.078365829 |
| −1 | −0.93950462 | −0.701307401 | 0.552633732 |
| −1 | 0.867356287 | 1.072890087 | 0.532404295 |
| −1 | 1.115200039 | −0.701307401 | 0.452610406 |
| −1 | 0.632837467 | 1.202850294 | 0.307632777 |
| −1 | 0.974844079 | −0.701307401 | 0.05476482 |
| −1 | 0.946417555 | −0.701307401 | 0.585225602 |
| −0.27309104 | 1.777893371 | 2.092355709 | 1.213461994 |
| −1 | 1.891599465 | 2.29451603 | 1.66750046 |
| −1 | 0.822939843 | −0.701307401 | −2.336804129 |
| −0.675668601 | 0.790071676 | −0.701307401 | 0.593092605 |
| −1 | −0.93950462 | −0.701307401 | 0.252563755 |
| −0.228886868 | 1.602004256 | 1.983574202 | 1.266283301 |
| −1 | 1.124971657 | 1.209588971 | 0.542519013 |
| −0.253709663 | 1.057458663 | −0.701307401 | 0.829102699 |
| −1 | 1.010377234 | −0.701307401 | 0.017677519 |
| −1 | 0.846924723 | 1.254834377 | 0.354834796 |
| −1 | 1.049463703 | 1.121023497 | 0.557129162 |
| −1 | −0.93950462 | −0.701307401 | 0.488573849 |
| −1 | 0.948194213 | 0.985287281 | 0.479582988 |
| −1 | −0.93950462 | −0.701307401 | −2.336804129 |
| −1 | −0.93950462 | −0.701307401 | 0.325614499 |
| −1 | 0.225094519 | −0.701307401 | 0.389674381 |
| −1 | 0.870909602 | 1.213439644 | 0.285155626 |
| −1 | −0.93950462 | 1.568664209 | 0.829102699 |
| −1 | −0.93950462 | −0.701307401 | 0.224467316 |

Example 5. Various Individual Methylation Biomarkers are Each Highly Informative Evaluation of the performance of individual colorectal cancer DMRs from among the 28 colorectal cancer DMR panel reveal that various individual colorectal cancer DMRs are sufficient for screening of colorectal cancer (See FIGS. 12-19). For selected colorectal cancer DMRs, FIGS. 12-19 show methylation status of the indicated DMR in colorectal cancer samples and control samples. Results are displayed as the MSRE-qPCR Ct value subtracted from 45 (i.e., 45−Ct value) for display purposes. Data provided in this Example, as well as data provided by the present Examples cumulatively (including, e.g., FIGS. 5-9), demonstrate that for each individual colorectal cancer DMR the methylation status signal is sufficiently stable across subject groups to permit clinical screening. Results presented in FIGS. 12-19 therefore confirm that methylation markers of colorectal cancer provided herein can provide a robust signal for screening of colorectal cancer. Moreover, those of skill in the art will appreciate that the present disclosure provides methylation biomarkers that are individually independently useful in screening for colorectal cancer, and specifically that methylation biomarkers provided herein are useful both individually or in combination.

Example 6. Validation of Markers

Blood plasma samples were used to determine a minimal viable DMR panel for the detection of colorectal cancer. It was found that the methylation status of DMRs was useful in distinguishing colorectal cancer not only from healthy subjects, but also from subjects suffering with other types of cancers (e.g., breast cancer, lung cancer).

Blood plasma samples from 215 subjects were analyzed using MSRE-qPCR and used as a training set to determine a minimal viable DMR panel for colorectal cancer detection. FIG. 21 presents a detailed view of the cohort of subjects used for training an algorithm to detect colorectal cancer. The training set included 93 human subjects having been diagnosed with colorectal cancer (CRC), 91 subjects having been diagnosed as being healthy, and 31 subjects diagnosed has having non-advanced adenoma (NAA). The NAA+Healthy column is the sum of the Healthy and NAA columns. For the sake of calculating specificities, all patients that did not have a colorectal cancer diagnosis were considered to be controls. FIG. 21 also indicates the colorectal cancer distribution. Colorectal cancer is classified as being localized or advanced as determined by histology. The location of colorectal cancer as determined by colonoscopy is either found to be in the proximal or distal colon.

Selected DMRs that showed potential in colorectal cancer detection were further validated using an independent validation subject set (see FIG. 22). Plasma samples of 774 human subjects were collected in Spain, Ukraine, the UK and the US. Of those 774 subjects, 152 subjects were diagnosed as having colorectal cancer (CRC). The control group included 622 subjects. 148 subjects of the control group subjects had non-advanced adenoma, and 52 of the control group subjects had non-CRC cancer (i.e., breast cancer or lung cancer). FIG. 22 sets forth the number of males and females in each group, age range, and total number of subjects. For those suffering with a cancer (i.e., colorectal, breast, or lung cancer), the cancer is classified as being localized or advanced.

A random forest feature selection algorithm was implemented for feature ranking. The algorithm utilized Monte-Carlo cross-validation over 50 sub-setting iterations on the training set of FIG. 21 to rank the pre-selected markers according to their variance of importance (VIP) in occurring in the 50 iterations. Markers with VIP>2 were further used for support-vector machine algorithm building on the training set.

Figure 23:
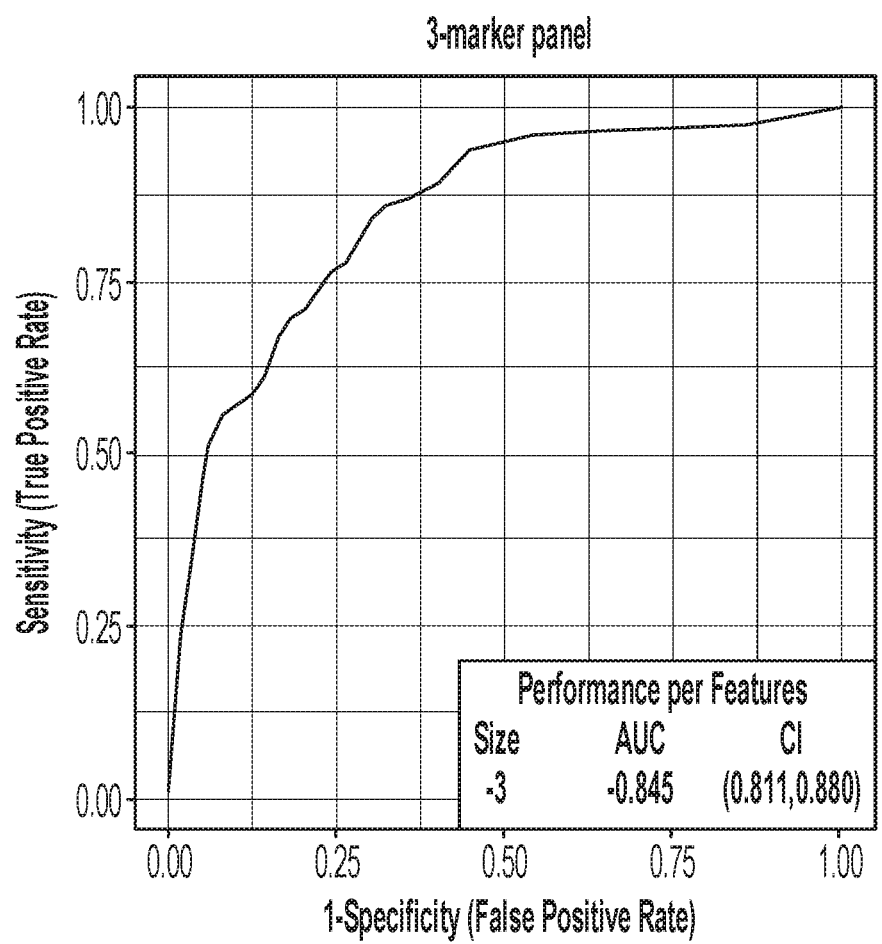
FIG. 23 is a graph showing performance of a 3-marker panel for colorectal cancer screening using DMRs of Table 18. ROC curve and performance features for all subjects of the fourth, validation subject group are shown.
Figure 24:
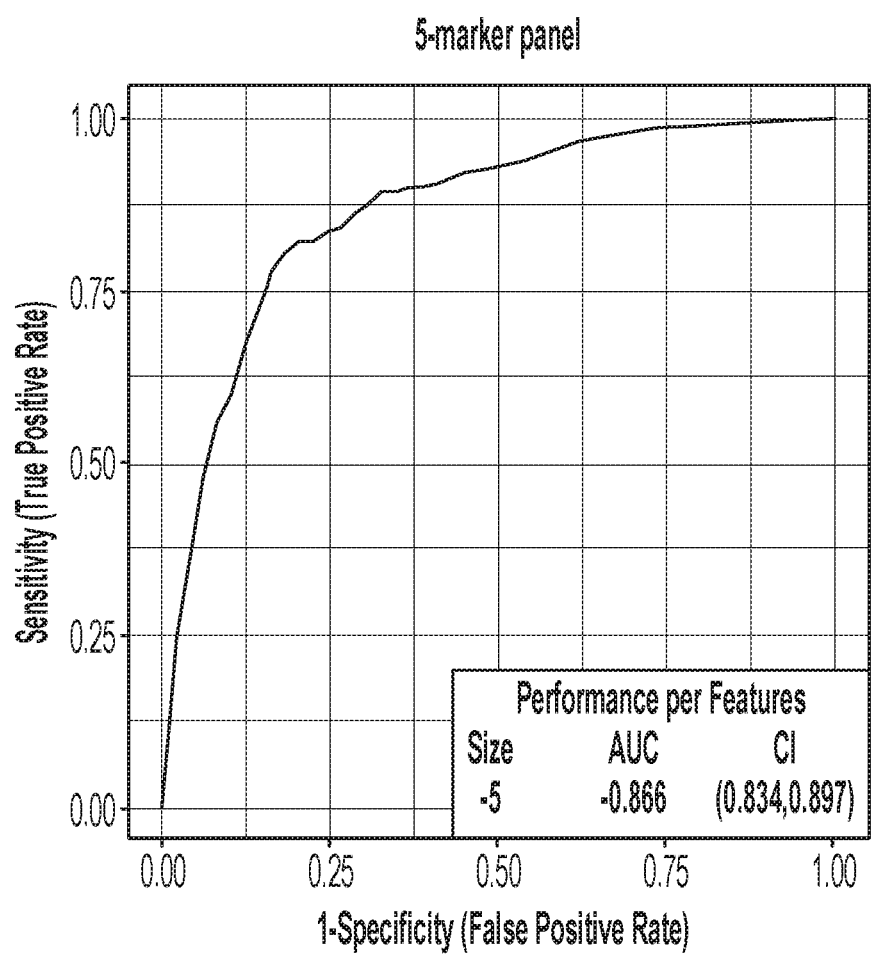
FIG. 24 is a graph showing performance of a 5-marker panel for colorectal cancer screening using DMRs of Table 19. ROC curve and performance features for all subjects of the fourth, validation subject group are shown.
Figure 25:
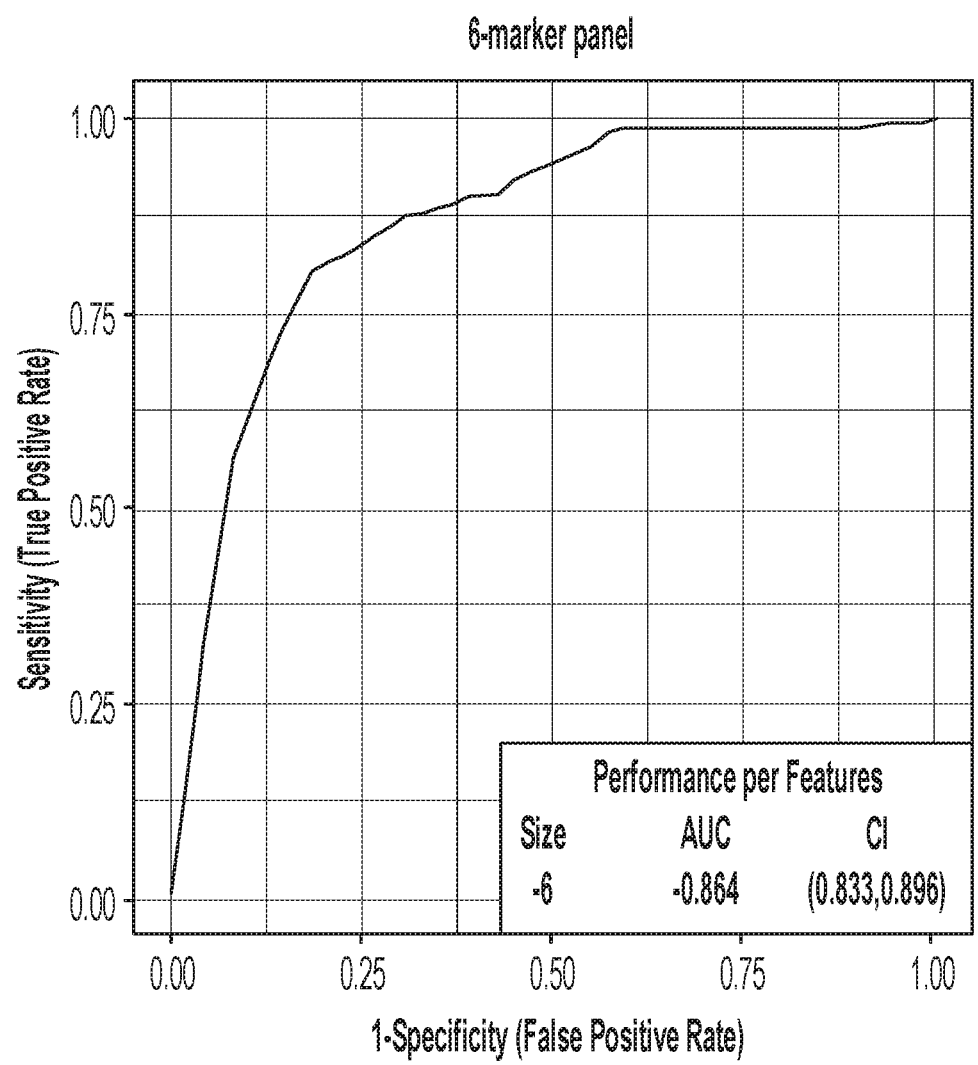
FIG. 25 is a graph showing performance of a 6-marker panel for colorectal cancer screening using DMRs of Table 20. ROC curve and performance features for all subjects of the fourth, validation subject group are shown.
Figure 26:
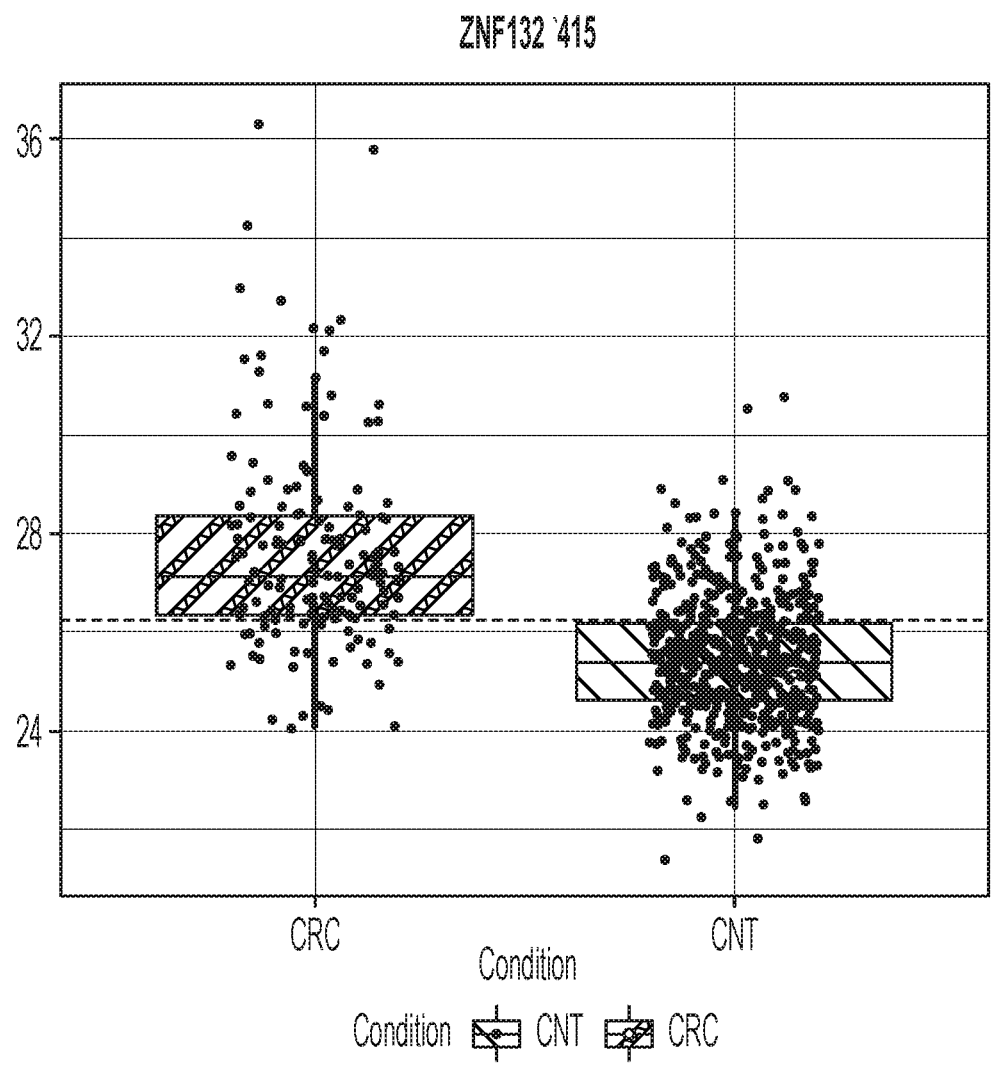
FIG. 26 is a graph representing Ct values from MSRE-qPCR of ZNF132 '415 for subjects with colorectal cancer and control subjects (healthy subjects, subjects with non-advanced adenoma, and subjects with other cancers). Data represent the fourth subject group (774 subjects). For display purposes, Ct values are subtracted from 45 (45−Ct). Higher 45−Ct values correspond to higher methylation status, demonstrating hypermethylation in subjects with colorectal cancer.
Figure 27:
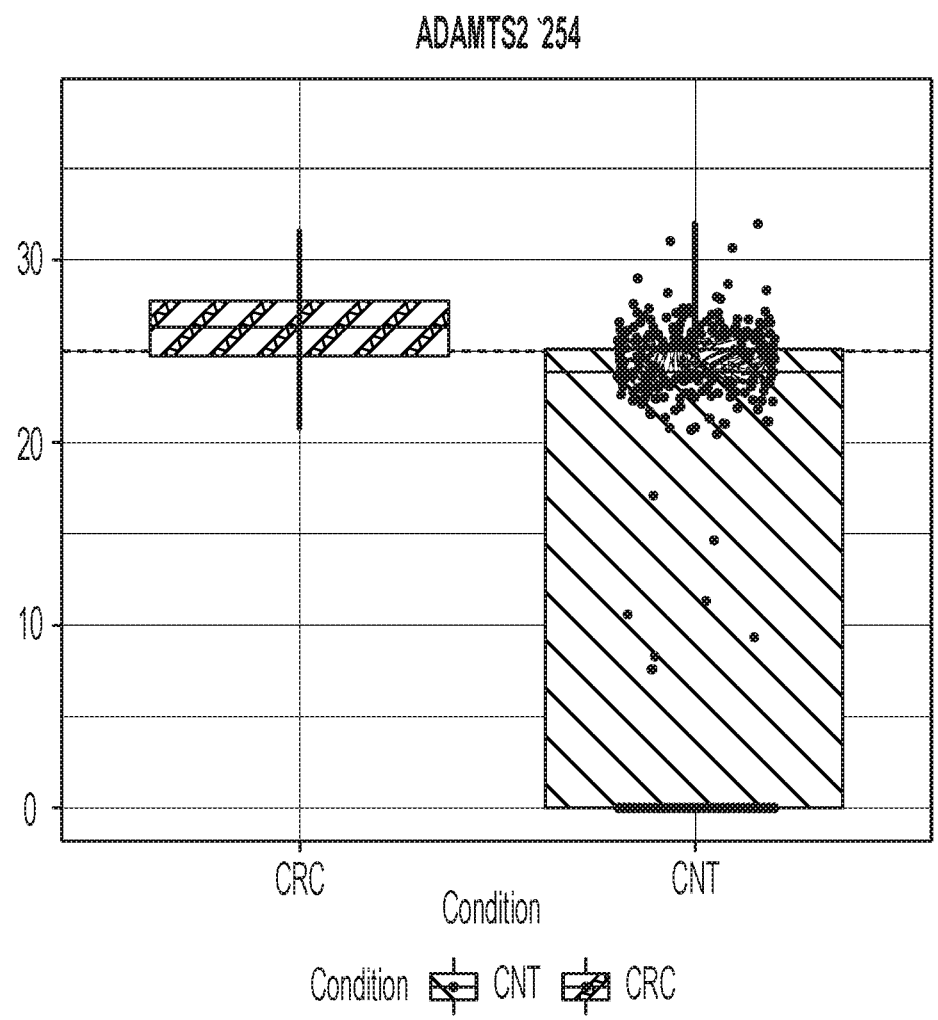
FIG. 27 is a graph representing Ct values from MSRE-qPCR of ADAMTS2 '254 for subjects with colorectal cancer and control subjects (healthy subjects, subjects with non-advanced adenoma, and subjects with other cancers). Data represent the fourth subject group (774 subjects). For display purposes, Ct values are subtracted from 45 (45−Ct). Higher 45−Ct values correspond to higher methylation status, demonstrating hypermethylation in subjects with colorectal cancer.
Figure 28:
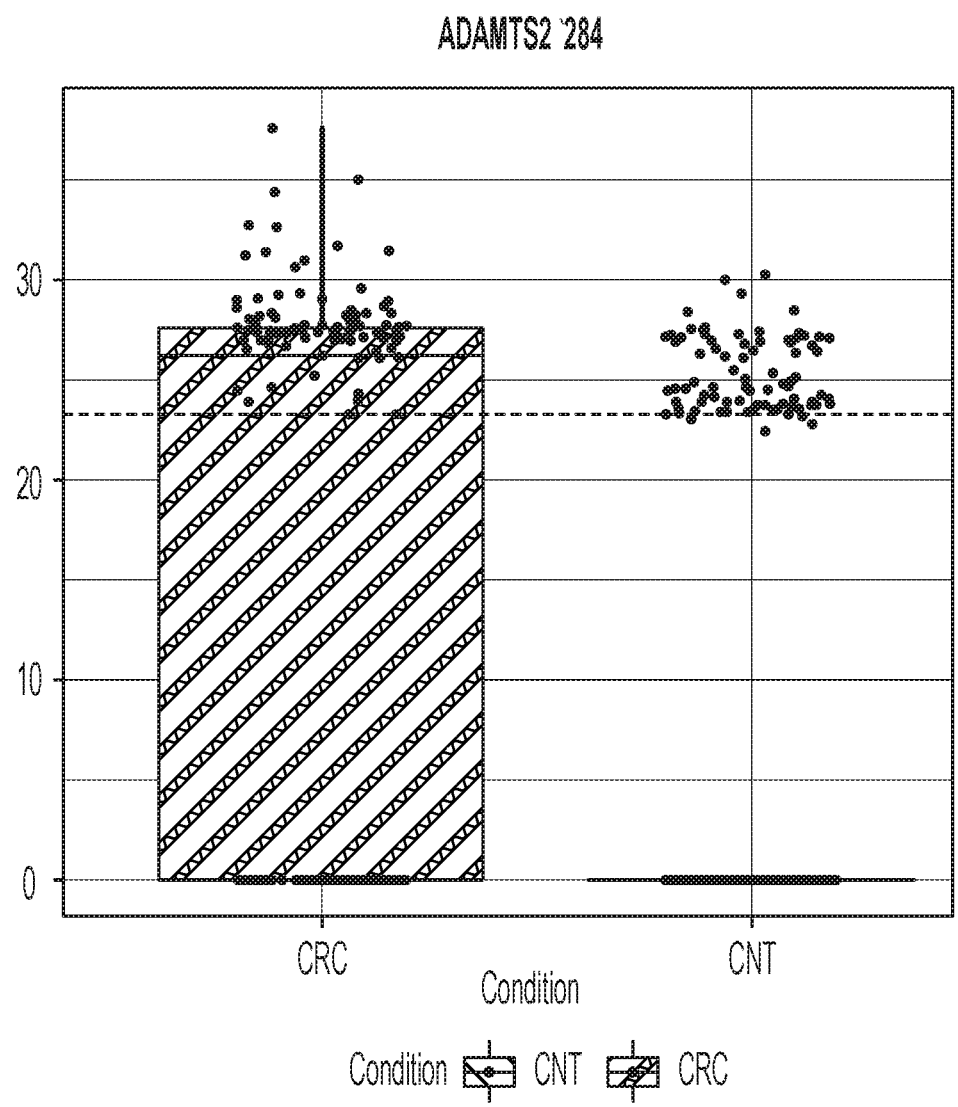
FIG. 28 is a graph representing Ct values from MSRE-qPCR of ADAMTS2 '284 for subjects with colorectal cancer and control subjects (healthy subjects, subjects with non-advanced adenoma, and subjects with other cancers). Data represent the fourth subject group (774 subjects). For display purposes, Ct values are subtracted from 45 (45−Ct). Higher 45−Ct values correspond to higher methylation status, demonstrating hypermethylation in subjects with colorectal cancer.
Figure 29:
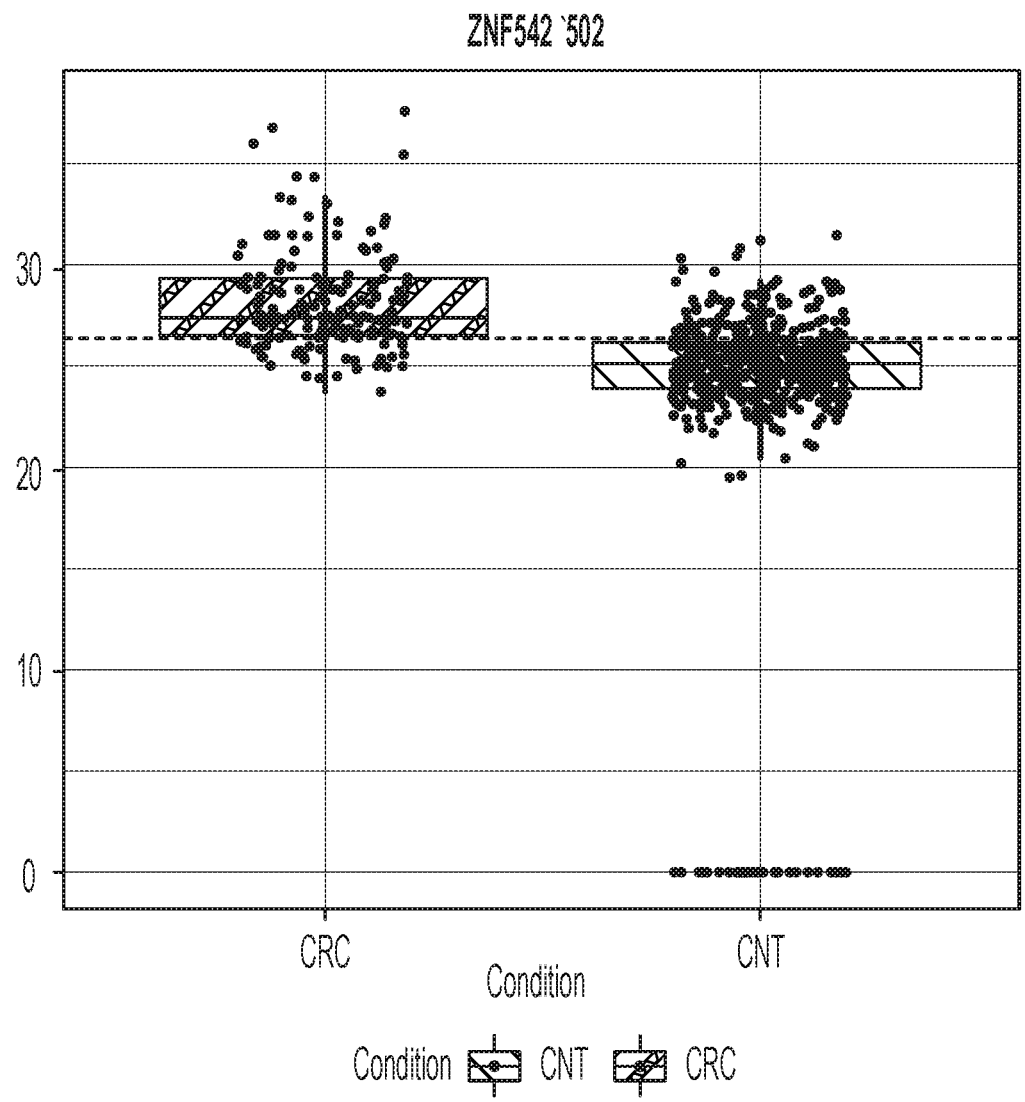
FIG. 29 is a graph representing Ct values from MSRE-qPCR of ZNF542 '502 for subjects with colorectal cancer and control subjects (healthy subjects, subjects with non-advanced adenoma, and subjects with other cancers). Data represent the fourth subject group (774 subjects). For display purposes, Ct values are subtracted from 45 (45−Ct). Higher 45−Ct values correspond to higher methylation status, demonstrating hypermethylation in subjects with colorectal cancer.
Figure 30:
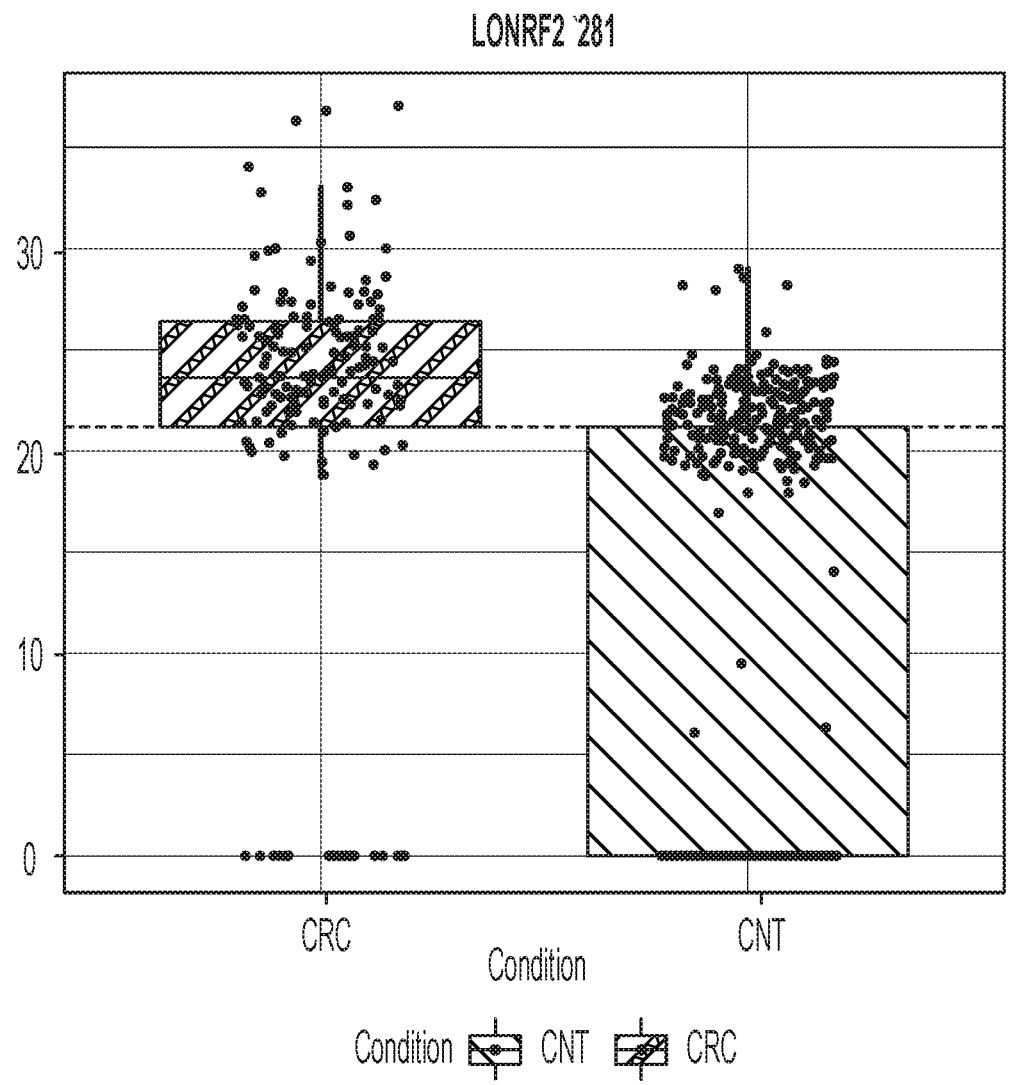
FIG. 30 is a graph representing Ct values from MSRE-qPCR of LONRF2 '281 for subjects with colorectal cancer and control subjects (healthy subjects, subjects with non-advanced adenoma, and subjects with other cancers). Data represent the fourth subject group (774 subjects). For display purposes, Ct values are subtracted from 45 (45−Ct). Higher 45−Ct values correspond to higher methylation status, demonstrating hypermethylation in subjects with colorectal cancer.
Figure 31:
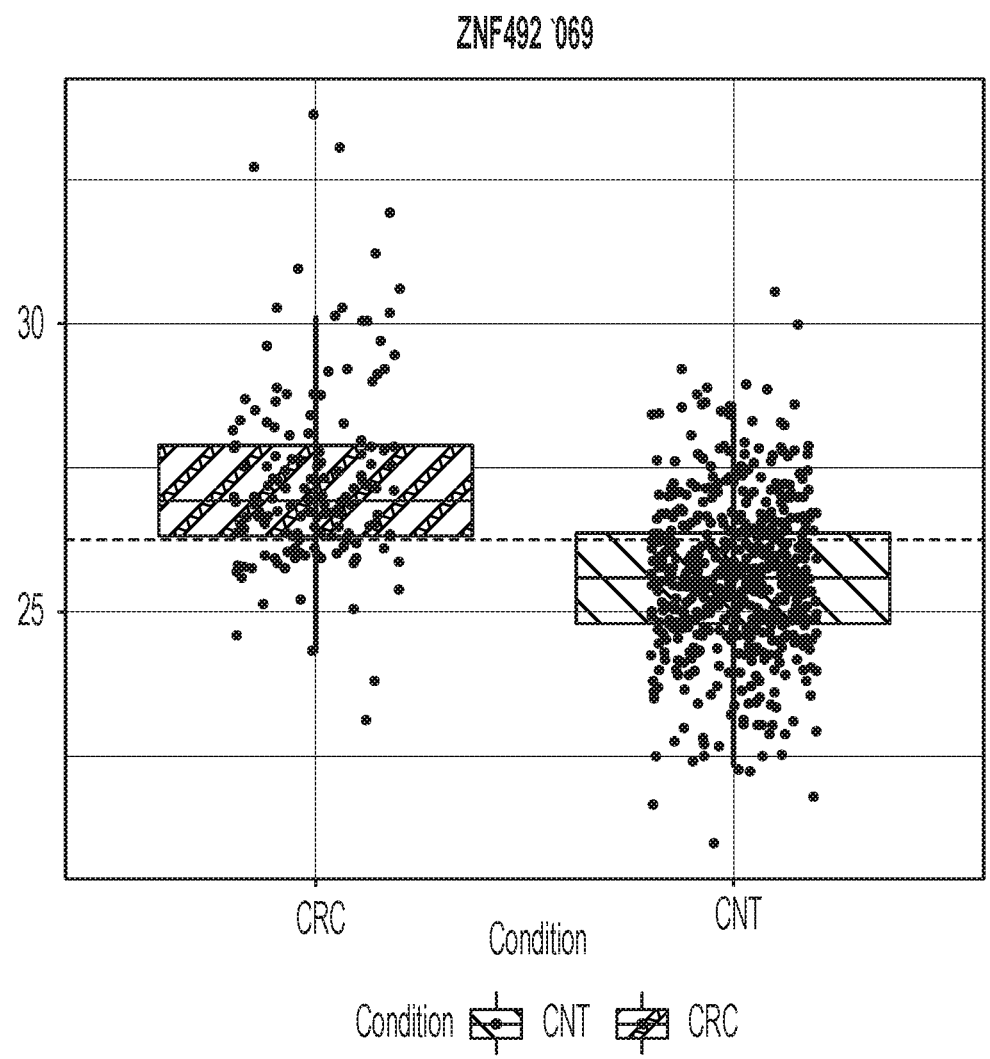
FIG. 31 is a graph representing Ct values from MSRE-qPCR of ZNF492 '069 for subjects with colorectal cancer and control subjects (healthy subjects, subjects with non-advanced adenoma, and subjects with other cancers). Data represent the fourth subject group (774 subjects). For display purposes, Ct values are subtracted from 45 (45−Ct). Higher 45−Ct values correspond to higher methylation status, demonstrating hypermethylation in subjects with colorectal cancer.

It was found that 3-DMR (FIG. 23), 5-DMR (FIG. 24), and 6-DMR (FIG. 25) panels all performed well in assessing the colorectal cancer status of subjects of the validation set (FIG. 22). Tables 18, 19, and 20 (shown below) identify the markers included in each of the 3, 5, and 6 marker panels, respectively.

TABLE 18

3 DMR Panel.

| DMR | SEQ ID NO |
|---|---|
| ZNF132 '415 | SEQ ID NO: 40 |
| ADAMTS2 '254 | SEQ ID NO: 21 |
| ADAMTS2 '284 | SEQ ID NO: 22 |

TABLE 19

5 DMR Panel.

| DMR | SEQ ID |
|---|---|
| ZNF132 '415 | SEQ ID NO: 40 |
| ADAMTS2 '254 | SEQ ID NO: 21 |
| ADAMTS2 '284 | SEQ ID NO: 22 |
| ZNF542 '502 | SEQ ID NO: 35 |
| LONRF2 '281 | SEQ ID NO: 19 |

TABLE 20

6 DMR Panel.

| DMR | SEQ ID |
|---|---|
| ZNF132 '415 | SEQ ID NO: 40 |
| ADAMTS2 '254 | SEQ ID NO: 21 |
| ADAMTS2 '284 | SEQ ID NO: 22 |
| ZNF542 '502 | SEQ ID NO: 35 |
| LONRF2 '281 | SEQ ID NO: 19 |
| ZNF492 '069 | SEQ ID NO: 42 |

Furthermore, Table 21 (below) shows the accuracy, sensitivity, specificity and AUC of each of the 3-DMR (Table 18), 5-DMR (Table 19), and 6-DMR (Table 20) panels as previously presented.

TABLE 21

| ROC Curve Analysis of Each Model | | | |
|---|---|---|---|
| | 3 DMRs (2 Genes) | 5 DMRs (4 Genes) | 6 DMRs (5 Genes) |
| AUC | 0.85 | 0.87 | 0.86 |
| Sensitivity | 0.58 | 0.60 | 0.69 |
| Specificity | 0.89 | 0.90 | 0.87 |
| Accuracy | 0.83 | 0.84 | 0.83 |

The best performing algorithm used the 6 markers of Table 20 and resulted in 69% of the colorectal cancer cases being detected at 87% specificity with total AUC of 86%. Additionally, both 3-marker and 5-marker panels performed well in classifying colorectal cancer. In the 3 marker panel, 58% of the colorectal cancer cases were detected with a specificity of 89% and AUC of 84.5%.

These findings are especially notable as high specificity was maintained even though subjects having cancer diagnoses other than colorectal cancer were included in the control group. This finding indicates that the markers in question are not generally indicative of cancer, but are specifically and surprisingly important for detecting colorectal cancer.

In some embodiments, the present disclosure includes combinations of DMRs in which each of the DMRs is, includes all of, includes a portion of, or is present in a gene identified in Table 22. In some embodiments, the present disclosure includes combinations of DMRs in which each of the DMRs is, includes all of, includes a portion of, or is present in a gene identified in Table 23. In some embodiments, the present disclosure includes combinations of DMRs in which each of the DMRs is, includes all of, includes a portion of, or is present in a gene identified in Table 24.

In some particular embodiments, a colorectal cancer methylation biomarker includes two DMRs, each of which is, includes all of, includes a portion of, or is present in a different gene identified in Table 22. In some particular embodiments, a colorectal cancer methylation biomarker includes four DMRs, each of which is, includes all of, includes a portion of, or is present in a different gene identified in Table 23. In some particular embodiments, a colorectal cancer methylation biomarker includes five DMRs, each of which is, includes all of, includes a portion of, or is present in a different gene identified in Table 24.

In various embodiments, a colorectal cancer methylation biomarker includes two or more DMRs that include all of, include a portion of, or are present in the same gene of Table 22. In various embodiments, a colorectal cancer methylation biomarker includes two or more DMRs that include all of, include a portion of, or are present in the same gene of Table 23. In various embodiments, a colorectal cancer methylation biomarker includes two or more DMRs that include all of, include a portion of, or are present in the same gene of Table 24.

TABLE 22

| Genes of DMR Panel of Table 18. |
|---|
| ZNF132 |
| ADAMTS2 |

TABLE 23

| Genes of DMR Panel of Table 19. |
|---|
| ZNF132 |
| ADAMTS2 |
| ZNF542 |
| LONRF2 |

TABLE 24

| Genes of DMR Panel of Table 20 |
|---|
| ZNF132 |
| ADAMTS2 |
| ZNF542 |
| LONRF2 |
| ZNF492 |

Example 7. Various Individual Methylation Biomarkers are Each Highly Informative Evaluation of the performance of individual colorectal cancer DMRs from among the colorectal cancer DMR panel (e.g., as set forth in Example 6) reveal that various individual colorectal cancer DMRs are sufficient for screening of colorectal cancer from not only healthy individuals but also from individuals suffering from other cancers. Univariate analysis over methylation status of each of the methylation markers as shown in Table 25 below shows a number of markers with high individual accuracy as indicated by p-values being less than 0.001.

TABLE 25

| T-Test P-Values Between CRC and Control Groups in Validation Set | |
|---|---|
| Gene Reference Name | P-value of Student's t-test |
| ZNF132 '415 | 4.52E−25 |
| ADAMTS2 '254 | 8.00E−29 |
| ADAMTS2 '284 | 1.62E−21 |
| ZNF542 '502 | 1.76E−37 |
| LONRF2 '281 | 9.26E−38 |
| ZNF492 '069 | 1.18E−25 |

For the selected colorectal cancer DMRs of Table 25, FIGS. 26-31 further show methylation status of the indicated DMR in colorectal cancer samples and control samples (i.e., of the validation group of FIG. 22). In this instance, control samples comprise healthy subjects, subjects having non-advanced adenomas, subjects having breast cancer, and subjects having lung cancer (see, FIG. 22). Results are displayed as the MSRE-qPCR Ct value subtracted from 45 (i.e., 45–Ct value) for display purposes. Data provided in this Example, as well as data provided by the present Examples cumulatively (including, e.g., FIGS. 23-25), demonstrate that for each individual colorectal cancer DMR the methylation status signal is sufficiently and surprisingly stable across subject groups to permit clinical screening, particularly in discriminating colorectal cancer from other forms of cancer. Results presented in FIGS. 23-25 therefore further confirm that methylation markers of colorectal cancer provided herein can provide a robust signal for screening of colorectal cancer. Moreover, those of skill in the art will appreciate that the present disclosure provides that these methylation biomarkers are individually useful in screening for colorectal cancer, and specifically that methylation biomarkers provided herein are useful both individually or in combination.

Other Embodiments

While we have described a number of embodiments, it is apparent that our basic disclosure and examples may provide other embodiments that utilize or are encompassed by the compositions and methods described herein. Therefore, it will be appreciated that the scope of is to be defined by that which may be understood from the disclosure and the appended claims rather than by the specific embodiments that have been represented by way of example.

All references cited herein are hereby incorporated by reference.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11001898B2). An electronic copy of the "Sequence Listing" will also be available from the USPTO upon request and payment of the fee set forth in 37 CFR 1.19(b)(3).

What is claimed is:

1. A method of screening for colorectal cancer, the method comprising:
   determining a methylation status for each of the following, in deoxyribonucleic acid (DNA) of a human subject:
   (a) a methylation locus within gene ZNF132;
   (b) a first methylation locus within gene ADAMTS2; and
   (c) a second methylation locus within gene ADAMTS2; and
   diagnosing colorectal cancer in the human subject based on said determined methylation statuses.

2. The method of claim 1, further comprising determining a methylation status for each of the following, in the DNA of the human subject:
   (d) a methylation locus within gene ZNF542; and
   (e) a methylation locus within gene LONRF2.

3. The method of claim 2, further comprising determining a methylation status for a methylation locus within gene ZNF492 in the DNA of the human subject.

4. The method of claim 1, wherein the methylation locus within gene ZNF132 comprises ZNF132 '415 (SEQ ID NO: 40).

5. The method of claim 4, wherein the first methylation locus within gene ADAMTS2 comprises ADAMTS2 '254 (SEQ ID NO: 21).

6. The method of claim 5, wherein the second methylation locus within gene ADAMTS2 comprises ADAMTS2 '284 (SEQ ID NO: 22).

7. The method of claim 2, wherein the methylation locus within gene ZNF542 comprises ZNF542 '502 (SEQ ID NO: 35).

8. The method of claim 2, wherein the methylation locus within gene LONRF2 comprises LONRF2 '281 (SEQ ID NO: 19).

9. The method of claim 3, wherein the methylation locus within gene ZNF492 comprises ZNF492 '069 (SEQ ID NO: 42).

10. The method of claim 1, wherein the DNA is isolated from blood or plasma of the human subject.

11. The method of claim 1, wherein the DNA is cell-free DNA of the human subject.

12. The method of claim 1, wherein methylation status is determined using quantitative polymerase chain reaction (qPCR).

* * * * *

UNITED STATES PATENT AND TRADEMARK OFFICE
CERTIFICATE OF CORRECTION

PATENT NO. : 11,001,898 B2  
APPLICATION NO. : 16/831756  
DATED : May 11, 2021  
INVENTOR(S) : Marko Bitenc et al.

Page 1 of 1

It is certified that error appears in the above-identified patent and that said Letters Patent is hereby corrected as shown below:

On the Title Page

At Item (12), please change the inventor's last name to Bitenc.

At Item (72), please change the first listed inventor's last name to Bitenc.

Signed and Sealed this  
Twenty-ninth Day of June, 2021

Drew Hirshfeld  
*Performing the Functions and Duties of the*  
*Under Secretary of Commerce for Intellectual Property and*  
*Director of the United States Patent and Trademark Office*